United States Patent
Bursulaya et al.

(10) Patent No.: US 11,203,595 B2
(45) Date of Patent: *Dec. 21, 2021

(54) AZA-INDAZOLE COMPOUNDS FOR USE IN TENDON AND/OR LIGAMENT INJURIES

(71) Applicant: NOVARTIS AG, Basel (CH)

(72) Inventors: Badry Bursulaya, Escondido, CA (US); Andreas Fisch, Basel (CH); James Paul Lajiness, San Diego, CA (US); Rainer Machauer, Freiburg (DE); Swapnil Malekar, Emeryville, CA (US); Hank Michael James Petrassi, San Diego, CA (US); Farshad Ramazani, Basel (CH); Anne-Catherine Remond, Bartenheim (FR); Thomas Ullrich, Bottmingen (CH); Peggy Usselmann, Wahlbach (FR); Eric Vangrevelinghe, Saint-Louis (FR)

(73) Assignee: NOVARTIS AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/941,395

(22) Filed: Jul. 28, 2020

(65) Prior Publication Data
US 2021/0188842 A1 Jun. 24, 2021

Related U.S. Application Data

(63) Continuation of application No. 16/335,496, filed as application No. PCT/IB2017/055737 on Sep. 21, 2017, now Pat. No. 10,766,894.

(60) Provisional application No. 62/398,865, filed on Sep. 23, 2016.

(51) Int. Cl.
| | |
|---|---|
| C07D 471/04 | (2006.01) |
| A61K 9/19 | (2006.01) |
| A61P 21/00 | (2006.01) |
| A61K 9/00 | (2006.01) |
| A61K 9/50 | (2006.01) |
| A61K 31/437 | (2006.01) |
| A61K 31/496 | (2006.01) |
| A61K 31/538 | (2006.01) |

(52) U.S. Cl.
CPC .......... *C07D 471/04* (2013.01); *A61K 9/0019* (2013.01); *A61K 9/5031* (2013.01); *A61K 31/437* (2013.01); *A61K 31/496* (2013.01); *A61K 31/538* (2013.01); *A61P 21/00* (2018.01)

(58) Field of Classification Search
CPC .............................. C07D 471/04; A61K 9/0019
USPC ........................................................ 514/210
See application file for complete search history.

(56) References Cited

U.S. PATENT DOCUMENTS

| | | | | |
|---|---|---|---|---|
| 10,112,907 B2* | 10/2018 | Bursulaya | ............ | A61K 31/454 |
| 10,766,894 B2* | 9/2020 | Bursulaya | ............... | A61P 21/00 |
| 2007/0232620 A1 | 10/2007 | Dorsch et al. | | |
| 2008/0020768 A1 | 1/2008 | Li et al. | | |

FOREIGN PATENT DOCUMENTS

| | | | | |
|---|---|---|---|---|
| RU | 2550821 C2 | 5/2015 | | |
| WO | 2002/50073 A1 | 6/2002 | | |
| WO | 2006/002434 A1 | 1/2006 | | |
| WO | 2006/003276 A1 | 1/2006 | | |
| WO | 2007/017577 A1 | 2/2007 | | |
| WO | WO-2007017577 A1 * | 2/2007 | .............. | A61P 27/02 |
| WO | 2008/154241 A1 | 12/2008 | | |
| WO | 2010/068287 A2 | 6/2010 | | |
| WO | 2016/141796 A2 | 12/2010 | | |
| WO | 2011/019780 A1 | 2/2011 | | |
| WO | 2012/064642 A1 | 5/2012 | | |
| WO | 2012/158810 A1 | 11/2012 | | |
| WO | 2014/140065 A1 | 9/2014 | | |
| WO | 2016161571 A1 | 10/2016 | | |
| WO | WO-2016161571 A1 * | 10/2016 | ........... | C07D 413/14 |
| WO | 2018/055551 A1 | 3/2018 | | |

OTHER PUBLICATIONS

Antonysamy, S. et al., Fragment-based discovery of JAK-2 inhibitors. Bioorganic & Medicinal Chemistry Letters. 2009;19: 279-282.
Argiriadi, M. A. et al., Enabling structure-based drug design of Tyk2 through co-crystallization with a stabilizing aminoindazole inhibitor. BMC Structural Biology. 2012;12/22:1-11.

(Continued)

*Primary Examiner* — Rita J Desai

(57) ABSTRACT

The present invention provides a compound of formula (I) in free form or in pharmaceutically acceptable salt form

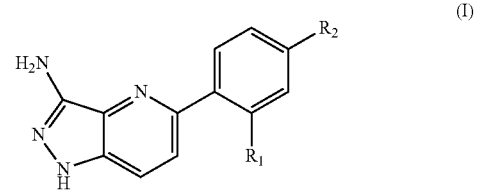

a method for manufacturing the compounds of the invention, and its therapeutic uses. The present invention further provides a combination of pharmacologically active agents and a pharmaceutical composition.

21 Claims, 1 Drawing Sheet
Specification includes a Sequence Listing.

(56) References Cited

OTHER PUBLICATIONS

Caballero, J. et al.,Binding Studies and Quantitative Structure-Activity Relationship of 3-Amino-1H-Indazoles as Inhibitors of GSK3β. Chem Biol Drug Des. 2011;78:631-641.
Dai, Y. et al., Discovery of N-(4-(3-Amino-1H-indazol-4-yl)phenyl)-N'-(2-fluoro-5-methylphenyl)urea (ABT-869), a 3-Aminoindazole-Based Orally Active Multitargeted Receptor Tyrosine Kinase Inhibitor. J. Med. Chem. 2007; 50:1584-1597.
Deng, X. et al., An amino-indazole scaffold with spectrum selective kinase inhibition of FLT3, PDGFRα and kit. Bioorganic & Medicinal Chemistry Letters. 2012; 22:4579-4584.
Witherington, J. et al., 5-Aryl-pyrazolo[3,4-b]pyridazines: Potent Inhibitors of Glycogen Synthase Kinase-3 (GSK-3). Bioorganic & Medicinal Chemistry Letters. 2003;13:1581-1584.
Witherington, J. et al., 5-Aryl-pyrazolo[3,4-b]pyridazines: Potent Inhibitors of Glycogen Synthase Kinase-3 (GSK-3). Bioorganic & Medicinal Chemistry Letters. 2003;13:1577-1580.
Yogo, T. et al., Structure-Based Design and Synthesis of 3-Amino-1,5-dihydro-4H-pyrazolopyridin-4-one Derivatives as Tyrosine Kinase 2 Inhibitors. Journal of Medicinal Chemistry. Dec. 1, 2015; (pp. 1-17=A-Q).
Halland, N., et al., Discovery of N-[4-(1H-Pyrazolo[3,4-b]pyrazin-6-yl)-phenyl]-sulfonamides as Highly Active and Selective SGK1 Inhibitors. Medicinal Chemistry Letters. 2014 (6) 73-78.
Nourissat, et al., Tendon Injury: from biology to tendon repair, Nature Reviews Rheumatology, vol. 11, No. 4, Jan. 1, 2015 (Jan. 1, 2015), pp. 223-233.

\* cited by examiner

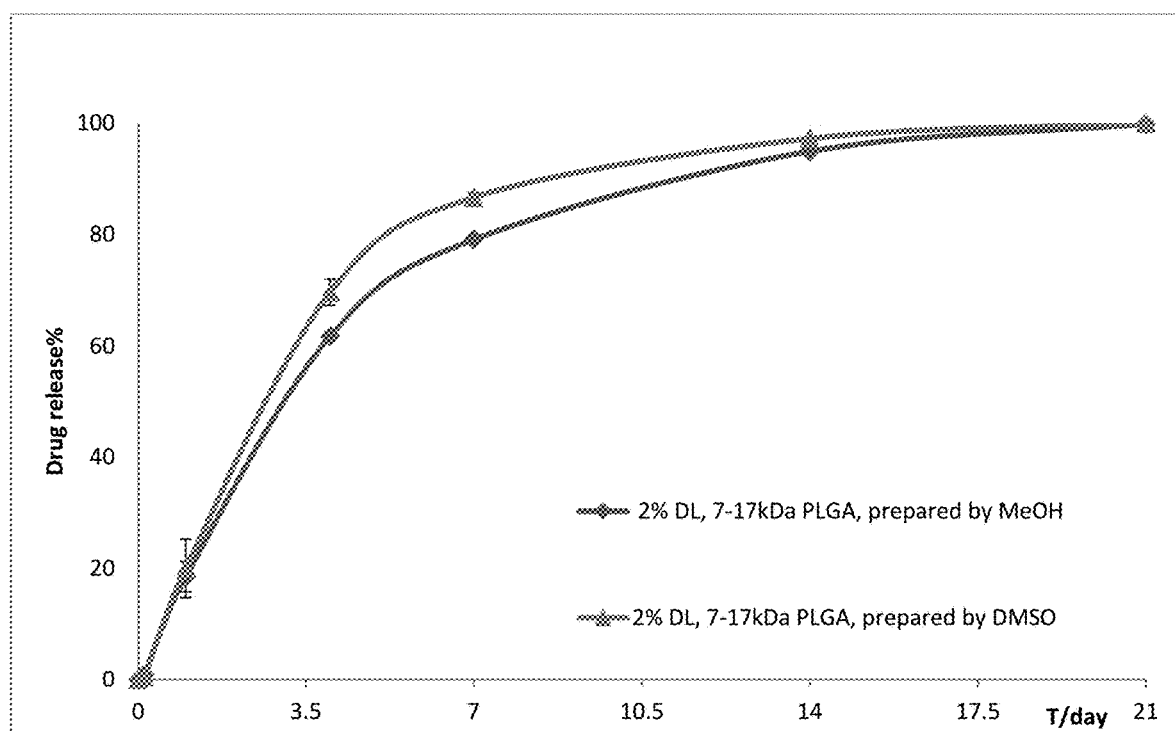

AZA-INDAZOLE COMPOUNDS FOR USE IN TENDON AND/OR LIGAMENT INJURIES

CLAIM OF PRIORITY

This application is a continuation of U.S. patent application Ser. No. 16/335,496, filed on Mar. 21, 2019, which is a 371 U.S. national phase application of international application number PCT/IB2017/055737, filed Sep. 21, 2017, which application claims priority to U.S. provisional patent application No. 62/398,865, filed Sep. 23, 2016, each of which is incorporated herein by reference in its entirety.

FIELD OF THE INVENTION

The invention provides aza-indazole compounds, the use thereof for treating tendon and/or ligament injuries and methods of treating tendon and/or ligament injuries using said compounds.

BACKGROUND OF THE INVENTION

Tendons and ligaments constitute an essential part of the musculoskeletal system by connecting muscles to bones, and bones to bones respectively. Both tendons and ligaments are generated through the same differentiation process (Schweitzer, R. et al. Development, 2001 October; 128(19): 3855-66). While a number of specific growth factors and transcription factors have been found to be involved in tenogenesis during development and repair processes, a detailed understanding of tendon pathologies is still in its infancy.

A review of tendon biology (Duprez D. et al., Nature, 2015, 11, 223-233) summarizes the advances made in tendon biology to date and highlights that there still remains a need for effective treatments of tendon injuries.

To date, the standard of care for tendon rupture is surgery while physiotherapy is being used for tendon degeneration.

Cell therapies and platelet rich plasma are amongst the approaches currently undergoing clinical trials for tendon injuries.

SUMMARY OF THE INVENTION

There is a need to develop compounds which are useful in treating tendon and ligament injuries. Such compound would find applications inter alia in the treatment of tendon and ligament injuries, particularly for tendon and ligament repair.

The invention provides compounds, pharmaceutically acceptable salts thereof, pharmaceutical compositions thereof and combinations thereof, which compounds are inducers of scleraxis gene expression. The invention further provides methods of treating tendon and/or ligament injuries comprising administering to a subject in need thereof an effective amount of a compound of the invention.

Various embodiments of the invention are described herein.

In an embodiment, the invention relates to a compound of formula (I) in free form or in pharmaceutically acceptable salt form

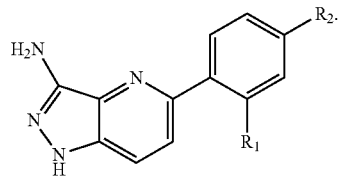

In another embodiment, the invention provides a pharmaceutical composition comprising a therapeutically effective amount of a compound according to the definition of formula (I) in free form or in pharmaceutically acceptable salt form, or subformulae thereof (II), (IIa), (IIb), (III), (IIIa), (IIIb) and one or more pharmaceutically acceptable carriers.

In another embodiment, the invention provides a combination, in particular a pharmaceutical combination, comprising a therapeutically effective amount of the compound according to the definition of formula (I) in free form or in pharmaceutically acceptable salt form, or subformulae thereof (II), (IIa), (IIb), (III), (IIIa), (IIIb) and one or more therapeutically active agent.

In another embodiment, the invention provides a method of treating tendon and/or ligament injury in a subject comprising administering to the subject a therapeutically effective amount of a compound according to the definition of formula (I) in free form or in pharmaceutically acceptable salt form, or subformulae thereof (II), (IIa), (IIb), (III), (IIIa), (IIIb).

In another embodiment, the invention provides a compound according to the definition of formula (I) in free form or in pharmaceutically acceptable salt form, or subformulae thereof (II), (IIa), (IIb), (III), (IIIa), (IIIb) for use as a medicament.

In another embodiment, the invention provides a compound according to the definition of formula (I) in free form or in pharmaceutically acceptable salt form, or subformulae thereof (II), (IIa), (IIb), (III), (IIIa), (IIIb) for use in the treatment of tendon injury.

In another embodiment, the invention provides a compound according to the definition of formula (I) in free form or in pharmaceutically acceptable salt form, or subformulae thereof (II), (IIa), (IIb), (III), (IIIa), (IIIb) for use in the treatment of ligament injury.

In another embodiment, the invention provides the use of a compound according to the definition of formula (I) in free form or in pharmaceutically acceptable salt form, or subformulae thereof (II), (IIa), (IIb), (III), (IIIa), (IIIb) in the manufacture of a medicament for the treatment of tendon and/or ligament injury.

DETAILED DESCRIPTION OF THE INVENTION

The invention relates to a compound of formula (I) in free form or in pharmaceutically acceptable salt form

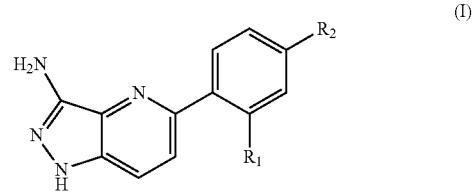

wherein, $R_1$ is selected from $C_1$-$C_3$alkyl and halogen;

$R_2$ is selected from $NHSO_2(CH_2)_nR_3$ or $SO_2NR_5R_6$;

n is 0 or 1;

$R_3$ is selected from phenyl optionally substituted once or more than once with $R_4$; $C_3$-$C_6$cycloalkyl optionally substituted with hydroxyl; a fused bicyclic aromatic ring system;

$R_4$ is independently selected from halogen, $C_1$-$C_3$alkoxy, cyano, $C_1$-$C_3$alkyl, hydroxyl, halo$C_1$-$C_3$alkyl, $NHC(O)CH_3$, halo$C_1$-$C_3$alkoxy, $SO_2NH(CH_3)$; and/or two $R_4$ at adjacent carbon atoms form a 5- or 6-membered heterocyclic non-aromatic ring comprising at least one heteroatom selected from N, O, or S said heterocyclic ring being fused to the phenyl ring and being optionally substituted with $C(O)CH_3$;

$R_5$ is selected from H, $C_1$-$C_3$alkyl;

$R_6$ is selected from a $C_3$-$C_6$cycloalkyl optionally substituted once or more than once with $R_7$; phenyl optionally substituted once or more than once with halogen; $C_1$-$C_6$alkyl optionally substituted with hydroxyl; 4- to 6-membered heterocyclic non-aromatic ring comprising at least one heteroatom selected from N, O or S optionally substituted once or more than once with oxo; benzyl;

$R_7$ is independently selected from hydroxyl, halo$C_1$-$C_3$alkyl, halogen, $C_1$-$C_3$alkyl, C(O)OH, hydroxy$C_1$-$C_3$alkyl;

or $R_5$ and $R_6$ together with the N atom to which they are attached form a 4-, 5- or 6-membered heterocyclic non-aromatic ring optionally comprising one additional heteroatom selected from N, O or S, said ring being optionally substituted once or more than once with $R_8$; a 6- to 8-membered saturated bicyclic ring system;

$R_8$ is independently selected from halogen; hydroxy$C_1$-$C_3$alkyl; $C(O)NH_2$; hydroxyl; halo$C_1$-$C_3$alkyl optionally substituted with hydroxyl; phenoxy; $SO_2C_1$-$C_3$alkyl.

Unless specified otherwise, the terms "compounds of the present invention" or "compounds of the invention" refer to compounds of formula (I), or subformulae thereof (II), (IIa), (IIb), (III), (IIIa), (IIIb) and salts thereof, as well as all stereoisomers (including diastereoisomers and enantiomers), rotamers, tautomers, isomeric internal addition products and isotopically labeled compounds (including deuterium substitutions), as well as inherently formed moieties.

As used herein, the term "$C_1$-$C_3$alkyl" refers to a straight or branched hydrocarbon chain radical consisting solely of carbon and hydrogen atoms, containing no unsaturation, having from one to three carbon atoms, and which is attached to the rest of the molecule by a single bond. Examples of $C_1$-$C_3$alkyl include methyl, ethyl, n-propyl, 1-methylethyl (iso-propyl).

As used herein, the term "hydroxy$C_1$-$C_3$alkyl" refers to a radical of formula —$R_a$—OH, wherein $R_a$ is $C_{1-3}$alkyl as defined above. Examples of hydroxy$C_1$-$C_3$alkyl include, but are not limited to, hydroxy-methyl, 2-hydroxy-ethyl, 2-hydroxy-propyl, 3-hydroxy-propyl.

As used herein, the term "$C_3$-$C_6$cycloalkyl" refers to saturated monocyclic hydrocarbon groups of 3-6 carbon atoms. The term "$C_4$-$C_6$cycloalkyl" is to be construed accordingly. Examples of $C_4$-$C_6$cycloalkyl include cyclobutyl, cyclopentyl and cyclohexyl.

As used herein, the term "$C_1$-$C_3$alkoxy" refers to a radical of the formula —$OR_a$ where $R_a$ is a $C_1$-$C_3$alkyl radical as generally defined above. Examples of $C_1$-$C_3$alkoxy include, but are not limited to, methoxy, ethoxy, propoxy, iso-propoxy.

"Halogen" or "halo" refers to bromo, chloro, fluoro or iodo.

As used herein, the term "halogen$C_1$-$C_3$alkyl" or "halo$C_1$-$C_3$alkyl" refers to $C_1$-$C_3$alkyl radical, as defined above, substituted by one or more halo radicals, as defined above. Examples of halogen$C_1$-$C_3$alkyl include, but are not limited to, trifluoromethyl, difluoromethyl, fluoromethyl, trichloromethyl, 2,2,2-trifluoroethyl, 1-fluoromethyl-2-fluoroethyl, 3-bromo-2-fluoropropyl and 1-bromomethyl-2-bromoethyl.

As used herein, the term "halo$C_1$-$C_3$alkoxy" refers to a $C_1$-$C_3$alkoxy radical, as defined above, substituted by one or more halo radicals, as defined above. Examples of halo$C_1$-$C_3$alkoxy include trifluoromethoxy.

As used herein the term "5- or 6-membered heterocyclic non-aromatic ring comprising at least one heteroatom selected form N, O or S" when referring to two $R_4$ at adjacent carbon atoms of a phenyl ring refers to a 5- or 6-membered saturated or unsaturated non-aromatic ring comprising at least one heteroatom selected from N, O or S and includes, but is not limited to, dioxolane, morpholine.

As used herein the term "4- to 6-membered heterocyclic non-aromatic ring comprising at least one heteroatom selected from N, O or S" in relation to $R_6$ refers to a 4-, 5- or 6-membered saturated or unsaturated ring comprising at least one heteroatom selected form N, O or S wherein the ring is attached to the rest of the molecule via a ring carbon atom and includes, but is not limited to, tetrahydrothiophene, tetrahydrothiopyran.

As used herein the term "4-, 5- or 6-membered heterocyclic non-aromatic ring optionally comprising one additional heteroatom selected from N, O or S" when referring to $R_5$ and $R_6$ together with the N atom to which they are attached refers to a 4-, 5- or 6-membered N-containing saturated or unsaturated ring optionally comprising one additional heteroatom selected from N, O or S and includes, but is not limited to, azetidine, pyrrolidine, piperidine, morpholine. Preferably, it is pyrrolidine.

As used herein, the term "6- to 8-membered saturated bicyclic ring system" when referring to $R_5$ and $R_6$ together with the N atom to which they are attached refers to a 6-, 7- or 8-membered N-containing saturated bicyclic ring system and includes, but is not limited to, hexahydrocyclopentapyrrole, azabicyclo[3.1.0]hexane.

As used herein, the term "optionally substituted once or more than once" preferably means once, twice or three times.

As used herein, "tendon" refers to the connective tissue that connects muscle to bone and is capable of withstanding tension. Preferably, tendon refers to the Achilles tendon or to a rotator cuff tendon.

As used herein, "ligament" refers to the connective tissue that connects bone to bone.

As used herein, the term "tendon injury" or "tendon injuries" includes both acute and chronic injuries. Acute injuries are the result of a traumatic event leading for example to partial or full rupture of the tendon. Chronic injuries are those leading to tendon degeneration without rupture of the tendon. Acute injuries can also occur on top of chronic injuries leading to possible subsequent partial or full rupture of the degenerated tendon.

As used herein, the term "ligament injury" or "ligament injuries" includes both acute and chronic injuries. Acute injuries are the result of a traumatic event leading for example to partial or full rupture of the ligament. Chronic injuries are those leading to ligament degeneration without rupture of the ligament. Acute injuries can also occur on top of chronic injuries leading to possible subsequent partial or full rupture of the degenerated ligament.

As used herein, the term "tenogenesis" refers to the generation of tendon or ligament tissue. The generation of ligament tissue can also be referred to as ligamentogenesis. Tenogenesis may be achieved by induction of scleraxis gene expression, tenomodulin gene expression and/or collagen type I (Col1a2).

In an embodiment, the invention relates to a compound of formula (II) in free form or in pharmaceutically acceptable salt form

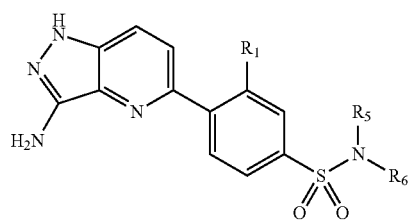

(II)

wherein $R_1$, $R_5$ and $R_6$ are as defined herein in relation to a compound of formula (I).

In an embodiment, the invention relates to a compound of formula (IIa) in free form or in pharmaceutically acceptable salt form

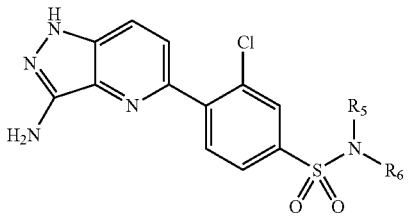

(IIa)

wherein $R_5$ and $R_6$ are as defined herein in relation to a compound of formula (I).

In an embodiment, the invention relates to a compound of formula (IIb) in free form or in pharmaceutically acceptable salt form

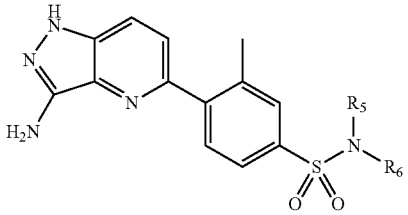

(IIb)

wherein $R_5$ and $R_6$ are as defined herein in relation to a compound of formula (I).

In an embodiment, the invention relates to a compound of formula (III) in free form or in pharmaceutically acceptable salt form

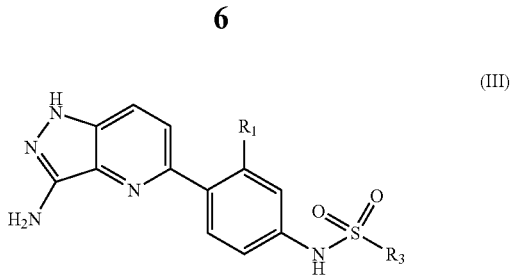

(III)

wherein $R_1$ and $R_3$ are as defined herein in relation to a compound of formula (I).

In an embodiment, the invention relates to a compound of formula (IIIa) in free form or in pharmaceutically acceptable salt form

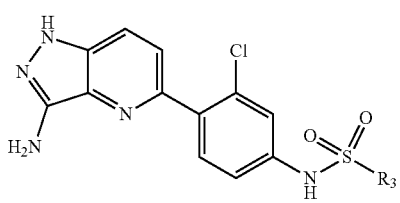

(IIIa)

wherein $R_3$ is as defined herein in relation to a compound of formula (I).

In an embodiment, the invention relates to a compound of formula (IIIa) in free form or in pharmaceutically acceptable salt form

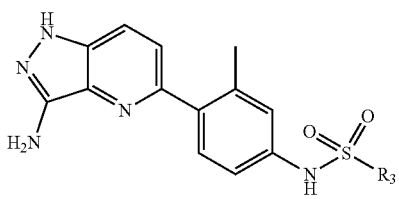

(IIIb)

wherein $R_3$ is as defined herein in relation to a compound of formula (I).

Various enumerated embodiments of the invention are described herein. It will be recognized that features specified in each embodiment may be combined with other specified features to provide further embodiments of the present invention.

Embodiment 1. A compound of formula (I) in free form or in pharmaceutically acceptable salt form

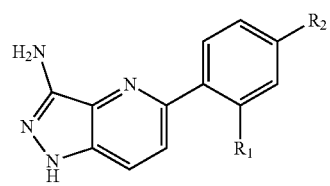

(I)

wherein,
$R_1$ is selected from $C_1$-$C_3$alkyl and halogen;
$R_2$ is selected from $NHSO_2(CH_2)_nR_3$ or $SO_2NR_5R_6$;
n is 0 or 1;

R₃ is selected from phenyl optionally substituted once or more than once with R₄; C₃-C₆cycloalkyl optionally substituted with hydroxyl; a fused bicyclic aromatic ring system;

R₄ is independently selected from halogen, $C_1$-$C_3$alkoxy, cyano, $C_1$-$C_3$alkyl, hydroxyl, halo$C_1$-$C_3$alkyl, NHC(O)CH₃, halo$C_1$-$C_3$alkoxy, SO₂NH(CH₃); and/or two R₄ at adjacent carbon atoms form a 5- or 6-membered heterocyclic non-aromatic ring comprising at least one heteroatom selected from N, O, or S said heterocyclic ring being fused to the phenyl ring and being optionally substituted with C(O)CH₃;

R₅ is selected from H, $C_1$-$C_3$alkyl;

R₆ is selected from a C₃-C₆cycloalkyl optionally substituted once or more than once with R₇; phenyl optionally substituted once or more than once with halogen; $C_1$-$C_6$alkyl optionally substituted with hydroxyl; 4- to 6-membered heterocyclic non-aromatic ring comprising at least one heteroatom selected from N, O or S optionally substituted once or more than once with oxo; benzyl;

R₇ is independently selected from hydroxyl, halo$C_1$-$C_3$alkyl, halogen, $C_1$-$C_3$alkyl, C(O)OH, hydroxy$C_1$-$C_3$alkyl;

or

R₅ and R₆ together with the N atom to which they are attached form a 4-, 5- or 6-membered heterocyclic non-aromatic ring optionally comprising one additional heteroatom selected from N, O or S, said ring being optionally substituted once or more than once with R₈; a 6- to 8-membered saturated bicyclic ring system;

R₈ is independently selected from halogen; hydroxy$C_1$-$C_3$alkyl; C(O)NH₂; hydroxyl; halo$C_1$-$C_3$alkyl optionally substituted with hydroxyl; phenoxy; SO₂$C_1$-$C_3$alkyl.

Embodiment 2. A compound according to embodiment 1, of formula (II) in free form or in pharmaceutically acceptable salt form

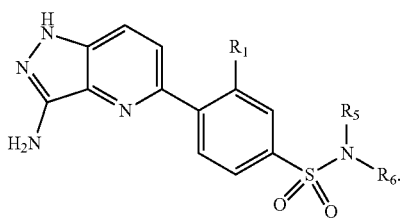

(II)

Embodiment 3. A compound according to embodiment 1 or 2 of formula (IIa) in free form or in pharmaceutically acceptable salt form

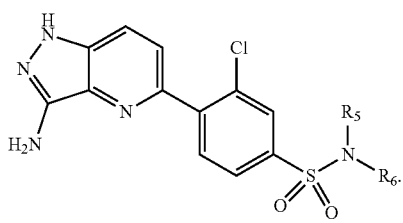

(IIa)

Embodiment 4. A compound according to embodiment 1 or 2 of formula (IIb) in free form or in pharmaceutically acceptable salt form

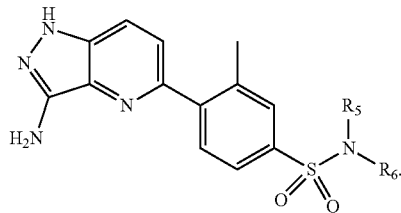

(IIb)

Embodiment 5. A compound according to any of embodiment 1 to 4, wherein
R₅ is H or methyl;
R₆ is a C₃-C₆cycloalkyl optionally substituted once or more than once with R₇; and
R₇ is independently selected from hydroxyl, halo$C_1$-$C_3$alkyl, halogen, $C_1$-$C_3$alkyl, hydroxyl-$C_1$-$C_3$alkyl.

Embodiment 6. A compound according to any of embodiments 1 to 5, wherein R₅ is H or methyl;
R₆ is cyclobutyl substituted once or twice with R₇; and
R₇ is independently selected from hydroxyl, halo$C_1$-$C_3$alkyl, halogen.

Embodiment 7. A compound according to any of embodiments 1 to 5, wherein R₅ is H or methyl;
R₆ is cyclopentyl substituted once with hydroxyl or hydroxy$C_1$-$C_3$alkyl.

Embodiment 8. A compound according to any of embodiments 1 to 5, wherein R₅ is H or methyl;
R₆ is cyclohexyl substituted once or twice with R₇; and
R₇ is independently selected from hydroxyl or $C_1$-$C_3$alkyl.

Embodiment 9. A compound according to any of embodiments 1 to 4, wherein R₅ and R₆ together with the N atom to which they are attached form a 5-membered heterocyclic non-aromatic ring being substituted once, twice or three times with R₈;
R₈ is independently selected from halogen, hydroxyl-$C_1$-$C_3$alkyl.

Embodiment 10. A compound according to embodiment 1 of formula (III) in free form or in pharmaceutically acceptable salt form

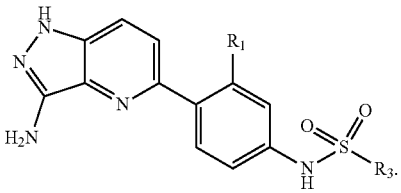

(III)

Embodiment 11. A compound according to embodiment 10 of formula (IIIa) in free form or in pharmaceutically acceptable salt form

(IIIa)

Embodiment 12. A compound according to embodiment 10 of formula (IIIb) in free form or in pharmaceutically acceptable salt form

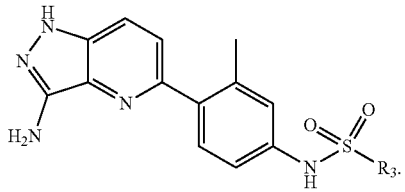

(IIIb)

Embodiment 13. A compound according to any of embodiments 1 or 10 to 12 in free form or in pharmaceutically acceptable salt form, wherein $R_3$ is phenyl optionally substituted once or more than once with $R_4$; and $R_4$ is independently selected from halogen, $C_1$-$C_3$alkoxy, cyano.

Embodiment 14. A compound according to embodiment 13 in free form or in pharmaceutically acceptable salt form, wherein $R_3$ is phenyl optionally substituted once or more than once with halogen.

Embodiment 15. A compound according to embodiment 1 in free form or in pharmaceutically acceptable salt form, which is selected from 4-(3-amino-1H-pyrazolo[4,3-b]pyridin-5-yl)-3-chloro-N-(3-hydroxy-3-(trifluoromethyl)cyclobutyl)benzenesulfonamide;
4-(3-amino-1H-pyrazolo[4,3-b]pyridin-5-yl)-N-(3-hydroxy-3-(trifluoromethyl)cyclobutyl)-3-methylbenzenesulfonamide;
N-(4-(3-amino-1H-pyrazolo[4,3-b]pyridin-5-yl)-3-chlorophenyl)-4-chlorobenzenesulfonamide; 4-(3-amino-1H-pyrazolo[4,3-b]pyridin-5-yl)-3-chloro-N-(3,3-difluorocyclobutyl)benzenesulfonamide;
N-(4-(3-amino-1H-pyrazolo[4,3-b]pyridin-5-yl)-3-chlorophenyl)-4-methoxybenzenesulfonamide;
N-(4-(3-amino-1H-pyrazolo[4,3-b]pyridin-5-yl)-3-chlorophenyl)-4-fluorobenzenesulfonamide; 4-(3-amino-1H-pyrazolo[4,3-b]pyridin-5-yl)-3-chloro-N-(2-hydroxycyclopentyl)benzenesulfonamide;
4-(3-amino-1H-pyrazolo[4,3-b]pyridin-5-yl)-N-(3,3-difluorocyclobutyl)-3-methylbenzenesulfonamide;
4-(3-amino-1H-pyrazolo[4,3-b]pyridin-5-yl)-N-(3-hydroxy-3-(trifluoromethyl)cyclobutyl)-N,3-dimethylbenzenesulfonamide;
N-(4-(3-amino-1H-pyrazolo[4,3-b]pyridin-5-yl)-3-chlorophenyl)-3,4-difluorobenzenesulfonamide;
N-(4-(3-amino-1H-pyrazolo[4,3-b]pyridin-5-yl)-3-chlorophenyl)benzo[d][1,3]dioxole-5-sulfonamide;
4-(3-amino-1H-pyrazolo[4,3-b]pyridin-5-yl)-3-chloro-N-(2-hydroxycyclohexyl)benzenesulfonamide;
N-(4-(3-amino-1H-pyrazolo[4,3-b]pyridin-5-yl)-3-chlorophenyl)-4-chloro-3-fluorobenzenesulfonamide;
N-(4-(3-amino-1H-pyrazolo[4,3-b]pyridin-5-yl)-3-chlorophenyl)-2-hydroxycyclohexane-1-sulfonamide;
N-(4-(3-amino-1H-pyrazolo[4,3-b]pyridin-5-yl)-3-chlorophenyl)cyclohexanesulfonamide; 4-(3-amino-1H-pyrazolo[4,3-b]pyridin-5-yl)-3-methyl-N-phenylbenzenesulfonamide;
1-((4-(3-amino-1H-pyrazolo[4,3-b]pyridin-5-yl)-3-chlorophenyl)sulfonyl)-4,4-difluoropyrrolidin-2-yl)methanol;
4-(3-amino-1H-pyrazolo[4,3-b]pyridin-5-yl)-N-(3-hydroxycyclopentyl)-3-methylbenzenesulfonamide;
4-(3-amino-1H-pyrazolo[4,3-b]pyridin-5-yl)-N-(2-hydroxycyclopentyl)-3-methylbenzenesulfonamide;
5-(4-((hexahydrocyclopenta[c]pyrrol-2(1H)-yl)sulfonyl)-2-methylphenyl)-1H-pyrazolo[4,3-b]pyridin-3-amine;
N-(4-(3-amino-1H-pyrazolo[4,3-b]pyridin-5-yl)-3-chlorophenyl)-3-cyanobenzenesulfonamide; 4-(3-amino-1H-pyrazolo[4,3-b]pyridin-5-yl)-3-chloro-N-(3-hydroxycyclopentyl)benzenesulfonamide;
4-(3-amino-1H-pyrazolo[4,3-b]pyridin-5-yl)-3-chloro-N-(4,4-dimethylcyclohexyl)benzenesulfonamide;
N-(4-(3-amino-1H-pyrazolo[4,3-b]pyridin-5-yl)-3-chlorophenyl)-4-methylbenzenesulfonamide; 4-(3-amino-1H-pyrazolo[4,3-b]pyridin-5-yl)-N-(1-(hydroxymethyl)cyclopentyl)-3-methylbenzenesulfonamide;
N-(4-(3-amino-1H-pyrazolo[4,3-b]pyridin-5-yl)-3-chlorophenyl)-3-chloro-4-fluorobenzenesulfonamide;
N-(4-(3-amino-1H-pyrazolo[4,3-b]pyridin-5-yl)-3-chlorophenyl)-3-chlorobenzenesulfonamide; 4-(3-amino-1H-pyrazolo[4,3-b]pyridin-5-yl)-3-chloro-N-(1-(hydroxymethyl)cyclopentyl)benzenesulfonamide;)
4-(3-amino-1H-pyrazolo[4,3-b]pyridin-5-yl)-3-chloro-N-(1,1-dioxidotetrahydrothiophen-3-yl)benzenesulfonamide;
N-(4-(3-amino-1H-pyrazolo[4,3-b]pyridin-5-yl)-3-chlorophenyl)-2-hydroxy-5-methylbenzenesulfonamide;
N-(4-(3-amino-1H-pyrazolo[4,3-b]pyridin-5-yl)-3-methylphenyl)-3-fluorobenzenesulfonamide; 1-((4-(3-amino-1H-pyrazolo[4,3-b]pyridin-5-yl)-3-methylphenyl)sulfonyl)-4,4-difluoropyrrolidine-2-carboxamide;
4-(3-amino-1H-pyrazolo[4,3-b]pyridin-5-yl)-3-chloro-N-(;2-hydroxycyclopentyl)benzenesulfonamide;
4-(3-amino-1H-pyrazolo[4,3-b]pyridin-5-yl)-3-chloro-N-(4-methylcyclohexyl)benzenesulfonamide;
1-((4-(3-amino-1H-pyrazolo[4,3-b]pyridin-5-yl)-3-methylphenyl)sulfonyl)-4,4-difluoropyrrolidin-2-yl)methanol;
4-(3-amino-1H-pyrazolo[4,3-b]pyridin-5-yl)-3-chloro-N-phenylbenzenesulfonamide;
4-(3-amino-1H-pyrazolo[4,3-b]pyridin-5-yl)-N-cyclohexyl-3-methylbenzenesulfonamide;
4-(3-amino-1H-pyrazolo[4,3-b]pyridin-5-yl)-N-cyclohexyl-3-methylbenzenesulfonamide;
N-(4-(3-amino-1H-pyrazolo[4,3-b]pyridin-5-yl)-3-chlorophenyl)-3-fluorobenzenesulfonamide;
N-(4-(3-amino-1H-pyrazolo[4,3-b]pyridin-5-yl)-3-methylphenyl)-3-chlorobenzenesulfonamide;
N-(4-(3-amino-1H-pyrazolo[4,3-b]pyridin-5-yl)-3-chlorophenyl)-3,4-dichlorobenzenesulfonamide;
4-(3-amino-1H-pyrazolo[4,3-b]pyridin-5-yl)-3-chloro-N-(3-hydroxycyclohexyl)benzenesulfonamide;
4-(3-amino-1H-pyrazolo[4,3-b]pyridin-5-yl)-3-chloro-N-(4-hydroxycyclohexyl)benzenesulfonamide;
N-(4-(3-amino-1H-pyrazolo[4,3-b]pyridin-5-yl)-3-chlorophenyl)benzenesulfonamide;
4-(3-amino-1H-pyrazolo[4,3-b]pyridin-5-yl)-N-(3-(hydroxymethyl)cyclobutyl)-3-methylbenzenesulfonamide;
4-(3-amino-1H-pyrazolo[4,3-b]pyridin-5-yl)-3-fluoro-N-phenylbenzenesulfonamide;
4-(3-amino-1H-pyrazolo[4,3-b]pyridin-5-yl)-3-chloro-N-(1,1-dioxidotetrahydro-2H-thiopyran-4-yl)benzenesulfonamide;
5-(2-chloro-4-((hexahydrocyclopenta[c]pyrrol-2(1H)-yl)sulfonyl)phenyl)-1H-pyrazolo[4,3-b]pyridin-3-amine;
4-(3-amino-1H-pyrazolo[4,3-b]pyridin-5-yl)-3-chloro-N-(3-chloro-2-fluorophenyl)benzenesulfonamide;

N-(4-(3-amino-1H-pyrazolo[4,3-b]pyridin-5-yl)-3-chlorophenyl)-3,4-dihydro-2H-benzo[b][1,4]oxazine-6-sulfonamide;

1-((4-(3-amino-1H-pyrazolo[4,3-b]pyridin-5-yl)-3-chlorophenyl)sulfonyl)-4-fluoropyrrolidine-2-carboxamide;

4-(3-amino-1H-pyrazolo[4,3-b]pyridin-5-yl)-3-chloro-N-(2,3-dichlorophenyl)benzenesulfonamide;

1-((4-(3-amino-1H-pyrazolo[4,3-b]pyridin-5-yl)-3-chlorophenyl)sulfonyl)pyrrolidin-3-ol;

4-(3-amino-1H-pyrazolo[4,3-b]pyridin-5-yl)-3-chloro-N-(4-hydroxy-4-methylcyclohexyl)benzenesulfonamide;

N-(4-(3-amino-1H-pyrazolo[4,3-b]pyridin-5-yl)-3-chlorophenyl)-1-phenylmethanesulfonamide;

N-(5-(N-(4-(3-amino-1H-pyrazolo[4,3-b]pyridin-5-yl)-3-chlorophenyl)sulfamoyl)-2-methoxyphenyl)acetamide;

N-(4-(3-amino-1H-pyrazolo[4,3-b]pyridin-5-yl)-3-chlorophenyl)-3-(trifluoromethyl)benzenesulfonamide;

5-(4-(3-azabicyclo[3.1.0]hexan-3-ylsulfonyl)-2-chlorophenyl)-1H-pyrazolo[4,3-b]pyridin-3-amine;

4-(3-amino-1H-pyrazolo[4,3-b]pyridin-5-yl)-N-(3-hydroxycyclobutyl)-3-methylbenzenesulfonamide;

4-(3-amino-1H-pyrazolo[4,3-b]pyridin-5-yl)-N-(3-hydroxycyclohexyl)-3-methylbenzenesulfonamide;

1-((4-(3-amino-1H-pyrazolo[4,3-b]pyridin-5-yl)-3-methylphenyl)sulfonyl)-3-(trifluoromethyl)azetidin-3-ol;

N-(4-(3-amino-1H-pyrazolo[4,3-b]pyridin-5-yl)-3-chlorophenyl)-3-methoxybenzenesulfonamide;

4-(3-amino-1H-pyrazolo[4,3-b]pyridin-5-yl)-N-(4-hydroxy-4-(trifluoromethyl)cyclohexyl)-3-methylbenzenesulfonamide;

4-(3-amino-1H-pyrazolo[4,3-b]pyridin-5-yl)-N-(4-hydroxycyclohexyl)-3-methylbenzenesulfonamide;

1-((4-(3-amino-1H-pyrazolo[4,3-b]pyridin-5-yl)-3-methylphenyl)sulfonyl)pyrrolidin-2-yl)methanol;

4-(3-amino-1H-pyrazolo[4,3-b]pyridin-5-yl)-3-chloro-N-(2-hydroxyethyl)benzenesulfonamide;

4-(3-amino-1H-pyrazolo[4,3-b]pyridin-5-yl)-N-benzyl-3-chlorobenzenesulfonamide;

N-(4-(3-amino-1H-pyrazolo[4,3-b]pyridin-5-yl)-3-chlorophenyl)pyridine-3-sulfonamide;

5-(2-chloro-4-((3,3-difluoroazetidin-1-yl)sulfonyl)phenyl)-1H-pyrazolo[4,3-b]pyridin-3-amine;

4-(3-amino-1H-pyrazolo[4,3-b]pyridin-5-yl)-N-tert-butyl-3-fluorobenzenesulfonamide;

N1-(4-(3-amino-1H-pyrazolo[4,3-b]pyridin-5-yl)-3-chlorophenyl)-N4-methyl benzene-1,4-disulfonamide;

N-(4-(3-amino-1H-pyrazolo[4,3-b]pyridin-5-yl)-3-chlorophenyl)-4-(trifluoromethyl)benzenesulfonamide;

N-(4-(3-amino-1H-pyrazolo[4,3-b]pyridin-5-yl)-3-chlorophenyl)-3,4-dimethoxybenzenesulfonamide;

4-(3-amino-1H-pyrazolo[4,3-b]pyridin-5-yl)-N-(4-hydroxy-4-methylcyclohexyl)-3-methylbenzenesulfonamide;

4-(3-amino-1H-pyrazolo[4,3-b]pyridin-5-yl)-3-chloro-N-(2,3-difluorophenyl)benzenesulfonamide;

N-(4-(3-amino-1H-pyrazolo[4,3-b]pyridin-5-yl)-3-chlorophenyl)naphthalene-2-sulfonamide; 2-(1-((4-(3-amino-1H-pyrazolo[4,3-b]pyridin-5-yl)-3-methylphenyl)sulfonyl)pyrrolidin-3-yl)ethanol;

N-(4-(3-amino-1H-pyrazolo[4,3-b]pyridin-5-yl)-3-chlorophenyl)-3-methylbenzenesulfonamide; 4-(3-amino-1H-pyrazolo[4,3-b]pyridin-5-yl)-3-chloro-N-(3-(hydroxymethyl)cyclobutyl)benzenesulfonamide;

4-acetyl-N-(4-(3-amino-1H-pyrazolo[4,3-b]pyridin-5-yl)-3-chlorophenyl)-3,4-dihydro-2H-benzo[b][1,4]oxazine-6-sulfonamide;

5-(2-chloro-4-((3-phenoxyazetidin-1-yl)sulfonyl)phenyl)-1H-pyrazolo[4,3-b]pyridin-3-amine;

N-(4-(3-amino-1H-pyrazolo[4,3-b]pyridin-5-yl)-3-chlorophenyl)-4-(trifluoromethoxy)benzenesulfonamide;

2-(4-((4-(3-amino-1H-pyrazolo[4,3-b]pyridin-5-yl)-3-chlorophenyl)sulfonyl)piperazin-2-yl)-1,1,1-trifluoropropan-2-ol;

4-(3-amino-1H-pyrazolo[4,3-b]pyridin-5-yl)-3-chloro-N-(3-chlorophenyl)benzenesulfonamide;

4-(3-amino-1H-pyrazolo[4,3-b]pyridin-5-yl)-N-(2-hydroxycyclohexyl)-3-methylbenzenesulfonamide;

4-(3-amino-1H-pyrazolo[4,3-b]pyridin-5-yl)-3-chloro-N-(1,1-dioxidothietan-3-yl)benzenesulfonamide; and 5-(2-chloro-4-((3-(methylsulfonyl)azetidin-1-yl)sulfonyl)phenyl)-1H-pyrazolo[4,3-b]pyridin-3-amine.

Embodiment 16. A compound according to embodiment 15 in free form or in pharmaceutically acceptable salt form, which is selected from 4-(3-amino-1H-pyrazolo[4,3-b]pyridin-5-yl)-3-chloro-N-((1s,3s)-3-hydroxy-3-(trifluoromethyl)cyclobutyl)benzenesulfonamide;

4-(3-amino-1H-pyrazolo[4,3-b]pyridin-5-yl)-N-((1s,3s)-3-hydroxy-3-(trifluoromethyl)cyclobutyl)-3-methylbenzenesulfonamide;

4-(3-amino-1H-pyrazolo[4,3-b]pyridin-5-yl)-3-chloro-N-((1R,2S)-2-hydroxycyclopentyl)benzenesulfonamide;

4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide;

(1S,2R)-N-(4-(3-amino-1H-pyrazolo[4,3-b]pyridin-5-yl)-3-chlorophenyl)-2-hydroxycyclohexane-1-sulfonamide;

(S)-(1-((4-(3-amino-1H-pyrazolo[4,3-b]pyridin-5-yl)-3-chlorophenyl)sulfonyl)-4,4-difluoropyrrolidin-2-yl)methanol;

4-(3-amino-1H-pyrazolo[4,3-b]pyridin-5-yl)-N-((1R,3S)-3-hydroxycyclopentyl)-3-methylbenzenesulfonamide;

4-(3-amino-1H-pyrazolo[4,3-b]pyridin-5-yl)-N-((1R,2S)-2-hydroxycyclopentyl)-3-methylbenzenesulfonamide;

4-(3-amino-1H-pyrazolo[4,3-b]pyridin-5-yl)-3-chloro-N-((1R,3S)-3-hydroxycyclopentyl)benzenesulfonamide;

4-(3-amino-1H-pyrazolo[4,3-b]pyridin-5-yl)-3-chloro-N-((1R,2R)-2-hydroxycyclopentyl)benzenesulfonamide;

4-(3-amino-1H-pyrazolo[4,3-b]pyridin-5-yl)-3-chloro-N-((1S,2R)-2-hydroxycyclopentyl)benzenesulfonamide;

(S)-(1-((4-(3-amino-1H-pyrazolo[4,3-b]pyridin-5-yl)-3-methylphenyl)sulfonyl)-4,4-difluoropyrrolidin-2-yl)methanol;

4-(3-amino-1H-pyrazolo[4,3-b]pyridin-5-yl)-3-chloro-N-((1r,4r)-4-hydroxycyclohexyl)benzenesulfonamide;

4-(3-amino-1H-pyrazolo[4,3-b]pyridin-5-yl)-N-((1s,3s)-3-(hydroxymethyl)cyclobutyl)-3-methylbenzenesulfonamide;

4-(3-amino-1H-pyrazolo[4,3-b]pyridin-5-yl)-3-chloro-N-((1s,4s)-4-hydroxycyclohexyl)benzenesulfonamide;

4-(3-amino-1H-pyrazolo[4,3-b]pyridin-5-yl)-N-((1r,4r)-4-hydroxycyclohexyl)-3-methylbenzenesulfonamide;

(2R,4R)-1-((4-(3-amino-1H-pyrazolo[4,3-b]pyridin-5-yl)-3-chlorophenyl)sulfonyl)-4-fluoropyrrolidine-2-carboxamide;

(R)-1-((4-(3-amino-1H-pyrazolo[4,3-b]pyridin-5-yl)-3-chlorophenyl)sulfonyl)pyrrolidin-3-ol;

4-(3-amino-1H-pyrazolo[4,3-b]pyridin-5-yl)-3-chloro-N-((1r,4r)-4-hydroxy-4-methylcyclohexyl)benzenesulfonamide;

(1R,2S)-N-(4-(3-amino-1H-pyrazolo[4,3-b]pyridin-5-yl)-3-chlorophenyl)-2-hydroxycyclohexane-1-sulfonamide;

4-(3-amino-1H-pyrazolo[4,3-b]pyridin-5-yl)-N-((1s, 3s)-3-hydroxycyclobutyl)-3-methylbenzenesulfonamide;
4-(3-amino-1H-pyrazolo[4,3-b]pyridin-5-yl)-N-((1r,4r)-4-hydroxy-4-(trifluoromethyl)cyclohexyl)-3-methylbenzenesulfonamide;
4-(3-amino-1H-pyrazolo[4,3-b]pyridin-5-yl)-N-((1s,4s)-4-hydroxycyclohexyl)-3-methylbenzenesulfonamide;
(S)-(1-((4-(3-amino-1H-pyrazolo[4,3-b]pyridin-5-yl)-3-methylphenyl)sulfonyl)pyrrolidin-2-yl)methanol;
(S)-1-((4-(3-amino-1H-pyrazolo[4,3-b]pyridin-5-yl)-3-chlorophenyl)sulfonyl)pyrrolidin-3-ol;
4-(3-amino-1H-pyrazolo[4,3-b]pyridin-5-yl)-N-((1r, 3r)-3-hydroxycyclobutyl)-3-methylbenzenesulfonamide;
4-(3-amino-1H-pyrazolo[4,3-b]pyridin-5-yl)-N-((1r,4r)-4-hydroxy-4-methylcyclohexyl)-3-methylbenzenesulfonamide;
4-(3-amino-1H-pyrazolo[4,3-b]pyridin-5-yl)-3-chloro-N-((1s,3s)-3-(hydroxymethyl)cyclobutyl)benzenesulfonamide; and
4-(3-amino-1H-pyrazolo[4,3-b]pyridin-5-yl)-3-chloro-N-((1S,2S)-2-hydroxycyclopentyl)benzenesulfonamide.

Embodiment 17. A pharmaceutical composition comprising a therapeutically effective amount of a compound according to any one of embodiments 1 to 16 in free form or in pharmaceutically acceptable salt form and one or more pharmaceutically acceptable carriers.

Embodiment 18. A combination comprising a therapeutically effective amount of a compound according to any one of embodiments 1 to 16 in free form or in pharmaceutically acceptable salt form and one or more therapeutically active agents.

Embodiment 19. A compound according to any one of embodiments 1 to 16 in free form or in pharmaceutically acceptable salt form for use as a medicament.

Embodiment 20. A compound according to any one of embodiments 1 to 16 in free form or in pharmaceutically acceptable salt form for use in the treatment of a tendon injury.

Embodiment 21. A compound for use according to embodiment 20, wherein the tendon injury is a tendon partial rupture.

Embodiment 22. A compound for use according to embodiment 20, wherein the tendon injury is a tendon full rupture.

Embodiment 23. A compound for use according to embodiment 20 in free form or in pharmaceutically acceptable salt form wherein the tendon injury is tendon degeneration.

Embodiment 24. A compound for use according to any of embodiments 20 to 23 in free form or in pharmaceutically acceptable salt form wherein the tendon is the Achilles tendon.

Embodiment 25. A compound for use according to any of embodiments 20 to 23 in free form or in pharmaceutically acceptable salt form wherein the tendon is a rotator cuff tendon.

Embodiment 26. A compound according to any one of embodiments 1 to 16 in free form or in pharmaceutically acceptable salt form for use in the treatment of a ligament injury.

Embodiment 27. A compound for use according to embodiment 26 in free form or in pharmaceutically acceptable salt form wherein the ligament injury is a ligament partial rupture.

Embodiment 28. A compound for use according to embodiment 26 in free form or in pharmaceutically acceptable salt form wherein the ligament injury is a ligament full rupture.

Embodiment 29. A compound for use according to embodiment 26 in free form or in pharmaceutically acceptable salt form wherein the ligament injury is ligament degeneration.

Embodiment 30. A compound for use according to any of embodiment 19 to 29, wherein the compound is 4-(3-amino-1H-pyrazolo[4,3-b]pyridin-5-yl)-N-(3-hydroxy-3-(trifluoromethyl)cyclobutyl)-N,3-dimethylbenzenesulfonamide in free form or in pharmaceutically acceptable salt form.

Embodiment 31. A compound for use according to any of embodiment 19 to 29, wherein the compound is 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide in free form or in pharmaceutically acceptable salt form.

Embodiment 32. A compound for use according to any of embodiment 19 to 29, wherein the compound is 4-(3-amino-1H-pyrazolo[4,3-b]pyridin-5-yl)-3-chloro-N-(2-hydroxycyclopentyl)benzenesulfonamide in free form or in pharmaceutically acceptable salt form.

Embodiment 33. A compound for use according to any of embodiment 19 to 29, wherein the compound is 4-(3-amino-1H-pyrazolo[4,3-b]pyridin-5-yl)-3-chloro-N-((1R,2S)-2-hydroxycyclopentyl)benzenesulfonamide in free form or in pharmaceutically acceptable salt form.

Depending on the choice of the starting materials and procedures, the compounds can be present, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula (I), (II) or (III) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds of formula (I), (II) or (III) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}V$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington The Science and Practice of Pharmacy, $22^{nd}$ Ed. Pharmaceutical Press, 2013, pp. 1049-1070). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, ameliorate symptoms, alleviate conditions.

As used herein, the term "subject" refers to a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound.

In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Typically, the compounds of formula (I) can be prepared according to the Schemes provided infra.

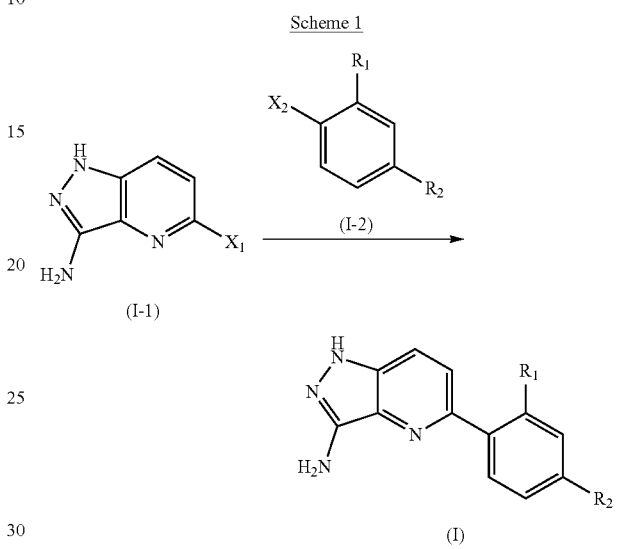

A compound of formula (I) wherein $R_1$ and $R_2$ are as defined herein can be prepared according to Scheme 1 by coupling a compound of formula (I-1) wherein $X_1$ is a halogen, e.g. chloro, with a compound of formula (I-2) wherein $R_1$ and $R_2$ are as defined herein in relation to a compound of formula (I) and $X_2$ is a halogen or a boronic acid derivative in the presence of a suitable solvent, such as e.g. dioxane, acetonitrile, and a suitable catalyst, preferably a palladium-based catalyst, such as e.g. bis(triphenylphosphine)palladium(II) dichloride ($Pd(PPh_3)_2Cl_2$) or tetrakis(triphenylphosphine)palladium(0) ($Pd(Ph_3)_4$). When $X_2$ is a boronic acid derivative, such as e.g. boronic acid pinacolate, the coupling can be done in the presence of a base, such as e.g. sodium carbonate. When $X_2$ is a halogen, such as e.g. bromide, the coupling can be done in the presence of a stannane, such as e.g. hexamethylditin.

Compounds of formula (I-1) and (I-2) can be obtained as described in the schemes and examples further below.

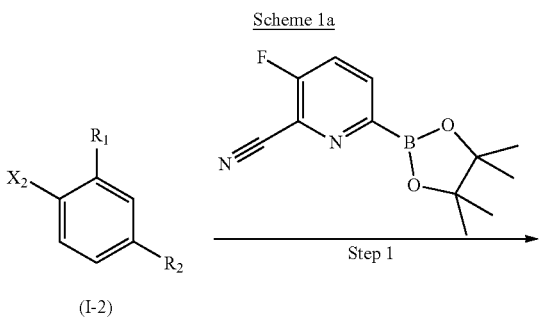

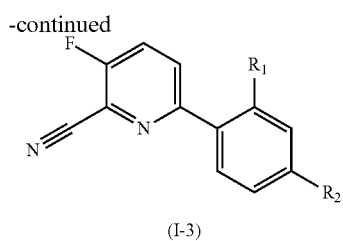

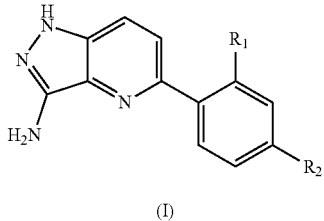

A compound of formula (I) wherein $R_1$ and $R_2$ are as defined herein can be prepared according to Scheme 1a by carrying out the following steps:

Step 1: A compound of formula (I-3) wherein $R_1$ and $R_2$ are as defined herein in relation to a compound of formula (I) can be obtained by coupling a compound of formula (I-2) wherein $R_1$ and $R_2$ are as defined herein in relation to a compound of formula (I) and wherein $X_2$ is a halogen, e.g. bromo, with 3-fluoro-6-(4,4,5,5-tetramethyl-1,3,2-dioxaborolan-2-yl)picolinonitrile in the presence of a suitable solvent, e.g. acetonitrile, a suitable base, e.g. potassium carbonate, and a suitable catalyst, e.g. [1,1'-bis(diphenylphosphino)ferrocene]palladium(II) dichloride ($PdCl_2$(dppf)).

Step 2: A compound of formula (I) wherein $R_1$ and $R_2$ are as defined herein can be obtained by treating a compound of formula (I-3) wherein $R_1$ and $R_2$ are as defined herein in relation to a compound of formula (I) with a hydrazine containing solution in a suitable solvent, e.g. ethanol. 3-fluoro-6-(4,4,5,5-tetramethyl-1,3,2-dioxaborolan-2-yl)picolinonitrile can be obtained as described in the schemes and examples further below.

Scheme 2

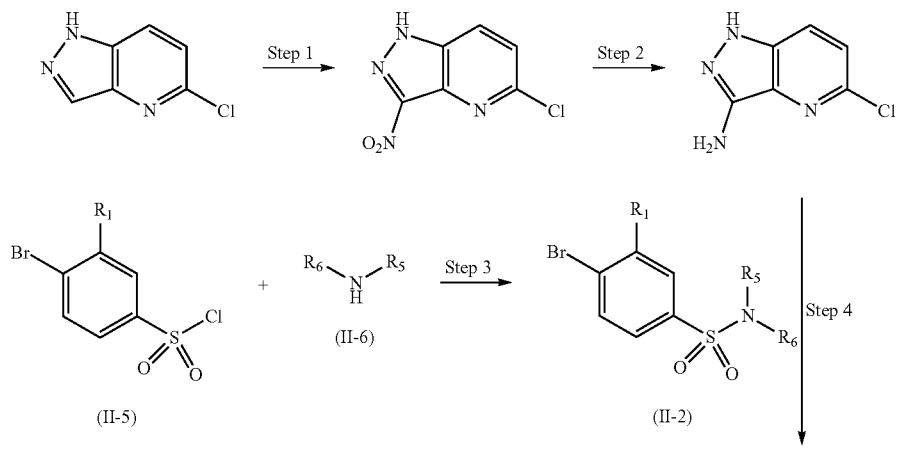

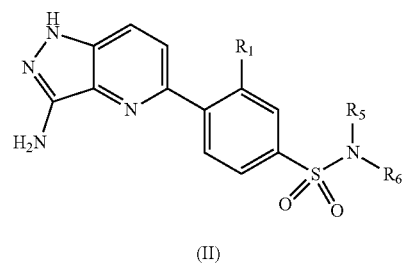

A compound of formula (II) wherein $R_1$, $R_5$ and $R_6$ are as defined herein can be prepared according to Scheme 2 by carrying out the following steps:

Step 1: 5-chloro-3-nitro-1H-pyrazolo[4,3-b]pyridine can be obtained by treating 5-chloro-1H-pyrazolo[4,3-b]pyridine with a nitrating agent such as e.g. nitric acid in the presence of a suitable acid, such as e.g. sulfuric acid.

Step 2: 5-chloro-1H-pyrazolo[4,3-b]pyridin-3-amine can be obtained by hydrogenation of 5-chloro-3-nitro-1H-pyrazolo[4,3-b]pyridine in the presence of a suitable hydrogenating agent, e.g. $H_2$, in the presence of a suitable catalyst, e.g. palladium on carbon, in a suitable solvent, e.g. methanol.

Step 3: A compound of formula (II-2) wherein $R_1$, $R_5$ and $R_6$ are as defined herein can be obtained by coupling a compound of formula (II-5) wherein $R_1$ is as defined herein with a compound of formula (II-6) wherein $R_5$ and $R_6$ are as defined herein in the presence of a suitable base, e.g. diisopropyl ethylamine, in a suitable solvent, e.g. dichloromethane or pyridine.

Step 4: 5-chloro-1H-pyrazolo[4,3-b]pyridin-3-amine is coupled to a compound of formula (II-2) wherein $R_1$, $R_5$ and $R_6$ are as defined herein in the presence of a stannane, such as e.g. hexamethylditin, in the presence of a suitable catalyst, such as e.g. tetrakis(triphenylphosphine)palladium(0) (Pd(Ph$_3$)$_4$), in the presence of a suitable solvent, e.g. dioxane, to give a compound of formula (II) wherein $R_1$, $R_5$ and $R_6$ are as defined herein.

Scheme 2a

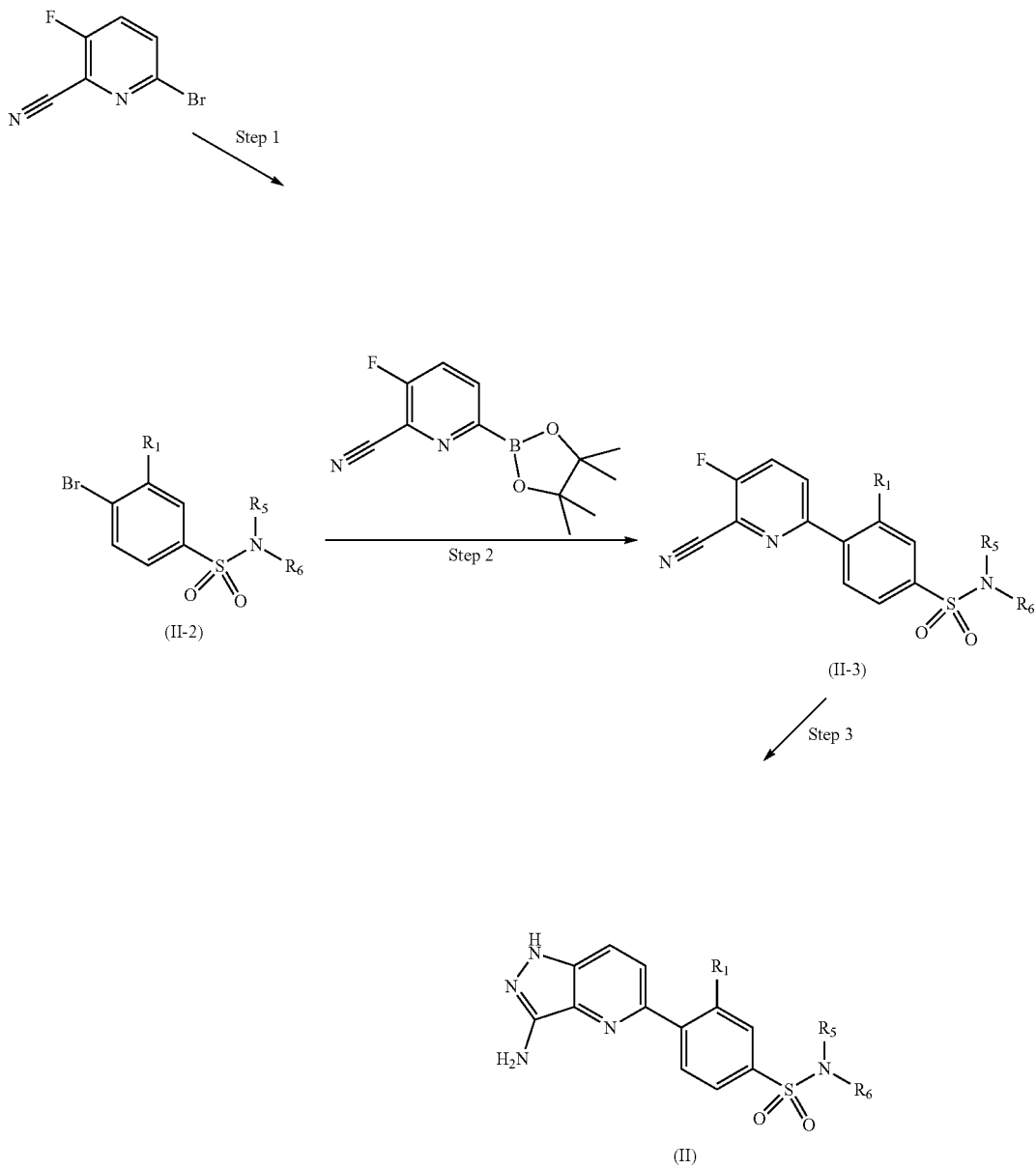

A compound of formula (II) wherein $R_1$, $R_5$ and $R_6$ are as defined herein can be prepared according to Scheme 2a by carrying out the following steps:

Step 1: 3-fluoro-6-(4,4,5,5-tetramethyl-1,3,2-dioxaborolan-2-yl)picolinonitrile can be obtained from 6-bromo-3-fluoropicolinonitrile in the presence of a boronating agent such as e.g. bis(pinacolato)diboron, in a suitable solvent, such as e.g. dioxane, in the presence of a suitable base, e.g. potassium acetate.

Step 2: A compound of formula (II-3) wherein $R_1$, $R_5$ and $R_6$ are as defined herein can be obtained by reacting 3-fluoro-6-(4,4,5,5-tetramethyl-1,3,2-dioxaborolan-2-yl)picolinonitrile with a compound of formula (II-2) wherein $R_1$, $R_5$ and $R_6$ are as defined herein (which can be obtained as described in scheme 2), in the presence of a suitable solvent, e.g. acetonitrile, a suitable base, e.g. potassium carbonate, and a suitable catalyst, e.g. [1,1'-Bis(diphenylphosphino)ferrocene]palladium(II) dichloride ($PdCl_2$(dppf)).

Step 3: A compound of formula (II) wherein $R_1$, $R_5$ and $R_6$ are as defined herein can be obtained by reacting a compound of formula (II-3) wherein $R_1$, $R_5$ and $R_6$ are as defined herein with a hydrazine containing solution in a suitable solvent, e.g. ethanol.

pound of formula (III-5) wherein $R_1$ is as defined herein, with a compound of formula (III-6) wherein $R_3$ is as defined herein in the presence of a suitable base, such as e.g. diisopropyl ethylamine, in a suitable solvent, such as e.g. dichloromethane or pyridine.

Step 2: A compound of formula (III-2) wherein $R_1$ and $R_3$ are as defined herein can be obtained by treating a compound of formula (III-2') wherein $R_1$ and $R_3$ are as defined herein with a suitable boronating agent, such as e.g. bis(pinacolato)diboron in the presence of a suitable base, such as e.g. potassium acetate, and a suitable catalyst such as e.g. tris(dibenzylideneacetone)dipalladium(0) ($Pd_2(dba)_3$) and a suitable ligand, such as e.g. tricyclohexylphosphine ($PCy_3$).

Step 3: A compound of formula (III) wherein $R_1$ and $R_3$ are as defined herein can be obtained by treating a compound of formula (III-2) wherein $R_1$ and $R_3$ are as defined herein with 5-chloro-1H-pyrazolo[4,3-b]pyridin-3-amine which can be obtained as described in Scheme 2, in the presence of a suitable base, such as e.g. sodium carbonate, and a suitable catalyst, such as e.g. bis(triphenylphosphine)palladium(II) dichloride ($Pd(PPh_3)_2Cl_2$), in a suitable solvent, such as e.g. acetonitrile.

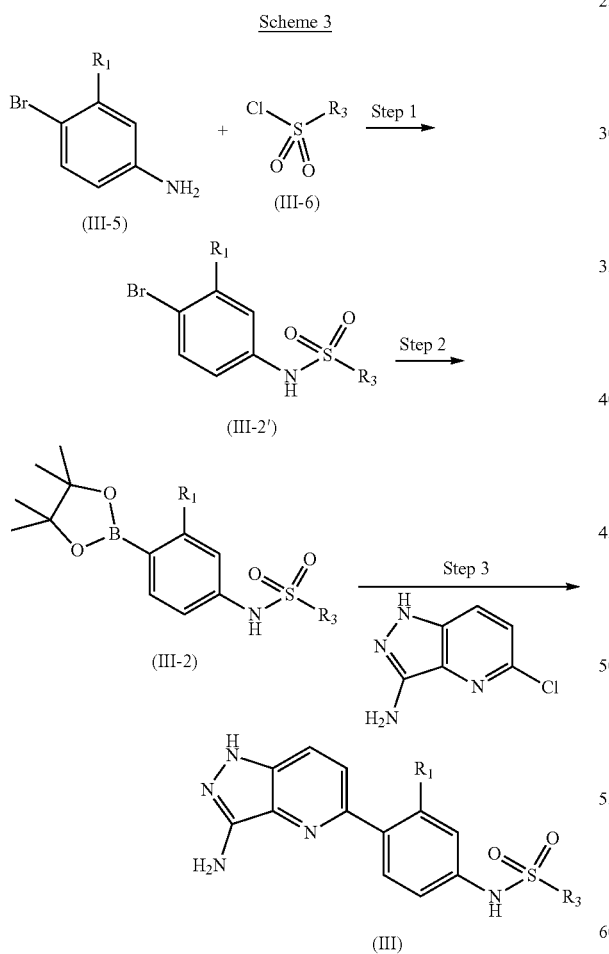

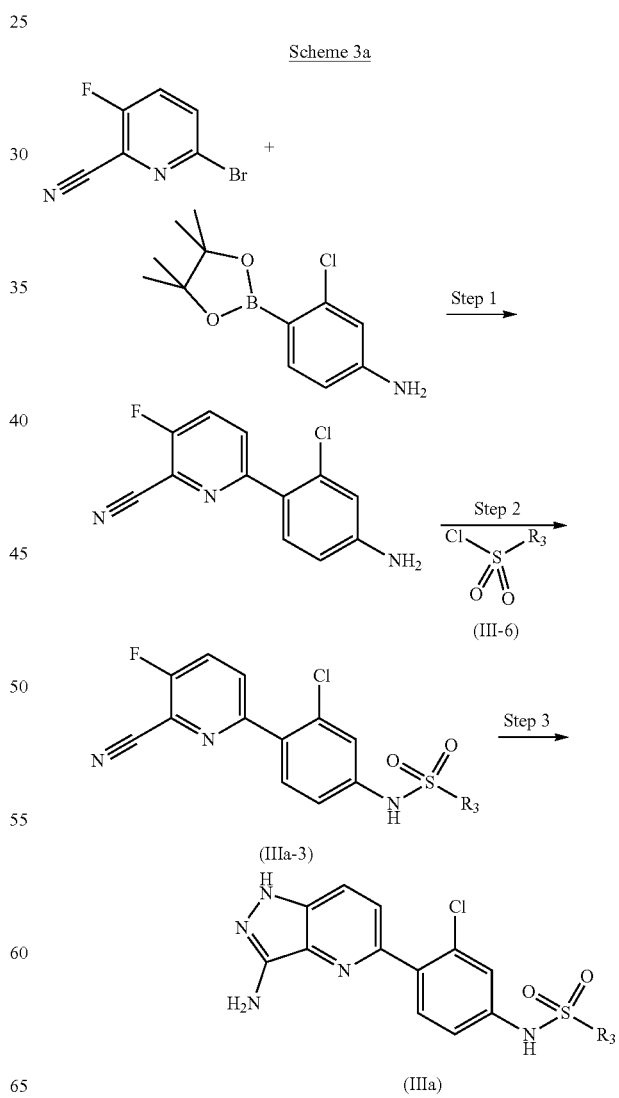

A compound of formula (III) wherein $R_1$ and $R_3$ are as defined herein can be prepared according to Scheme 3 by carrying out the following steps:

Step 1: A compound of formula (III-2') wherein $R_1$ and $R_3$ are as defined herein can be obtained by coupling a com- A compound of formula (IIIa) wherein $R_3$ is as defined herein can be prepared according to Scheme 3a by carrying out the following steps:

Step 1: 6-(4-amino-2-chlorophenyl)-3-fluoropicolinonitrile can be obtained by combining 6-bromo-3-fluoropicolinonitrile with 3-chloro-4-(4,4,5,5-tetramethyl-1,3,2-dioxaborolan-2-yl)aniline in the presence of a suitable solvent, e.g. acetonitrile, a suitable base, e.g. potassium carbonate, and a suitable catalyst, e.g. (1,1'-Bis(diphenylphosphino)ferrocene)palladium(II) dichloride (PdCl$_2$(dppf)).

Step 2: A compound of formula (IIIa-3) wherein $R_3$ is as defined herein can be obtained by treating 6-(4-amino-2-chlorophenyl)-3-fluoropicolinonitrile with a compound of formula (III-6) wherein $R_3$ is as defined herein in the presence of a suitable base, such as e.g. diisopropyl ethylamine, in a suitable solvent, such as e.g. dichloromethane or pyridine.

Step 3: A compound of formula (IIIa) wherein $R_3$ is as defined herein can be obtained by treating a compound of formula (IIIa-3) with a hydrazine containing solution in a suitable solvent, e.g. ethanol.

Scheme 3b

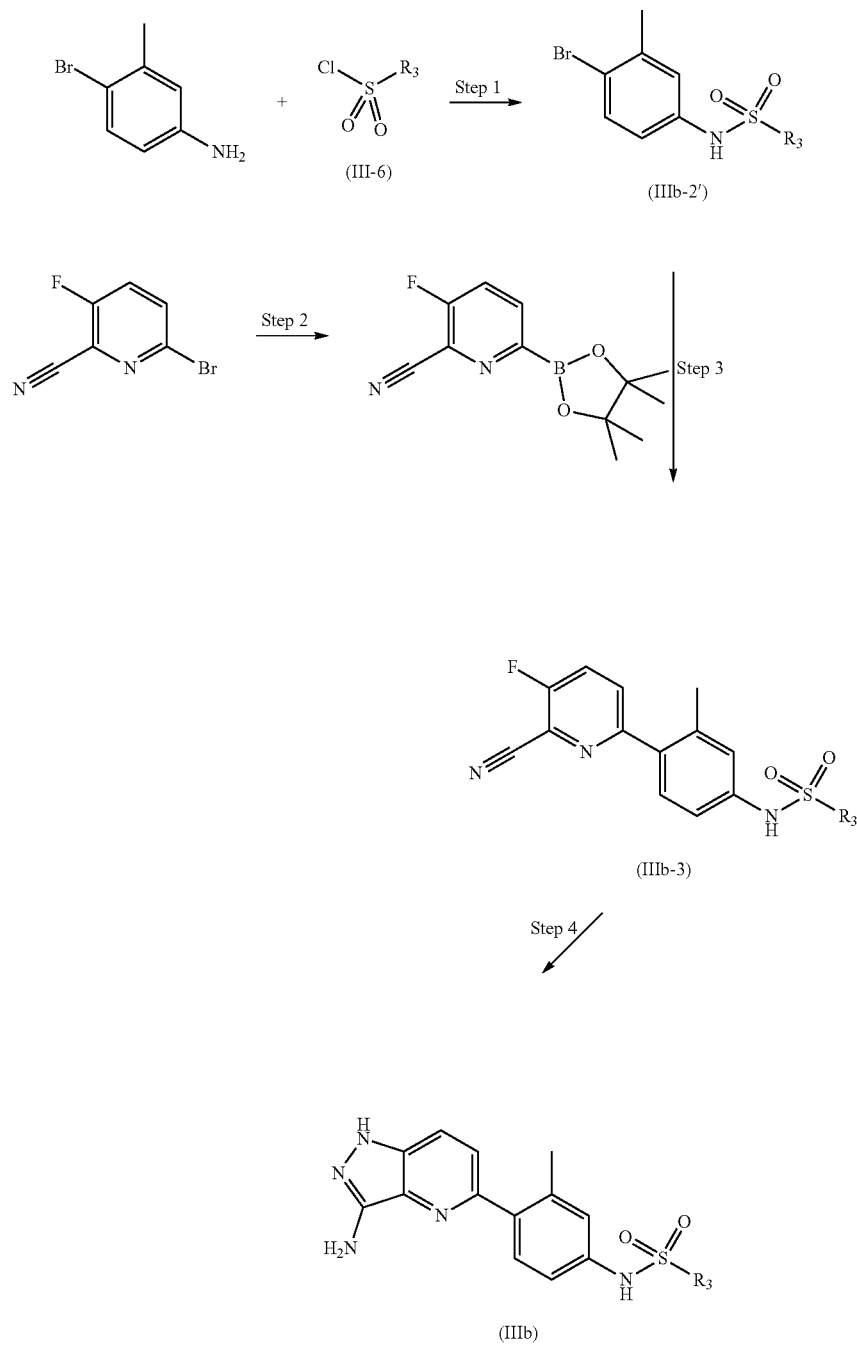

A compound of formula (IIIb) wherein $R_3$ is as defined herein can be prepared according to Scheme 3b by carrying out the following steps:

Step 1: A compound of formula (IIIb-2') wherein $R_3$ is as defined herein can be obtained by treating 4-bromo-3-methylaniline with a compound of formula (III-6) wherein $R_3$ is as defined herein in the presence of a suitable base, such as e.g. diisopropyl ethylamine, in a suitable solvent, such as e.g. dichloromethane or pyridine.

Step 2: 3-fluoro-6-(4,4,5,5-tetramethyl-1,3,2-dioxaborolan-2-yl)picolinonitrile can be obtained by treating 6-bromo-3-fluoropicolinonitrile with a suitable boronating agent, such as e.g. bis(pinacolato)diboron in the presence of a suitable base, such as e.g. potassium acetate, in a suitable solvent e.g. dioxane.

Step 3: A compound of formula (IIIb-3) wherein $R_3$ is as defined herein can be obtained by coupling 3-fluoro-6-(4,4,5,5-tetramethyl-1,3,2-dioxaborolan-2-yl)picolinonitrile with a compound of formula (IIIb-2') wherein $R_3$ is as defined herein in the presence of a suitable solvent, e.g. acetonitrile, a suitable base, e.g. potassium carbonate, and a suitable catalyst, e.g. [1,1'-Bis(diphenylphosphino)ferrocene]palladium(II) dichloride ($PdCl_2(dppf)$).

Step 4: A compound of formula (IIIb) wherein $R_3$ is as defined herein can be obtained by treating a compound of formula (IIIb-3) with a hydrazine containing solution in a suitable solvent, e.g. ethanol.

Compounds of formula (I-1), (I-3), (II-3), (IIIa-3), (IIIb-3) as defined herein are useful in the preparation of compounds of the invention, e.g., compounds of Formula (I). Thus, in an aspect, the invention relates to a compound of formula (I-1), (I-3), (II-3), (IIIa-3), (IIIb-3) or salts thereof. In another aspect, the invention relates to the use of a compound of formula (I-1), (I-3), (II-3), (IIIa-3), (IIIb-3) or salts thereof in the manufacture of a compound of formula (I).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In a further aspect, the invention relates to a process of making a process for the preparation of a compound of formula (I), in free form or in pharmaceutically acceptable salt form, comprising the steps of:

a) coupling a compound of formula (I-1) as defined herein with a compound of formula (I-2) to give a compound of formula (I) as defined herein;

b) recovering the so obtainable compound of formula (I) in free form or in pharmaceutically acceptable salt form.

In a further aspect, the invention relates to a process of making a process for the preparation of a compound of formula (I), in free form or in pharmaceutically acceptable salt form, comprising the steps of:

a) treating a compound of formula (I-3) as defined herein with hydrazine;

b) recovering the so obtainable compound of formula (I) in free form or in pharmaceutically acceptable salt form.

In another aspect, the present invention provides a pharmaceutical composition comprising a compound of the present invention in free form or in a pharmaceutically acceptable salt form, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration, such as peritendinous administration, intratendinous administration or transdermal administration. Certain injectable compositions are aqueous isotonic solutions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Sucrose acetate isobutyrate (SAIB) and ethanol may be used in injectable formulations comprising the compound of the invention.

The present invention relates also, in a further particular embodiment, to sustained release formulations in the form of microparticle formulations (especially for injection) comprising as active ingredient (drug substance) a compound of the formula (I), or a pharmaceutically-acceptable salt thereof, and one or more polylactide-co-glycolide polymers (PLGAs).

The drug substance is incorporated here into a biodegradable polymer matrix consisting of 2 or more different polylactide-co-glycolide polymers (PLGAs). The PLGAs have a lactide:glycolide monomer ratio of 100:0 to 0:100, preferably to 75:20 to 20:75, more preferably 50:50.

Preferably, the PLGA or PLGAs has or have a molecular weight in the range of about 10 to 70 kDa, Preferably, the microparticles formulation contains a copolymer of DL-lactide and glycolide in a 50:50 molar ratio up to 75:25 molar ratio with an inherent viscosity ranging from 0.15 to 0.60 dL/g with an ester or acid end group, either branched or linear or combination of both copolymers plus drug substance. The drug substance incorporated into the microparticles preferably ranges from 1 t0 25%, in particular from 2 to 10% (w/w). The microparticles are formulated to mean mass range in size preferably from 5 to 100, e.g. 5 to 25, microns. The population of microparticles is formulated to be delivered through 22 gauges or higher needles.

Additional excipients may be added to the microparticle formulations, such as, but not limited to, carboxymethylcellulose sodium, mannitol or ploxamer or combinations of two or all thereof, to achieve isotonicity and promote syringeability.

The microparticles formulation may be manufactured according to the following method steps (a) to (e):

(a) Dissolving drug substance in a poly(lactic-co-glycolic) acid copolymer organic solution comprising an organic solvent or solvent mixture to produce a drug solution;

(b) Treating the drug substance-PLGA solution to remove solvent so that it remains in an amount of 10,000 ppm or less, e.g. 100 to 5000 ppm, for example using a heating chamber; and emulsifying the resulting solution into micro-droplets by adding it into a water phase containing a proper emulsifier, such as polyvinyl alcohol, e.g. in an amount of from 0.5 to 2% by weight, such as 1% by weight;

(c) Preferably collecting the controlled- or sustained-release microparticles using a vacuumed filtration or preferably centrifugation;

(d) Preferably using a second drying step to remove residual solvents, especially freeze drying; and
(e) Preferably sieving the collected controlled- or sustained-release microparticles using a sieve, e.g. a 150 micron sieve.

Particular organic solvents used as primary solvents for preparation of microparticles in Step (a) are, for example, dichloromethane (DCM) and ethyl acetate (EA) either alone or in combination or in combination with methanol (MeOH) and/or dimethylsulfoxide (DMSO), for example, the volume share of DCM in DCM/EA mixture may range from 5% to 50%.

The compounds of formula (I) in free form or in pharmaceutically acceptable salt form, exhibit valuable pharmacological properties, e.g. inducing tendon markers such as scleraxis, tenomodulin and/or downstream extracellular matrix (ECM) genes such as collagen type 1a2 e.g. as indicated in the in vitro and ex vivo tests as provided in the examples, and are therefore indicated for therapy or for use as research chemicals, e.g. as tool compounds.

Particularly interesting compounds of the invention have good potency in the biological assays described herein. In another aspect, they should have a favourable safety profile. In another aspect, they should possess favourable pharmacokinetic properties. Furthermore, the ideal drug candidate will be in a form that is stable, non-hygroscopic and easily formulated.

It was found that the compounds of the invention have scleraxis inducing properties. Scleraxis is a tendon cell specific transcription factor. Based on the literature, scleraxis appears to act early in the tendon cell differentiation pathway, it is a marker of both tendon cell progenitors (tendon stem cells) and of maturing tenocytes in vivo. Thus, without wishing to be bound by theory, it is thought that these properties are indicative that the compounds of the invention can be useful in treating tendon and/or ligament injuries.

Induction of scleraxis can be measured by the in vitro and ex vivo assays described in the Examples.

Preferred compounds of the invention also have tenomodulin and collagen type I (Col1a2) inducing properties. Tenomodulin (Tnmd) genes have been shown to be enriched in tendon cells and associated with tenogenesis while an increase in tendon collagen type I (Col1a2) is secondary to tenogenic differentiation and is necessary for proper healing. Thus, without wishing to be bound by theory, it is thought that these properties are indicative that the compounds of the invention can be useful in treating tendon and/or ligament injuries.

Induction of tenomodulin and collagen type I (Col1a2) can be measured by the ex vivo assays described in the Examples.

Having regard to their activity as scleraxis inducers, compounds of the formula (I) in free or pharmaceutically acceptable salt form, are useful in the treatment of conditions which are responsive (meaning especially in a therapeutically beneficial way) to induction of scleraxis, such as tendon and/or ligament injuries.

Thus, the compounds of the invention may be useful in the treatment of tendon and/or ligament injury. They may be useful in the treatment of chronic tendon injury, which may lead to tendon degeneration. They may also be useful in the treatment of tendon degeneration. They may be useful in the treatment of acute tendon injury, such as tendon partial or full tear. They may be useful in the treatment of chronic ligament injury, which may lead to ligament degeneration. They may also be useful in the treatment of ligament degeneration. They may be useful in the treatment of acute ligament injury, such as ligament partial or full tear. Partial or full tear of tendons and ligaments can be determined by techniques known to the skilled person such as MRI (magnetic resonance imaging) or ultrasound.

Thus, as a further embodiment, the present invention provides the use of a compound of formula (I) or a pharmaceutically acceptable salt thereof, in therapy. In a further embodiment, the therapy is for a disease which may be treated by induction of scleraxis. In another embodiment, the disease is selected from the afore-mentioned list, suitably tendon and/or ligament injury, more suitably tendon and/or ligament partial rupture, tendon and/or ligament full rupture, tendon and/or ligament degeneration.

Tendon and ligament injuries can be identified by a skilled physician using techniques such as MRI (magnetic resonance imaging) and ultrasound.

Thus, as a further embodiment, the present invention provides a compound of formula (I) in free form or in pharmaceutically acceptable salt form for use in therapy. In a further embodiment, the therapy is for a disease which may be treated by induction of scleraxis. In another embodiment, the disease is selected from the afore-mentioned list, suitably tendon and/or ligament injury, more suitably tendon and/or ligament partial rupture, tendon and/or ligament full rupture or tendon and/or ligament degeneration.

In another embodiment, the invention provides a method of treating a disease which is treated by induction of scleraxis comprising administration of a therapeutically acceptable amount of a compound of formula (I) in free form or in pharmaceutically acceptable salt form. In a further embodiment, the disease is selected from the afore-mentioned list, suitably tendon and/or ligament injury, more suitably tendon and/or ligament partial rupture, tendon and/or ligament full rupture or tendon and/or ligament degeneration.

Thus, as a further embodiment, the present invention provides the use of a compound of formula (I) in free form or in pharmaceutically acceptable salt form, for the manufacture of a medicament. In a further embodiment, the medicament is for treatment of a disease which may be treated by induction of scleraxis. In another embodiment, the disease is selected from the afore-mentioned list, suitably tendon and/or ligament injury, more suitably tendon and/or ligament partial rupture, tendon and/or ligament full rupture or tendon and/or ligament degeneration.

In one embodiment of the present invention, there is provided 4-(3-amino-1H-pyrazolo[4,3-b]pyridin-5-yl)-N-(3-hydroxy-3-(trifluoromethyl)cyclobutyl)-N,3-dimethyl-benzenesulfonamide for use in the treatment of tendon injury.

In one embodiment of the present invention, there is provided 4-(3-amino-1H-pyrazolo[4,3-b]pyridin-5-yl)-N-(3-hydroxy-3-(trifluoromethyl)cyclobutyl)-N,3-dimethyl-benzenesulfonamide for use in the treatment of ligament injury.

In one embodiment of the present invention, there is provided 4-(3-amino-1H-pyrazolo[4,3-b]pyridin-5-yl)-N-(3-hydroxy-3-(trifluoromethyl)cyclobutyl)-N,3-dimethyl-benzenesulfonamide for use in the treatment of tendon partial rupture, tendon full rupture or tendon degeneration.

In one embodiment of the present invention, there is provided 4-(3-amino-1H-pyrazolo[4,3-b]pyridin-5-yl)-N-(3-hydroxy-3-(trifluoromethyl)cyclobutyl)-N,3-dimethylbenzenesulfonamide for use in the treatment of ligament partial rupture, ligament full rupture or ligament degeneration.

In one embodiment of the present invention, there is provided 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide for use in the treatment of tendon injury.

In one embodiment of the present invention, there is provided 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide for use in the treatment of ligament injury.

In one embodiment of the present invention, there is provided 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide for use in the treatment of tendon partial rupture, tendon full rupture or tendon degeneration.

In one embodiment of the present invention, there is provided 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide for use in the treatment of ligament partial rupture, ligament full rupture or ligament degeneration.

In one embodiment of the present invention, the tendon is the Achilles tendon. In another embodiment, the tendon is a rotator cuff tendon.

In addition, the compounds shown in Table 1 as inducers of scleraxis and other tendon-related genes (tenomodulin and collagen) may also be useful in the treatment of tendon and/or ligament injuries.

Thus, in an embodiment, the invention relates to a compound of Table 1 in free form or in pharmaceutically acceptable salt form for use in the treatment of tendon and/or ligament injury.

TABLE 1

| Structure | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK 1 (IC$_{50}$ uM) | JAK 2 (IC$_{50}$ uM) | JAK 3 (IC$_{50}$ uM) | TYK 2 (IC$_{50}$ uM) |
|---|---|---|---|---|---|---|---|---|
| *[cyclopentyl-pyrazole-pyrrolopyrimidine nitrile compound]* | 0.12 | 3.13 | 0.74 | 2.64 | 1E−3 | 2E−3 | 0.2 | 6E−3 |
| *[pyrrolopyridine-pyrimidine-trifluoroethyl amide compound]* | 0.03 | 1.65 | 1.77 | 0.88 | 0.02 | 0.13 | 0.01 | 1.5 |
| *[phenoxyethyl-pyrrolidine-pyrimidine-tert-butylsulfonamide compound]* | 0.62 | n.d. | n.d. | n.d. | 0.02 | 8E−3 | 1.5 | 0.31 |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK 1 (IC$_{50}$ uM) | JAK 2 (IC$_{50}$ uM) | JAK 3 (IC$_{50}$ uM) | TYK 2 (IC$_{50}$ uM) |
|---|---|---|---|---|---|---|---|---|
| *structure* | 0.12 | 3.92 | 3.27 | 4.67 | 0.02 | 0.02 | 0.21 | 0.03 |
| *structure* | 8E-3 | 3.37 | 3.30 | 2.61 | 2E-4 | 7E-4 | 0.06 | 2E-3 |
| *structure* | 2.06 | 5.65 | 3.82 | 3.97 | 4E-3 | 0.15 | 10 | 0.11 |
| *structure* | 1.42 | 3.56 | 3.69 | 3.62 | n.d. | n.d. | n.d. | n.d. |

TABLE 1-continued
| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK 1 (IC$_{50}$ uM) | JAK 2 (IC$_{50}$ uM) | JAK 3 (IC$_{50}$ uM) | TYK 2 (IC$_{50}$ uM) |
|---|---|---|---|---|---|---|---|---|
| 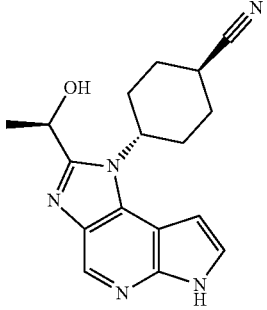 [SMILES: C[C@@H](O)c1nc2cnc3[nH]ccc3c2n1[C@H]1CC[C@H](C#N)CC1] | 2.69 | 4.27 | 6.38 | 6.62 | n.d. | n.d. | n.d. | n.d. |
| 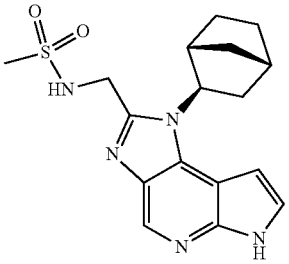 [SMILES: CS(=O)(=O)NCc1nc2cnc3[nH]ccc3c2n1[C@@H]1C[C@H]2CC[C@@H]1C2] | 0.18 | 3.22 | 4.57 | 3.76 | 1E−3 | 0.19 | 0.95 | 0.14 |
| 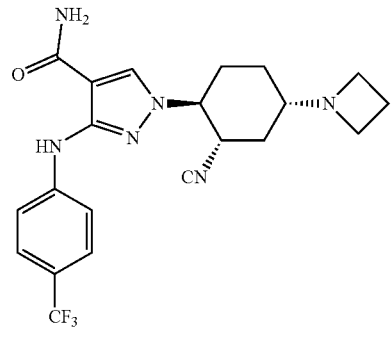 | 2.05 | 1.16 | 0.08 | 0.42 | 0.04 | 2.7 | 10 | 1.8 |
| 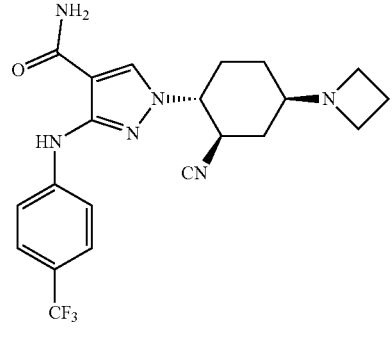 | 0.40 | 5.63 | 5.76 | 3.65 | 2E−3 | 0.24 | 10 | 0.12 |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK 1 (IC$_{50}$ uM) | JAK 2 (IC$_{50}$ uM) | JAK 3 (IC$_{50}$ uM) | TYK 2 (IC$_{50}$ uM) |
|---|---|---|---|---|---|---|---|---|
| [structure] | 0.22 | 5.77 | 1.31 | 0.90 | 1E−3 | 0.03 | 0.38 | 0.11 |
| [structure] | 1.24 | 0.85 | 4.83 | 0.94 | n.d. | n.d. | n.d. | n.d. |
| [structure] | 0.82 | 3.31 | 4.19 | 4.32 | n.d. | n.d. | n.d. | n.d. |
| [structure] | 0.02 | 0.36 | 5.99 | 0.40 | n.d. | n.d. | n.d. | n.d. |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK 1 (IC$_{50}$ uM) | JAK 2 (IC$_{50}$ uM) | JAK 3 (IC$_{50}$ uM) | TYK 2 (IC$_{50}$ uM) |
|---|---|---|---|---|---|---|---|---|
| | 0.51 | 0.47 | 0.08 | 1.15 | n.d. | n.d. | n.d. | n.d. |
| | 1.34 | 0.08 | 6.11 | 4.66 | n.d. | n.d. | n.d. | n.d. |
| | 4.32 | 5.34 | 6.93 | 5.01 | 0.05 | 0.46 | 9.4 | 0.78 |
| | 0.30 | 2.49 | 2.52 | 1.78 | 7E−4 | 0.004 | 0.25 | 0.03 |

TABLE 1-continued

| | Scx-Luc (EC$_{50}$ uM) | Ex vivo SCX (EC$_{50}$ uM) | Ex vivo Tnmd (EC$_{50}$ uM) | Ex vivo Col1a2 (EC$_{50}$ uM) | JAK 1 (IC$_{50}$ uM) | JAK 2 (IC$_{50}$ uM) | JAK 3 (IC$_{50}$ uM) | TYK 2 (IC$_{50}$ uM) |
|---|---|---|---|---|---|---|---|---|
| *[structure]* | 0.37 | 1.46 | 1.26 | 2.75 | 4E−3 | 0.03 | 0.02 | 0.23 |
| *[structure]* | 1.06 | 3.32 | 6.71 | 3.11 | n.d. | n.d. | n.d. | n.d. | n.d.: not determined

The compounds shown in Table 1 also exhibit biochemical activity as JAK1, JAK2, JAK3 and/or TYK2 inhibitors.

The assays used to measure JAK1, JAK2, JAK3 and/or TYK2 activity are described below:

A kinase selectivity panel which measures substrate peptide phosphorylation was set-up for recombinant human Jak1 (aa 866-1154), Jak2 (aa808-1132), Jak3 (aa811-1124) and Tyk2 (aa888-1187). The technology used for the described assay is based on the separation and quantification of substrate and product in an electrical field. In the course of the kinase reaction the peptide substrate is phosphorylated by a kinase. The transfer of a phosphate residue also causes the introduction of two additional negative charges and hence to a change in the net charge of the phospho-peptide compared to the unphosphorylated peptide. Due to this difference in charge the phosphorylated and unphosphorylated peptides migrate with different velocities in an electrical field.

In the applied method, this separation takes place inside a chip that contains a complex capillary system for simultaneous analysis of 12 samples ("12-sipper chip", Caliper Technologies Corp., Mountain View, USA). In order to allow the detection and quantification of the peptides in the capillary system, the peptides carry a fluorescent label (fluorescein). With this label the peptides can be quantified by fluorescence intensity through the instruments laser and detection system (LC3000, Caliper Life Sciences).

The assays were performed in 384-well, low volume microtiter assay plates in a final reaction volume of 9 ul. Dose-response curves were generated by incubating 3 nM of each kinase together with 2 uM of a fluorescently labeled substrate peptide specific for each enzyme (Jak1 and Jak3 substrate FITC-Ahx-KKSRGDYMTMQIG-NH2, Jak2 and Tyk2 substrate 5(6)-Carboxyfluorescein-Ahx-GGEEEEYFELVKKKK) in 50 mM Hepes pH 7.5, 0.02% Tween 20, 0.02% BSA, 1 mM DTT, 10 uM Na$_3$VO$_4$, 10 mM ß-Glycerolphosphate, specific concentrations of MgCl$_2$ (Jak1 12 mM, Jak2 and Tyk2 9 mM, Jak3 1.5 mM) and 45 uM ATP for 60 min at 30° C. in the presence or absence of compound diluted in DMSO. Kinase reaction were terminated by adding 15 ul STOP buffer (100 mM HEPES pH 7.5, 5% DMSO, 0.1% Caliper coating reagent, 10 mM EDTA, and 0.015% Brij35.

Plates with terminated kinase reactions were transferred to the Caliper LC3000 workstation (Caliper Technologies Corp., Mountain View, USA) for reading. The relative amount of phosphorylated peptide r, was calculated using the heights of the substrate peak, s, and the product peak, p: r=p/(p+s).

Having regard to their biochemical activity shown in Table 1, and without wishing to be bound by theory, it is hypothesized that inhibition of JAK1 and/or JAK2 and/or JAK3 and/or TYK2 may have a positive effect on tendon and/or ligament injury.

Therefore, in an embodiment, the invention relates to the use of a JAK1 inhibitor compound for the treatment of tendon injury.

In another embodiment, the invention relates to the use of a JAK1 inhibitor compound for the treatment of ligament injury.

In another embodiment, the invention relates to the use of a JAK2 inhibitor compound for the treatment of tendon injury.

In another embodiment, the invention relates to the use of a JAK2 inhibitor compound for the treatment of ligament injury.

In another embodiment, the invention relates to the use of a JAK3 inhibitor compound for the treatment of tendon injury.

In another embodiment, the invention relates to the use of a JAK3 inhibitor compound for the treatment of ligament injury.

In another embodiment, the invention relates to the use of a TYK2 inhibitor compound for the treatment of tendon injury.

In another embodiment, the invention relates to the use of a TYK2 inhibitor compound for the treatment of ligament injury.

In another embodiment, the invention relates to the use of a JAK1/TYK2 inhibitor compound for the treatment of tendon injury.

In another embodiment, the invention relates to the use of a JAK1/TYK2 inhibitor compound for the treatment of ligament injury.

Having regard to their known activity as JAK inhibitors, the following compounds shown in Table 2 may also be useful in the treatment of tendon and/or ligament injury. Thus, in an embodiment, the invention relates to a compound of Table 2 in free form or in pharmaceutically acceptable salt form for use in the treatment of tendon and/or ligament injury.

TABLE 2

| Compound | Structure |
|---|---|
| Upadacitinib | 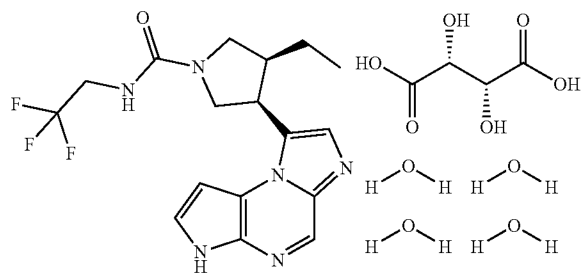 |
| ENMD-2076 ((E)-N-(5-Methyl-1H-pyrazol-3-yl)-6-(4-methylpiperazin-1-yl)-2-styrylpyrimidin-4-amine) | 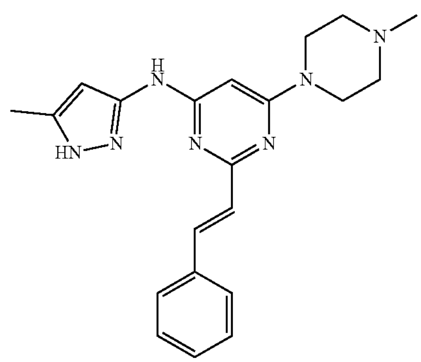 |
| JTE-052 (from company Japanese Tobacco International, LEO Pharma) International, LEO Pharma) | Structure unknown |
| R-333 (from Rigel) | Structure unknown |
| BMS-911543 (N,N-dicyclopropyl-4-((1,5-dimethyl-1H-pyrazol-3-yl)amino)-6-ethyl-1-methyl-1,6-dihydroimidazo[4,5-d]pyrrolo[2,3-b]pyridine-7-carboxamide | 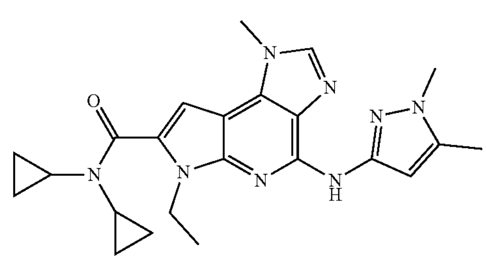 [SMILES: CCn1c(C(=O)N(C2CC2)C2CC2)cc2c3c(ncn3C)c(Nc3cc(C)n(C)n3)nc21] |

TABLE 2-continued

| Compound | Structure |
|---|---|
| gandotinib | 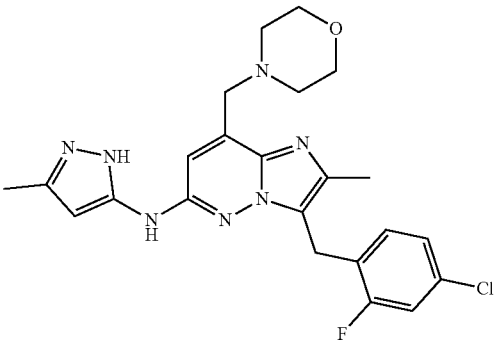 [SMILES: Cc1cc(Nc2cc(CN3CCOCC3)c3nc(C)c(Cc4ccc(Cl)cc4F)n3n2)[nH]n1] |
| PF-06263276 (from Pfizer) | Structure unknown |
| INCB-52793 (from Incyte) | Structure unknown |
| AC-410 ([(S)-(4-fluorophenyl)(4-((5-methyl-1H-pyrazol-3-yl)amino)quinazolin-2-yl)methanol]) | 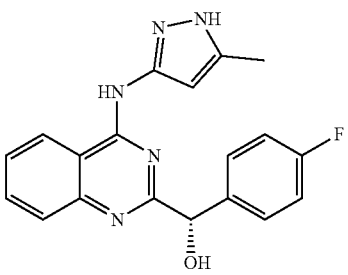 [SMILES: Cc1cc(Nc2nc([C@@H](O)c3ccc(F)cc3)nc3ccccc23)n[nH]1] |
| cerdulatinib | 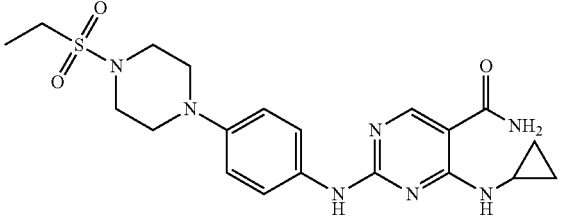 [SMILES: CCS(=O)(=O)N1CCN(c2ccc(Nc3ncc(C(N)=O)c(NC4CC4)n3)cc2)CC1] |
| TG-02, also known as SB-1317 from Tragara Pharmaceuticals | 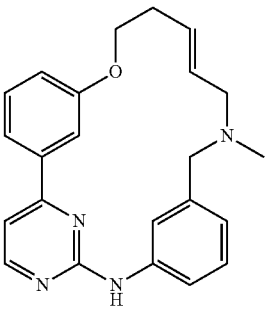 [SMILES: CN1C/C=C/CCOc2cccc(c2)-c2ccnc(n2)Nc2cccc(c2)C1] |
| LS-104 (from Aegera Therapeutics) | Structure unknown |
| peficitinib | Structure unknown |
| itacitinib | Structure unknown |
| R-348 (from Rigel) | Structure unknown |
| ganetespib | Structure unknown |

TABLE 2-continued

| Compound | Structure |
|---|---|
| lestaurtinib | (structure shown) |
| PF-04965842 (from Pfizer) | (structure shown) |
| ASN-002 (from Asana Biosciences) | Structure unknown |
| NS-018 (from Nippon Shinyaku) | Structure unknown |
| TD-1473 (from Theravance Biopharma) | Structure unknown |
| R-548 (from Aclaris) | Structure unknown |
| CT-1578 (from Cell Therapeutics) | Structure unknown |

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) in free form or in pharmaceutically acceptable salt form and at least one other therapeutic agent as a combined preparation for simultaneous, separate or sequential use in therapy. In one embodiment, the therapy is the treatment of tendon and/or ligament injury. Products provided as a combined preparation include a composition comprising the compound of formula (I) in free form or in pharmaceutically acceptable salt form and the other therapeutic agent(s) together in the same pharmaceutical composition, or the compound of formula (I) in free form or in pharmaceutically acceptable salt form and the other therapeutic agent(s) in separate form, e.g. in the form of a kit.

In one embodiment, the invention provides a pharmaceutical composition comprising a compound of formula (I) in free form or in pharmaceutically acceptable salt form and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I) in free form or in pharmaceutically acceptable salt form. In one embodiment, the kit comprises means for separately retaining said compositions, such as a container, divided bottle, or divided foil packet.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) in free form or in pharmaceutically acceptable salt form for treating tendon and/or ligament injury, wherein the medicament is prepared for administration with another therapeutic agent. The invention also provides the use of another therapeutic agent for tendon and/or ligament injury, wherein the medicament is administered with a compound of formula (I) in free form or in pharmaceutically acceptable salt form.

The invention also provides a compound of formula (I) in free form or in pharmaceutically acceptable salt form for use in a method of treating tendon and/or ligament injury, wherein the compound of formula (I) is prepared for administration with another therapeutic agent. The invention also provides another therapeutic agent for use in a method of treating tendon and/or ligament injury, wherein the other therapeutic agent is prepared for administration with a compound of formula (I) in free form or in pharmaceutically acceptable salt form. The invention also provides a compound of formula (I) for use in a method of treating tendon and/or ligament injury, wherein the compound of formula (I) is administered with another therapeutic agent. The invention also provides another therapeutic agent for use in a method of treating tendon and/or ligament injury, wherein the other therapeutic agent is administered with a compound of formula (I) in free form or in pharmaceutically acceptable salt form.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either peritendinously or intratendinously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

FIG. 1 shows a graphic representation of cumulative release of microparticle formulations of 4-(3-amino-1H-pyrazolo[4,3-b]pyridin-5-yl)-N-((1s,3s)-3-hydroxy-3-(trifluoromethyl)cyclobutyl)-3-methylbenzenesulfonamide over time in PBS buffer pH 7.4 (v/v), 1% Tween® 20, DL=drug Load.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

EXAMPLES

Abbreviations

δ chemical shift
ACN acetonitrile
aq. aqueous
API-MS atmospheric pressure ionization mass spectroscopy
cDNA complimentary deoxyribonucleic acid
Ct cycle threshold
DCM methylene chloride
DIPEA diisopropylethylamine
DMSO-$d_6$ dimethylsulfoxide-d6
EtOAc ethyl acetate
EtOH ethanol
ESI-MS electron-spray ionisation mass spectroscopy
FIA-MS flow injection analysis mass spectroscopy
h hour
HBSS Hank's Balanced Salt Solution
HPLC high performance liquid chromatography
$K_2CO_3$ potassium carbonate
KOAc potassium acetate
L liter
$LiAlH_4$ lithium aluminium hydride
LPM liters per minute
M molar
mg milligram
mM millimolar
MeOH methanol
min minute
mL milliliter
$MgSO_4$ magnesium sulfate
MHz megahertz
MSCGM Mesenchymal Stem Cell Growth Media
MW microwave
N normal
$Na_2SO_4$ sodium sulfate
$NaHCO_3$ sodium bicarbonate
NaOH sodium hydroxide
$NH_4Cl$ ammonium chloride
$NH_4OH$ ammonium hydroxide
NMR nuclear magnetic resonance
$PCy_3$ tricyclohexylphosphine
$PdCl_2$(dppf) [1,1'-bis(diphenylphosphino)ferrocene]dichloropalladium(II)
ppm parts per million
qPCR quantitative polymerase chain reaction
RNA ribonucleic acid
RT room temperature
SAIB sucrose acetate isobutyrate
sat. aq. saturated aqueous
Scx scleraxis
Scx-Luc scleraxis-luciferase
SFC supercritical fluid chromatography
TGFβ1 transforming growth factor-beta 1
THF tetrahydrofuran
$t_R$ retention time
UPLC-MS ultra high performance liquid chromatography mass spectroscopy
UPLC-MS
Column: Waters Acquity HSS T3, 1.8 μm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM ammonium acetate, B=acetonitrile+0.04% formic acid. Detection UV/VIS (DAD), ESI (+/−). Mass spectrometer range: 100-1200 Da.
Preparative HPLC (Method 1)
Gilson GX-281, pumps 331/332.
Column: Waters Sunfire C18, 30×100 mm, 5 μm. Flowrate 30 mL/min.
Mobile phase: Water+0.1% TFA and Acetonitrile.
Reverse Phase Column Chromatography (Method 2):
Teledyne ISCO CombiFlash
Column Redisep Rf Gold C18 High Performance, 15.5 g or 50 g pre-packed columns, 20-40 μm, 100A
Mobile phase: Water and Acetonitrile Preparative HPLC (Method 3)
Gilson GX-281, pumps 331/332.
Column: Dr Maisch Reprosil-Pur Basic C18 5 μm, 30×100 mm)
Mobile phase: Water (+7.3 mM NH$_4$OH) and Acetonitrile (+7.3 mM NH$_4$OH)
Preparative achiral SFC (Method 4)
Waters THAR SFC 100
Flowrate: 100 mL/min
Mobile phase: MeOH
NMR Measurements were performed on a Bruker Ultrashield Plus™ 400 (400 MHz) spectrometer using or not tetramethylsilane as an internal standard. Chemical shifts (d-values) are reported in ppm downfield from tetramethylsilane, spectra splitting pattern are designated as singlet (s), doublet (d), triplet (t), quartet (q), multiplet, unresolved or more overlapping signals (m), broad signal (br). Solvents are given in parentheses.

INTERMEDIATES

Intermediate 1a: 4-bromo-3-chloro-N-((1s,3s)-3-hydroxy-3-(trifluoromethyl)cyclobutyl)benzenesulfonamide A solution of 4-bromo-3-chlorobenzene-1-sulfonyl chloride (80 mg, 0.28 mmol) and (1s,3s)-3-amino-1-(trifluoromethyl)cyclobutan-1-ol hydrochloride (53 mg, 0.28 mmol) in DCM (2 mL) was stirred at 0° C. and DIPEA (0.15 mL, 0.83 mmol) was added. The reaction mixture was allowed to reach room temperature and stirred for 2 h, then partitioned between EtOAc and an sat. aq. NaHCO$_3$ solution. The aq. layer was extracted twice with EtOAc. The combined organic layers were washed with brine, dried over anhydrous MgSO$_4$, filtered and concentrated under reduced pressure. The crude material was purified by silica gel column chromatography (0 to 30% EtOAc in Cyclohexane) to give the title compound as a white solid. (UPLC-MS) $t_R$ 1.07 min; ESI-MS 408.0 [M−H]$^+$.

Intermediate 1b: 3-chloro-4-(6-cyano-5-fluoropyridin-2-yl)-N-((1s,3s)-3-hydroxy-3-(trifluoromethyl)cyclobutyl)benzenesulfonamide Step 1: A vial was charged with 6-bromo-3-fluoropicolinonitrile (48 mg, 0.24 mmol), bis(pinacolato)diboron (73 mg, 0.29 mmol), KOAc (47 mg, 0.48 mmol) and PdCl$_2$(dppf) (8.7 mg, 0.012 mmol). The vial was sealed, dioxane (4 mL) was added via syringe, and the reaction mixture was stirred at 80° C. for 1 h, cooled down to room temperature, diluted with DCM/EtOAc and passed through a pad of Celite. The pad was washed several times with EtOAc and MeOH. The combined filtrates were concentrated under reduced pressure to give crude 3-fluoro-6-(4,4,5,5-tetramethyl-1,3,2-dioxaborolan-2-yl)picolinonitrile.

Step 2: The crude material was diluted with ACN (4 mL) and treated with 4-bromo-3-chloro-N-((1s,3s)-3-hydroxy-3-(trifluoromethyl)cyclobutyl)benzenesulfonamide (Intermediate 1a, 103 mg, 0.24 mmol), K$_2$CO$_3$ (99 mg, 0.72 mmol), and PdCl$_2$(dppf) (8.7 mg, 0.012 mmol). The vial was sealed and irradiated in a microwave reactor at 120° C. for 30 min. The reaction was diluted with EtOAc and passed through a pad of Celite. The filtrate was washed with a sat. aq. NaHCO$_3$ solution, and the aq. layer was extracted twice with EtOAc. The combined organic layers were washed with brine, dried over anhydrous MgSO$_4$, filtered and concentrated under reduced pressure. The residue was purified by silica gel column chromatography (0 to 50% EtOAc in Cyclohexane) to give the title compound as an off-white solid. (UPLC-MS) $t_R$ 1.06 min; ESI-MS 448.0 [M−H]$^+$.

Intermediate 2a: 4-bromo-N-((1s,3s)-3-hydroxy-3-(trifluoromethyl)cyclobutyl)-3-methylbenzenesulfonamide A solution of (1s,3s)-3-amino-1-(trifluoromethyl)cyclobutan-1-ol hydrochloride (ActivateScientific, CAS Nr. 1408075-93-3) (249 mg, 1.30 mmol) in pyridine (6.5 ml) was treated with 4-bromo-3-methylbenzenesulfonyl chloride (Sigma-Aldrich, CAS Nr. 72256-93-0) (350 mg, 1.30 mmol) and stirred at 50° C. for 3 h. The reaction mixture was concentrated under reduced pressure and the resulting product was purified by silica gel column chromatography (0 to 100% EtOAc in hexanes) to afford the title compound. (UPLC-MS) $t_R$ 1.60 min; API-MS 387.9 [M+H]$^+$.

Intermediate 2b: 4-(6-cyano-5-fluoropyridin-2-yl)-N-((1s,3s)-3-hydroxy-3-(trifluoromethyl)cyclobutyl)-3-methyl benzenesulfonamide The title compound was prepared in an analogous manner to 3-chloro-4-(6-cyano-5-fluoropyridin-2-yl)-N-((1s,3s)-3-hydroxy-3-(trifluoromethyl)cyclobutyl)benzenesulfonamide (Intermediate 1 b) using 4-bromo-N-((1s,3s)-3-hydroxy-3-(trifluoromethyl)cyclobutyl)-3-methylbenzenesulfonamide (Intermediate 2a) to give the title compound. (UPLC-MS) $t_R$ 1.52 min; API-MS 430.2 [M+H]$^+$.

Intermediate 3a: 6-(4-amino-2-chlorophenyl)-3-fluoropicolinonitrile

A MW vial was charged with 6-bromo-3-fluoropicolinonitrile (Enamine, CAS Nr. 1256788-71-2) (1 g, 4.98 mmol), 3-chloro-4-(4,4,5,5-tetramethyl-1,3,2-dioxaborolan-2-yl)aniline (abcr, CAS Nr. 877160-63-9) (1.514 g, 5.97 mmol) and PdCl$_2$(dppf) (0.182 g, 0.249 mmol). ACN (20 mL) and aq. K$_2$CO$_3$ 2M (7.46 mL, 14.93 mmol) were added and the mixture was submitted to MW irradiations for 30 min at 120° C. The reaction was diluted with EtOAc and passed through a pad of Celite. The organic layer was washed with a sat. aq. NaHCO$_3$ solution. The aq. layer was back-extracted twice with EtOAc. The combined organic layers were washed with brine, dried over anhydrous MgSO$_4$, filtered and concentrated under reduced pressure. The residue was purified by silica gel column chromatography (0% to 25% EtOAc in Cylohexane) to afford the title product as a beige solid. (UPLC-MS) $t_R$ 0.97 min; ESI-MS 248.1 [M+H]$^+$; ESI-MS 246.0 [M−H]$^-$.

Intermediate 3b: 4-chloro-N-(3-chloro-4-(6-cyano-5-fluoropyridin-2-yl)phenyl)benzenesulfonamide To a sealed vial containing a stirring solution of 4-chlorobenzene-1-sulfonyl chloride (54 mg, 0.256 mmol) in Pyridine (0.5 mL) cooled down to 0° C. was added dropwise a solution of 6-(4-amino-2-chlorophenyl)-3-fluoropicolinonitrile (Intermediate 3a, 57 mg, 0.230 mmol) in Pyridine (1 mL). The reaction was stirred at 0° C. for 3 h. The reaction was diluted with EtOAc and washed twice with an aq. 1N NH$_4$Cl solution, water and brine. The organic layer was dried over anhydrous MgSO$_4$, filtered and concentrated under reduced pressure. The residue was purified by silica gel column chromatography (0% to 30% EtOAc in Cyclohexane) to afford the title product as an off white solid. (UPLC-MS) $t_R$ 1.18 min; ESI-MS 422.0/424.0 [M+H]⁺; ESI-MS 420.0/422.0 [M−H]⁻.

Intermediate 4a: 4-bromo-3-chloro-N-(3,3-difluoro-cyclobutyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 3,3-difluorocyclobutanamine to give the title compound as a colorless solid. (UPLC-MS) $t_R$ 1.03 min; ESI-MS 356.0 [M+H]⁺.

Intermediate 4b: 3-chloro-4-(6-cyano-5-fluoropyridin-2-yl)-N-(3,3-difluorocyclobutyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(3,3-difluorocyclobutyl)benzenesulfonamide (Intermediate 4a) to give the title compound. (UPLC-MS) $t_R$ 1.09 min; ESI-MS 400.1 [M−H]⁺.

Intermediate 5b: N-(3-chloro-4-(6-cyano-5-fluoropyridin-2-yl)phenyl)-4-methoxybenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 4-methoxybenzene-1-sulfonyl chloride and 6-(4-amino-2-chlorophenyl)-3-fluoropicolinonitrile (Intermediate 3a) at RT for 45 h without extracting workup to afford the title compound as a white solid. (UPLC-MS) $t_R$ 1.11 min; ESI-MS 418.1 [M+H]⁺; ESI-MS 416.1 [M−H]⁻.

Intermediate 6b: N-(3-chloro-4-(6-cyano-5-fluoropyridin-2-yl)phenyl)-4-fluorobenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 4-fluorobenzenesulfonyl chloride (Sigma-Aldrich, CAS Nr. 349-88-2) and 6-(4-amino-2-chlorophenyl)-3-fluoropicolinonitrile (Intermediate 3a) to afford the title compound as an off-white solid. (UPLC-MS) $t_R$ 1.12 min; ESI-MS 406.1 [M+H]⁺; ESI-MS 404.1 [M−H]⁻.

Intermediate 7a: 4-bromo-3-chloro-N-((1R,2S)-2-hydroxycyclopentyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1S,2R)-2-aminocyclopentan-1-ol to afford the title compound as a colorless solid. (UPLC-MS) $t_R$ 1.03 min; ESI-MS 356.0 [M+H]⁺.

Intermediate 7b: 3-chloro-4-(6-cyano-5-fluoropyridin-2-yl)-N-((1R,2S)-2-hydroxycyclopentyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1R,2S)-2-hydroxycyclopentyl)benzenesulfonamide (Intermediate 7a) to give the title compound as an off-white solid. (UPLC-MS) $t_R$ 1.00 min; ESI-MS 396.2 [M+H]⁺.

Intermediate 8a: 4-bromo-N-(3,3-difluorocyclobutyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and 3,3-difluorocyclobutanamine to give the title compound as a colorless solid. (UPLC-MS) $t_R$ 1.11 min; ESI-MS 340.0 [M−H]⁺.

Intermediate 8b: 4-(6-cyano-5-fluoropyridin-2-yl)-N-(3,3-difluorocyclobutyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-(3,3-difluorocyclobutyl)-3-methyl benzenesulfonamide (Intermediate 8a) to give the title compound. (UPLC-MS) $t_R$ 1.06 min; ESI-MS 380.1 [M−H]⁺.

Intermediate 9a: 4-bromo-N-((1s,3s)-3-hydroxy-3-(trifluoromethyl)cyclobutyl)-N,3-dimethylbenzenesulfonamide To a solution of 4-bromo-3-methylbenzene-1-sulfonyl chloride (1.32 g, 4.90 mmol) and (1s,3s)-3-(methylamino)-1-(trifluoromethyl)cyclobutanol (Intermediate 9c, 828 mg, 4.90 mmol) in DCM (20 mL) was added DIPEA (2.57 mL, 14.7 mmol). The reaction mixture was stirred for 40 min, then partitioned between EtOAc and an sat. aq. NaHCO₃ solution. The aq. layer was extracted twice with EtOAc. The combined organic layers were washed with brine, dried over anhydrous MgSO₄, filtered and concentrated under reduced pressure. The crude material was purified by silica gel column chromatography (0 to 100% EtOAc in Cyclohexane) to give the title compound as a colorless solid. (UPLC-MS) $t_R$ 1.13 min; ESI-MS 402.1/404.1 [M+H]⁺.

Intermediate 9b: 4-(6-cyano-5-fluoropyridin-2-yl)-N-((1s,3s)-3-hydroxy-3-(trifluoromethyl)cyclobutyl)-N,3-dimethylbenzenesulfonamide Step 1: A vial was charged with 6-bromo-3-fluoropicolinonitrile (435 mg, 2.16 mmol), bis(pinacolato)diboron (659 mg, 2.60 mmol), KOAc (425 mg, 4.33 mmol) and PdCl₂(dppf) (79 mg, 0.108 mmol). The vial was sealed, dioxane (3.75 mL) was added via syringe, and the reaction mixture was stirred at 80° C. for 1 h, cooled down to room temperature and filtered through Celite. The Celite pad was washed with MeOH. The combined filtrates were concentrated under reduced pressure to give crude 3-fluoro-6-(4,4,5,5-tetramethyl-1,3,2-dioxaborolan-2-yl)picolinonitrile.

Step 2: The crude material was diluted with ACN (15 mL) and treated with 4-bromo-N-((1s,3s)-3-hydroxy-3-(trifluoromethyl)cyclobutyl)-N,3-dimethylbenzenesulfonamide (Intermediate 9a, 871 mg, 2.16 mmol), K₂CO₃ (897 mg, 6.49 mmol), and PdCl₂(dppf) (79 mg, 0.108 mmol). The vial was sealed and irradiated in a microwave reactor at 120° C. for 30 min. The reaction was treated with water and EtOAc.

After phase separation the aq. layer was extracted twice with EtOAc. The combined organic layers were dried over anhydrous MgSO$_4$, filtered and concentrated under reduced pressure. The residue was purified by silica gel column chromatography (0 to 100% EtOAc in Cyclohexane) to give the title compound as an off-white solid. (UPLC-MS) $t_R$ 1.08 min; ESI-MS 461.1 [M+H$_2$O+H]$^+$.

Intermediate 9c: (1s,3s)-3-(methylamino)-1-(trifluoromethyl)cyclobutan-1-ol

To a solution of (1s,3s)-3-amino-1-(trifluoromethyl)cyclobutan-1-ol (324 mg, 1.69 mmol) and DIPEA (0.86 ml, 5.07 mmol) in THF (15 mL) was added methyl carbonochloridate (0.26 mL, 3.38 mmol). The reaction mixture was stirred at room temperature for 18 h and treated with LiAlH$_4$ (1M in THF, 8.46 mL, 8.46 mmol) at 0° C. under an argon atmosphere, then stirred at 60° C. for 5 h. The reaction mixture was quenched with water and aq. 1N NaOH, extracted with EtOAc, dried over Na$_2$SO$_4$, filtered, and concentrated under reduced pressure to afford the title compound which was used without further purification. FIA-MS (ES) 170.1 [M+H]$^+$.

Intermediate 10b: N-(3-chloro-4-(6-cyano-5-fluoropyridin-2-yl)phenyl)-3,4-difluorobenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3,4-difluorobenzene-1-sulfonyl chloride and 6-(4-amino-2-chlorophenyl)-3-fluoropicolinonitrile (Intermediate 3b) at 0° C. for 2 h without extracting workup to afford the title compound as a white solid. (UPLC-MS) $t_R$ 1.17 min; ESI-MS 424.2 [M+H]$^+$; ESI-MS 422.1 [M−H]$^−$.

Intermediate 11b: N-(3-chloro-4-(6-cyano-5-fluoropyridin-2-yl)phenyl)benzo[d][1,3]dioxole-5-sulfonamide The title compound was prepared in an analogous manner to 4-chloro-N-(3-chloro-4-(6-cyano-5-fluoropyridin-2-yl)phenyl)benzenesulfonamide (Intermediate 3b) using benzo[d][1,3]dioxole-5-sulfonyl chloride and 6-(4-amino-2-chlorophenyl)-3-fluoropicolinonitrile (Intermediate 3a) at 0° C. for 2.5 h to afford the title compound as white solid. (UPLC-MS) $t_R$ 1.09 min; ESI-MS 432.1 [M+H]$^+$; ESI-MS 430.1 [M−H]$^−$.

Intermediate 12a: 4-bromo-3-chloro-N-(2-hydroxycyclohexyl)benzenesulfonamide

The title compound was prepared in an analogous manner to 4-bromo-3-chloro-N-((1s,3s)-3-hydroxy-3-(trifluoromethyl)cyclobutyl)benzenesulfonamide (Intermediate 1a) using 2-aminocyclohexanol to give the title compound as a colorless solid (UPLC-MS) $t_R$ 1.08 min; ESI-MS 366.0/368.0/370.0 [M−H]$^−$.

Intermediate 12b: 3-chloro-4-(6-cyano-5-fluoropyridin-2-yl)-N-(2-hydroxycyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(2-hydroxycyclohexyl)benzenesulfonamide (Intermediate 12a) to give the title compound. (UPLC-MS) $t_R$ 1.05 min; ESI-MS 410.2 [M+H]$^+$.

Intermediate 13b: 4-chloro-N-(3-chloro-4-(6-cyano-5-fluoropyridin-2-yl)phenyl)-3-fluorobenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 4-chloro-3-fluorobenzene-1-sulfonyl chloride and 6-(4-amino-2-chlorophenyl)-3-fluoropicolinonitrile (Intermediate 3a) at 0° C. for 1.5 h to afford the title compound as an off-white solid. (UPLC-MS) $t_R$ 1.20 min; ESI-MS 440.0/442.0 [M+H]$^+$; ESI-MS 438./440.0 [M−H]$^−$.

Intermediate 15b: N-(3-chloro-4-(6-cyano-5-fluoropyridin-2-yl)phenyl)cyclohexanesulfonamide The title compound was prepared in an analogous manner to 4-chloro-N-(3-chloro-4-(6-cyano-5-fluoropyridin-2-yl)phenyl)benzenesulfonamide (Intermediate 3b) using an large excess of cyclohexanesulfonyl chloride (5 eq) and 6-(4-amino-2-chlorophenyl)-3-fluoropicolinonitrile (Intermediate 3a) at RT overnight to complete the reaction. Two purifications using silica gel column chromatography (0 to 30% EtOAc in Cyclohexane) afforded the title compound as a pale yellow solid. (UPLC-MS) $t_R$ 1.18 min; ESI-MS 394.1 [M+H]$^+$; ESI-MS 392.2 [M−H]$^−$.

Intermediate 16a: 4-bromo-3-methyl-N-phenylbenzenesulfonamide

The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and aniline to give the title compound as a colorless solid. (UPLC-MS) $t_R$ 1.15 min; ESI-MS 328.0 [M+H]$^+$.

Intermediate 16b: 4-(6-cyano-5-fluoropyridin-2-yl)-3-methyl-N-phenylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-methyl-N-phenylbenzenesulfonamide (Intermediate 16a) to give the title compound that was used as a crude material without purification. (UPLC-MS) $t_R$ 1.11 min; ESI-MS 366.2 [M−H]$^−$.

Intermediate 17b: N-(3-chloro-4-(6-cyano-5-fluoropyridin-2-yl)phenyl)-2-hydroxycyclohexane-1-sulfonamide The title compound was prepared in an analogous manner to 4-chloro-N-(3-chloro-4-(6-cyano-5-fluoropyridin-2-yl)phenyl)benzenesulfonamide (Intermediate 3b) using a large excess of 2-hydroxycyclohexane-1-sulfonyl chloride (3 eq) and 6-(4-amino-2-chlorophenyl)-3-fluoropicolinonitrile (Intermediate 3a) to afford the title compound as a white solid. (UPLC-MS) $t_R$ 1.07 min; ESI-MS 410.1 [M+H]$^+$; ESI-MS 408.1 [M−H]$^−$.

Intermediate 18a: (S)-(1-((4-bromo-3-chlorophenyl)sulfonyl)-4,4-difluoropyrrolidin-2-yl)methanol The title compound was prepared in an analogous manner to 4-bromo-N-(3-hydroxy-3-(trifluoromethyl)cyclobutyl)-3-methylbenzenesulfonamide (Intermediate 2a) using (S)-(4,4-difluoropyrrolidin-2-yl)methanol and 4-bromo-3-chlorobenzene-1-sulfonyl chloride to give the title compound. (UPLC-MS) $t_R$ 1.56 min; API-MS m/z: 390.0 [M+H]$^+$.

Intermediate 18b: (S)-6-(2-chloro-4-((4,4-difluoro-2-(hydroxymethyl)pyrrolidin-1-yl)sulfonyl)phenyl)-3-fluoropicolinonitrile The title compound was prepared in an analogous manner to 4-(6-cyano-5-fluoropyridin-2-yl)-N-(3-hydroxy-3-(trifluoromethyl)cyclobutyl)-3-methylbenzenesulfonamide (Intermediate 2b) using (S)-(1-((4-bromo-3-chlorophenyl)sulfonyl)-4,4-difluoropyrrolidin-2-yl)methanol (Intermediate 18a) to give the title compound. (UPLC-MS) $t_R$ 1.51 min; API-MS 432.1 [M+H]$^+$.

Intermediate 19a: 4-bromo-N-((1R,3S)-3-hydroxycyclopentyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1R,3S)-3-aminocyclopentanol to give the title compound as a colorless solid. (UPLC-MS) $t_R$ 0.90 min; ESI-MS 334.0 [M–H]$^-$.

Intermediate 19b: 4-(6-cyano-5-fluoropyridin-2-yl)-N-((1R,3S)-3-hydroxycyclopentyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4 bromo-N-((1R,3S)-3-hydroxycyclopentyl)-3-methylbenzenesulfonamide (Intermediate 19a) to give the title compound. (UPLC-MS) $t_R$ 0.89 min; ESI-MS 374.2 [M–H]$^-$.

Intermediate 20a: 4-bromo-N-((1R,2S)-2-hydroxycyclopentyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1S,2R)-2-aminocyclopentanol to give the title compound as a colorless solid. (UPLC-MS) $t_R$ 1.01 min; ESI-MS 334.1/336.0 [M+H]$^+$.

Intermediate 20b: 4-(6-cyano-5-fluoropyridin-2-yl)-N-((1R,2S)-2-hydroxycyclopentyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-((1R,2S)-2-hydroxycyclopentyl)-3-methylbenzenesulfonamide (Intermediate 20a) to give the title compound. (UPLC-MS) $t_R$ 0.96 min; ESI-MS 376.1 [M+H]$^+$.

Intermediate 21a: 2-((4-bromo-3-methylphenyl)sulfonyl)octahydrocyclopenta[c]pyrrole The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and octahydrocyclopenta[c]pyrrole to give the title compound as a colorless solid. (UPLC-MS) $t_R$ 1.33 min; ESI-MS 344.1/346.2 [M+H]$^+$.

Intermediate 21b: 3-fluoro-6-(4-((hexahydrocyclopenta[c]pyrrol-2(1H)-yl)sulfonyl)-2-methylphenyl)picolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 2-((4-bromo-3-methylphenyl)sulfonyl)octahydrocyclopenta[c]pyrrole (Intermediate 21a) to give the title compound. (UPLC-MS) $t_R$ 1.24 min; ESI-MS 386.2 [M+H]$^+$.

Intermediate 22b: N-(3-chloro-4-(6-cyano-5-fluoropyridin-2-yl)phenyl)-3-cyanobenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-cyanobenzene-1-sulfonyl chloride and 6-(4-amino-2-chlorophenyl)-3-fluoropicolinonitrile (Intermediate 3a) at 0° C. for 2 h without extracting workup to afford the title compound as a white solid. (UPLC-MS) $t_R$ 1.08 min; ESI-MS 413.1 [M+H]$^+$; ESI-MS 411.1 [M–H]$^-$.

Intermediate 23a: 4-bromo-3-chloro-N-((1R,3S)-3-hydroxycyclopentyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1R,3S)-3-aminocyclopentanol to give the title compound as a colorless solid. (UPLC-MS) $t_R$ 0.92 min; ESI-MS 354.2 [M+H]$^+$.

Intermediate 23b: 3-chloro-4-(6-cyano-5-fluoropyridin-2-yl)-N-((1R,3S)-3-hydroxycyclopentyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1R,3S)-3-hydroxycyclopentyl)benzenesulfonamide (Intermediate 23a) to give the title compound. (UPLC-MS) $t_R$ 0.93 min; ESI-MS 394.1 [M+H]$^+$.

Intermediate 24a: 4-bromo-3-chloro-N-(4,4-dimethylcyclohexyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4,4-dimethylcyclohexanamine to give the title compound as a colorless solid. (UPLC-MS) $t_R$ 1.36 min; ESI-MS 380.0 [M–H]$^-$.

Intermediate 24b: 3-chloro-4-(6-cyano-5-fluoropyridin-2-yl)-N-(4,4-dimethylcyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using 4-bromo-3-chloro-N-(4,4-dimethylcyclohexyl)benzenesulfonamide (Intermediate 24a) to give the title compound. (UPLC-MS) $t_R$ 1.15 min; ESI-MS 420.0 [M+H]$^+$.

Intermediate 25b: N-(3-chloro-4-(6-cyano-5-fluoropyridin-2-yl)phenyl)-4-methylbenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 4-methylbenzene-1-sulfonyl chloride and 6-(4-amino-2-chlorophenyl)-3-fluoropicolinonitrile (Intermediate 3a) at 0° C. for 2 h to afford the title compound as a white solid. (UPLC-MS) $t_R$ 1.15 min; ESI-MS 402.2 [M+H]$^+$; ESI-MS 400.1 [M–H]$^-$.

Intermediate 26a: 4-bromo-N-(1-(hydroxymethyl)cyclopentyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1-aminocyclopentyl)methanol to give the title compound as a colorless solid. (UPLC-MS) $t_R$ 1.02 min; ESI-MS 346.0/348.0 [M–H]$^-$.

Intermediate 26b: 4-(6-cyano-5-fluoropyridin-2-yl)-N-(1-(hydroxymethyl)cyclopentyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using 4-bromo-N-(1-(hydroxymethyl)cyclopentyl)-3-methyl benzenesulfonamide (Intermediate 26a) to give the title compound. (UPLC-MS) $t_R$ 0.98 min; ESI-MS 388.2 [M–H]$^-$.

Intermediate 27b: 3-chloro-N-(3-chloro-4-(6-cyano-5-fluoropyridin-2-yl)phenyl)-4-fluorobenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-chloro-4-fluorobenzene-1-sulfonyl chloride and 6-(4-amino-2-chlorophenyl)-3-fluoropicolinonitrile (Intermediate 3a) at 0° C. for 2 h without extracting workup to afford the title compound as an off-white solid. (UPLC-MS) $t_R$ 1.22 min; ESI-MS 440.0/442.0 [M+H]$^+$; ESI-MS 438.0/440.1 [M–H]$^-$.

Intermediate 28b: 3-chloro-N-(3-chloro-4-(6-cyano-5-fluoropyridin-2-yl)phenyl)benzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-chlorobenzene-1-sulfonyl chloride and 6-(4-amino-2-chlorophenyl)-3-fluoropicolinonitrile (Intermediate 3a) at 0° C. for 1 h then, RT for 30 min to afford the title compound as an off-white solid. (UPLC-MS) $t_R$ 1.20 min; ESI-MS 421.9/424.1 [M+H]$^+$; ESI-MS 420.1/422.0 [M–H]$^-$.

Intermediate 29a: 4-bromo-3-chloro-N-((1R,2R)-2-hydroxycyclopentyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1R,2R)-2-aminocyclopentanol to give the title compound as a colorless solid. (UPLC-MS) $t_R$ 0.94 min; ESI-MS 354.0 [M–H]$^-$.

Intermediate 29b: 3-chloro-4-(6-cyano-5-fluoropyridin-2-yl)-N-((1R,2R)-2-hydroxycyclopentyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1R,2R)-2-hydroxycyclopentyl)benzenesulfonamide (Intermediate 29a) to give the title compound as an off-white solid. (UPLC-MS) $t_R$ 0.94 min; ESI-MS 394.0 [M–H]$^-$.

Intermediate 30a: 4-bromo-3-chloro-N-(1-(hydroxymethyl)cyclopentyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1-aminocyclopentyl)methanol to give the title compound as a colorless solid. (UPLC-MS) $t_R$ 1.04 min; ESI-MS 366.1/368.1/370.1 [M–H]$^-$.

Intermediate 30b: 3-chloro-4-(6-cyano-5-fluoropyridin-2-yl)-N-(1-(hydroxymethyl)cyclopentyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(1-(hydroxymethyl)cyclopentyl)benzenesulfonamide (Intermediate 30a) to give the title compound. (UPLC-MS) $t_R$ 1.02 min; ESI-MS 408.2 [M–H]$^-$.

Intermediate 31a: 4-bromo-3-chloro-N-(1,1-dioxidotetrahydrothiophen-3-yl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 3-aminotetrahydrothiophene 1,1-dioxide to give the title compound as a colorless solid. (UPLC-MS) $t_R$ 0.91 min; ESI-MS 388.0 [M–H]$^-$.

Intermediate 31 b: 3-chloro-4-(6-cyano-5-fluoropyridin-2-yl)-N-(1,1-dioxidotetrahydrothiophen-3-yl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(1,1-dioxido-tetrahydrothiophen-3-yl)benzenesulfonamide (Intermediate 31a) to give the title compound as an off-white solid. (UPLC-MS) $t_R$ 0.90 min; ESI-MS 428.1 [M–H]⁻.

Intermediate 32b: N-(3-chloro-4-(6-cyano-5-fluoro-pyridin-2-yl)phenyl)-2-hydroxy-5-methylbenzene-sulfonamide The title compound was prepared in an analogous manner to 4-chloro-N-(3-chloro-4-(6-cyano-5-fluoropyridin-2-yl)phenyl)benzenesulfonamide (Intermediate 3b) using an excess of 2-hydroxy-5-methylbenzene-1-sulfonyl chloride (1.7 eq) and 6-(4-amino-2-chlorophenyl)-3-fluoropicolinonitrile (Intermediate 3a) at RT for 4 days to afford the title compound as a white foam. (UPLC-MS) $t_R$ 1.09 min; ESI-MS 418.0 [M+H]⁺.

Intermediate 33a: N-(4-bromo-3-methylphenyl)-3-fluorobenzenesulfonamide

The title compound was prepared in an analogous manner to 4-chloro-N-(3-chloro-4-(6-cyano-5-fluoropyridin-2-yl)phenyl)benzenesulfonamide (Intermediate 3b) using 3-fluorobenzene-1-sulfonyl chloride and 4-bromo-3-methylaniline at 0° C. for 2.5 hr. No workup done, the reaction was concentrated under reduced pressure and the crude material was purified using silica gel column chromatography (0 to 10% EtOAc in Cyclohexane) to afford the title compound as a white solid. (UPLC-MS) $t_R$ 1.15 min; ESI-MS 342.0/344.0 [M–H]⁻.

Intermediate 33b: N-(4-(6-cyano-5-fluoropyridin-2-yl)-3-methylphenyl)-3-fluorobenzenesulfonamide Step 1: A vial was charged with 6-bromo-3-fluoropicolinonitrile (50 mg, 0.249 mmol), bis(pinacolato)diboron (76 mg, 0.299 mmol), KOAc (48.8 mg, 0.498 mmol) and PdCl₂(dppf) (9.10 mg, 0.012 mmol). The vial was sealed, Dioxane (1 mL) was added, and the reaction mixture was stirred at 80° C. for 3 h, cooled down to RT, diluted with EtOAc and passed through a pad of Celite. The pad was washed several times with EtOAc. The combined filtrates were concentrated under reduced pressure to give crude 3-fluoro-6-(4,4,5,5-tetramethyl-1,3,2-dioxaborolan-2-yl)picolinonitrile.
Step 2: The crude material was diluted with ACN (2 mL) and treated with N-(4-bromo-3-methylphenyl)-3-fluorobenzenesulfonamide (Intermediate 33a, 94 mg, 0.274 mmol), K₂CO₃ aq. 2M (0.249 mL, 0.498 mmol), and PdCl₂(dppf) (9.10 mg, 0.012 mmol). The vial was sealed and irradiated in a microwave reactor at 120° C. for 30 min. The reaction was diluted with EtOAc and passed through a pad of Celite. The filtrate was washed with a sat. aq. NaHCO₃ solution, and the aqueous layer was extracted twice with EtOAc. The combined organic layers were washed with brine, dried over anhydrous MgSO₄, filtered and concentrated under reduced pressure. The residue was purified by normal phase chromatography (0 to 20% EtOAc in Cyclohexane) to afford the title compound as a pale yellow solid. (UPLC-MS) $t_R$ 1.09 min; ESI-MS 386.1 [M+H]⁺; ESI-MS 384.1 [M–H]⁻.

Intermediate 34a: 1-((4-bromo-3-methylphenyl)sulfonyl)-4,4-difluoropyrrolidine-2-carboxamide The title compound was prepared in an analogous manner to 4-bromo-N-(3-hydroxy-3-(trifluoromethyl)cyclobutyl)-3-methylbenzenesulfonamide (Intermediate 2a) using 4,4-difluoropyrrolidine-2-carboxamide to give the title compound. (UPLC-MS) $t_R$ 1.66 min; API-MS m/z: 384.0/386.0 [M+H]⁺.

Intermediate 34b: 1-((4-(6-cyano-5-fluoropyridin-2-yl)-3-methylphenyl)sulfonyl)-4,4-difluoropyrrolidine-2-carboxamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 1-((4-bromo-3-methylphenyl)sulfonyl)-4,4-difluoropyrrolidine-2-carboxamide (Intermediate 34a) to give the title compound. (UPLC-MS) $t_R$ 0.91 min; ESI-MS 425.2 [M+H]⁺.

Intermediate 35a: 4-bromo-3-chloro-N-((1S,2R)-2-hydroxycyclopentyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1R,2S)-2-aminocyclopentanol to give the title compound as a colorless solid. (UPLC-MS) $t_R$ 1.00 min; ESI-MS 354.0 [M–H]⁻.

Intermediate 35b: 3-chloro-4-(6-cyano-5-fluoropyridin-2-yl)-N-((1S,2R)-2-hydroxycyclopentyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1S,2R)-2-hydroxycyclopentyl)benzenesulfonamide (Intermediate 29a) to give the title compound as an off-white solid. (UPLC-MS) $t_R$ 0.98 min; ESI-MS 394.0 [M–H]⁻.

Intermediate 36a: 4-bromo-3-chloro-N-(4-methylcyclohexyl)benzenesulfonamide

The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-methylcyclohexanamine to give the title compound as a colorless solid. (UPLC-MS) $t_R$ 1.33 min and 1.45 min (mixture of diastereomers); ESI-MS 368.0 [M+H]⁺.

Intermediate 36b: 3-chloro-4-(6-cyano-5-fluoropyridin-2-yl)-N-(4-methylcyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(4-methylcyclohexyl)benzenesulfonamide (Intermediate 36a) to give the title compound. (UPLC-MS) $t_R$ 1.28 min; ESI-MS 408.1 [M+H]⁺.

Intermediate 37a: (S)-(1-((4-bromo-3-methylphenyl)sulfonyl)-4,4-difluoropyrrolidin-2-yl)methanol The title compound was prepared in an analogous manner to (S)-(1-((4-bromo-3-chlorophenyl)sulfonyl)-4,4-difluoropyrrolidin-2-yl)methanol (Intermediate 18a) using 4-bromo- 3-methylbenzene-1-sulfonyl chloride to give the title compound. (UPLC-MS) $t_R$ 1.52 min; API-MS m/z: 370.1 [M+H]$^+$.

Intermediate 37b: (S)-6-(4-((4,4-difluoro-2-(hydroxymethyl)pyrrolidin-1-yl)sulfonyl)-2-methylphenyl)-3-fluoropicolinonitrile The title compound was prepared in an analogous manner to (S)-6-(2-chloro-4-((4,4-difluoro-2-(hydroxymethyl)pyrrolidin-1-yl)sulfonyl)phenyl)-3-fluoropicolinonitrile (Intermediate 18b) using (S)-(1-((4-bromo-3-methylphenyl)sulfonyl)-4,4-difluoropyrrolidin-2-yl)methanol (Intermediate 37a) to give the title compound. (UPLC-MS) $t_R$ 1.51 min; API-MS 412.2 [M+H]$^+$.

Intermediate 38a: 5-chloro-3-nitro-1H-pyrazolo[4,3-b]pyridine

A solution of HNO$_3$ (4.18 mL, 61 mmol) and H$_2$SO$_4$ (4.13 mL, 75 mmol) was added dropwise to solution of 5-chloro-1H-pyrazolo[4,3-b]pyridine (1.05 g, 6.84 mmol) in H$_2$SO$_4$ (6.84 mL) at 0° C. The mixture was stirred at 115° C. for 30 min and then poured onto ice water and adjusted to pH 8 with aq. NH$_4$OH (33%). The light-yellow suspension was filtered, and the filter cake was washed several times with ice water to afford the title compound that was dried under high vacuum. (UPLC-MS) $t_R$ 0.60 min; ESI-MS 199.1 [M+H]$^+$.

Intermediate 38b: 5-chloro-1H-pyrazolo[4,3-b]pyridin-3-amine

To a suspension of 5-chloro-3-nitro-1H-pyrazolo[4,3-b]pyridine (Intermediate 38a) (1.48 g, 7.45 mmol) in MeOH (100 mL) was added Pd—C (0.16 g, 0.15 mmol). The reaction mixture was put under a hydrogen atmosphere, stirred at room temperature for 5 h and filtered over Celite. The filter cake was washed with MeOH, and the combined solutions were concentrated under reduced pressure to give the title compound which was used without further purification. (UPLC-MS) $t_R$ 0.48 min; ESI-MS 169.0 [M+H]$^+$.

Intermediate 38c: 4-Bromo-3-chloro-N-phenylbenzenesulfonamide

To a solution of 4-bromo-3-chlorobenzene-1-sulfonyl chloride (1.00 g, 3.45 mmol) in anhydrous pyridine (6.9 mL) was added dropwise aniline (0.32 mL, 3.52 mmol). The reaction was stirred at room temperature for 2.5 h and then concentrated under reduced pressure. The crude material was purified by silica gel column chromatography (0 to 100% EtOAc in Cyclohexane) to give the title compound. (UPLC-MS) $t_R$ 1.14 min; ESI-MS 346.6 [M+H]$^+$.

Intermediate 39a: 4-bromo-N-cyclohexyl-3-methylbenzenesulfonamide

The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and cyclohexanamine to give the title compound as a colorless solid. (UPLC-MS) $t_R$ 1.26 min; ESI-MS 332.1/334.1 [M+H]$^+$.

Intermediate 39b: 4-(6-cyano-5-fluoropyridin-2-yl)-N-cyclohexyl-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-cyclohexyl-3-methyl benzenesulfonamide (Intermediate 39a) to give the title compound. (UPLC-MS) $t_R$ 1.18 min; ESI-MS 374.2 [M+H]$^+$.

Intermediate 40a: 4-bromo-3-chloro-N-(3-fluorophenyl)benzenesulfonamide

The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and 3-fluoroaniline. The reaction mixture was stirred at RT for 17 h to afford the title compound as a colorless solid. (UPLC-MS) $t_R$ 1.17 min; ESI-MS 362.0/364.0/366.0 [M+H]$^+$.

Intermediate 40b: 3-chloro-4-(6-cyano-5-fluoropyridin-2-yl)-N-(3-fluorophenyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(3-fluorophenyl)benzenesulfonamide (Intermediate 40a) to give the title compound. (UPLC-MS) $t_R$ 1.16 min; ESI-MS 404.1/406.1 [M−H]$^−$.

Intermediate 41 b: N-(3-chloro-4-(6-cyano-5-fluoropyridin-2-yl)phenyl)-3-fluorobenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-fluorobenzene-1-sulfonyl chloride and 6-(4-amino-2-chlorophenyl)-3-fluoropicolinonitrile (Intermediate 3a) at 0° C. for 1 h then, RT, 30 min to afford the title compound as an off-white solid. (UPLC-MS) $t_R$ 1.15 min; ESI-MS 406.1 [M+H]$^+$; ESI-MS 404.1 [M−H]$^−$.

Intermediate 42a: N-(4-bromo-3-methylphenyl)-3-chlorobenzenesulfonamide

The title compound was prepared in an analogous manner to 4-chloro-N-(3-chloro-4-(6-cyano-5-fluoropyridin-2-yl)phenyl)benzenesulfonamide (Intermediate 3b) using 3-chlorobenzene-1-sulfonyl chloride and 4-bromo-3-methylaniline at 0° C. for 4 h. No extracting workup done, the reaction was concentrated under reduced pressure and the crude material was purified by silica gel column chromatography (0 to 15% EtOAc in Cyclohexane) to afford the title compound as a white solid. (UPLC-MS) $t_R$ 1.22 min; ESI-MS 358.0/360.0 [M−H]$^−$.

Intermediate 42b: 3-chloro-N-(4-(6-cyano-5-fluoropyridin-2-yl)-3-methylphenyl)benzenesulfonamide The title compound was prepared in an analogous manner to N-(4-(6-cyano-5-fluoropyridin-2-yl)-3-methylphenyl)-3-fluorobenzenesulfonamide (Intermediate 33b) using N-(4-bromo-3-methylphenyl)-3-chlorobenzenesulfonamide (Intermediate 42a) at the second step to afford the title compound as pale yellow solid. (UPLC-MS) $t_R$ 1.14 min; ESI-MS 402.1 [M+H]$^+$; ESI-MS 400.1 [M−H]$^−$.

Intermediate 43b: 3,4-dichloro-N-(3-chloro-4-(6-cyano-5-fluoropyridin-2-yl)phenyl)benzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3,4-dichlorobenzene-1-sulfonyl chloride and 6-(4-amino-2-chlorophenyl)-3-fluoropicolinonitrile (Intermediate 3a) at 0° C. for 1.5 h to afford the title compound as an off-white solid. (UPLC-MS) $t_R$ 1.25 min; ESI-MS 456.0/458.0/459.9 [M+H]$^+$; ESI-MS 454.0/456.0/458.0 [M−H]$^-$.

Intermediate 44a: 4-bromo-3-chloro-N-(3-hydroxycyclohexyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 3-aminocyclohexanol was to give the title compound as a colorless solid. (UPLC-MS) $t_R$ 0.94 min; ESI-MS 366.0/368.0/370.0 [M−H]$^-$.

Intermediate 44b: 3-chloro-4-(6-cyano-5-fluoropyridin-2-yl)-N-(3-hydroxycyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(3-hydroxycyclohexyl)benzenesulfonamide (Intermediate 44a) to give the title compound. (UPLC-MS) $t_R$ 0.94 min; ESI-MS 410.2 [M+H]$^+$.

Intermediate 45a: 4-bromo-3-chloro-N-((1r,4r)-4-hydroxycyclohexyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1r,4r)-4-aminocyclohexanol to give the title compound as a colorless solid. (UPLC-MS) $t_R$ 0.89 min; ESI-MS 366.0/368.0/370.0 [M−H]$^-$.

Intermediate 45b: 3-chloro-4-(6-cyano-5-fluoropyridin-2-yl)-N-((1r,4r)-4-hydroxycyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1r,4r)-4-hydroxycyclohexyl)benzenesulfonamide (Intermediate 45a) to give the title compound. (UPLC-MS) $t_R$ 0.90 min; ESI-MS 408.2 [M−H]$^-$.

Intermediate 46a: N-(4-bromo-3-chlorophenyl)benzenesulfonamide

The title compound was prepared in an analogous manner to 4-bromo-N-(3-hydroxy-3-(trifluoromethyl)cyclobutyl)-3-methylbenzenesulfonamide (Intermediate 2a) using 4-bromo-3,5-difluoroaniline and benzenesulfonyl chloride at RT for 2 hr. No extracting workup done, the reaction was concentrated under reduced pressure and the residue was purified by silica gel column chromatography (0 to 20% MeOH in DCM) to afford the title compound as a white solid. (UPLC-MS) $t_R$ 1.13 min; ESI-MS 343.9/345.9 [M−H]$^-$.

Intermediate 46b: N-(3-chloro-4-(4,4,5,5-tetramethyl-1,3,2-dioxaborolan-2-yl)phenyl)benzenesulfonamide To a solution of N-(4-bromo-3-chlorophenyl)benzenesulfonamide (Intermediate 46a, 219 mg, 0.632 mmol) in anhydrous dioxane (3 mL) was added bis(pinacolato)diboron (193 mg, 0.758 mmol), PCy$_3$ (12.40 mg, 0.044 mmol), KOAc (93 mg, 0.948 mmol) and Pd$_2$(dba)$_3$ (17.36 mg, 0.019 mmol). The reaction mixture was irradiated in a microwave reactor at 120° C. for 1 h. The reaction was quenched with water and extracted three times with EtOAc. The combined organic layers were dried over anhydrous MgSO$_4$, filtered and concentrated under reduced pressure. The crude material was purified by silica gel column chromatography (0 to 100% EtOAc in cyclohexane) to give the title compound. (UPLC-MS) $t_R$ 1.19 min; ESI-MS 392.2 [M−H]$^-$.

Intermediate 47a: 4-bromo-N-((1s,3s)-3-(hydroxymethyl)cyclobutyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and ((1s,3s)-3-aminocyclobutyl)methanol to give the title compound as a colorless solid. (UPLC-MS) $t_R$ 0.89 min; ESI-MS 334.1/336.0 [M+H]$^+$.

Intermediate 47b: 4-(6-cyano-5-fluoropyridin-2-yl)-N-((1s,3s)-3-(hydroxymethyl)cyclobutyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-((1s,3s)-3-(hydroxymethyl)cyclobutyl)-3-methylbenzenesulfonamide (Intermediate 47a) to give the title compound. (UPLC-MS) $t_R$ 0.91 min; ESI-MS 376.1 [M−H]$^-$.

Intermediate 48a: 4-bromo-3-chloro-N-((1s,4s)-4-hydroxycyclohexyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1s,4s)-4-aminocyclohexanol to give the title compound as a colorless solid. (UPLC-MS) $t_R$ 0.97 min; ESI-MS 366.0/368.0/370.0 [M−H]$^-$.

Intermediate 48b: 3-chloro-4-(6-cyano-5-fluoropyridin-2-yl)-N-((1s,4s)-4-hydroxycyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1s,4s)-4-hydroxycyclohexyl)benzenesulfonamide (Intermediate 48a) to give the title compound. (UPLC-MS) $t_R$ 0.96 min; ESI-MS 410.1 [M+H]$^+$.

Intermediate 49a: 4-bromo-3-fluoro-N-phenylbenzenesulfonamide

To a solution of aniline (0.033 mL, 0.366 mmol) in pyridine (2 mL) was added dropwise 4-bromo-3-fluorobenzene-1-sulfonyl chloride (0.054 mL, 0.366 mmol). The reaction mixture was stirred at RT for 35 min, then partitioned between water and EtOAc. The organic layer was separated and the aq. layer was extracted twice with EtOAc. The combined organic layers were dried over MgSO$_4$, filtered and concentrated under reduced pressure. The resulting product was purified by silica gel column chromatography (4 to 20% MeOH in DCM) to afford the title compound. (UPLC-MS) t$_R$ 1.09 min; ESI-MS 328.0 [M−H]$^−$.

Intermediate 49b: 3-fluoro-N-phenyl-4-(4,4,5,5-tetramethyl-1,3,2-dioxaborolan-2-yl)benzenesulfonamide The title compound was prepared in na analogous manner to N-(3-chloro-4-(4,4,5,5-tetramethyl-1,3,2-dioxaborolan-2-yl)phenyl)benzenesulfonamide (Intermediate 46b) using 4-bromo-3-fluoro-N-phenylbenzenesulfonamide (Intermediate 49a) in anhydrous dioxane. The reaction mixture was filtered through a pad of Celite which was washed with DCM. The combined solutions were concentrated under reduced pressure. The crude material was purified by silica gel column chromatography (0 to 100% EtOAc in cyclohexane) to give the title compound as a yellow solid. (UPLC-MS) t$_R$ 1.22 min; ESI-MS 376.0 [M−H]$^−$.

Intermediate 50a: 4-bromo-3-chloro-N-(1,1-dioxidotetrahydro-2H-thiopyran-4-yl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-aminotetrahydro-2H-thiopyran 1,1-dioxide to give the title compound as a colorless solid. (UPLC-MS) t$_R$ 0.88 min; ESI-MS 402.3 [M−H]$^−$.

Intermediate 50b: 3-chloro-4-(6-cyano-5-fluoropyridin-2-yl)-N-(1,1-dioxidotetrahydro-2H-thiopyran-4-yl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(1,1-dioxidotetrahydro-2H-thiopyran-4-yl)benzenesulfonamide (Intermediate 50a) to give the title compound. (UPLC-MS) t$_R$ 0.90 min; ESI-MS 442.2 [M−H]$^−$.

Intermediate 51a: 2-((4-bromo-3-chlorophenyl)sulfonyl)octahydrocyclopenta[c]pyrrole The title compound was prepared in an analogous manner to 4-bromo-3-chloro-N-((1s,3s)-3-hydroxy-3-(trifluoromethyl)cyclobutyl)benzenesulfonamide (Intermediate 1a) using octahydrocyclopenta[c]pyrrole to give the title compound as a colorless solid. (UPLC-MS) t$_R$ 1.33 min; ESI-MS 364.1/366.0/367.8 [M+H]$^+$.

Intermediate 51b: 6-(2-chloro-4-((hexahydrocyclopenta[c]pyrrol-2(1H)-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 2-((4-bromo-3-chlorophenyl)sulfonyl)octahydrocyclopenta[c]pyrrole (Intermediate 51a) to give the title compound. (UPLC-MS) t$_R$ 1.27 min; ESI-MS 406.2 [M+H]$^+$.

Intermediate 52a: 4-bromo-3-chloro-N-(3-chloro-2-fluorophenyl)benzenesulfonamide The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and 3-chloro-2-fluoroaniline. The reaction mixture was stirred at RT for 4.5 h. The title compound was obtained as a colorless solid. (UPLC-MS) t$_R$ 1.22 min; ESI-MS 395.9/397.9/399.9 [M−H]$^−$.

Intermediate 52b: 3-chloro-N-(3-chloro-2-fluorophenyl)-4-(6-cyano-5-fluoropyridin-2-yl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(3-chloro-2-fluorophenyl)benzenesulfonamide (Intermediate 52a) to give the title compound. (UPLC-MS) t$_R$ 1.20 min; ESI-MS 438.0/440.0 [M−H]$^−$.

Intermediate 53b: 4-acetyl-N-(3-chloro-4-(6-cyano-5-fluoropyridin-2-yl)phenyl)-3,4-dihydro-2H-benzo[b][1,4]oxazine-6-sulfonamide The title compound was prepared in an analogous manner to 4-chloro-N-(3-chloro-4-(6-cyano-5-fluoropyridin-2-yl)phenyl)benzenesulfonamide (Intermediate 3b) using an excess of 4-acetyl-3,4-dihydro-2H-benzo[b][1,4]oxazine-6-sulfonyl chloride (1.5 eq) and 6-(4-amino-2-chlorophenyl)-3-fluoropicolinonitrile (Intermediate 3a) at RT overnight to afford the title compound as an off-white solid. (UPLC-MS) t$_R$ 1.02 min; ESI-MS 487.2 [M+H]$^+$; ESI-MS 485.3 [M−H]$^−$.

Intermediate 54a: 4-bromo-N-((1R,4R)-4-hydroxycyclohexyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1r,4r)-4-aminocyclohexanol to give the title compound as a colorless solid. (UPLC-MS) t$_R$ 0.87 min; ESI-MS 348.0/350.0 [M+H]$^+$.

Intermediate 54b: 4-(6-cyano-5-fluoropyridin-2-yl)-N-((1R,4R)-4-hydroxycyclohexyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-((1R,4R)-4-hydroxycyclohexyl)-3-methylbenzenesulfonamide (Intermediate 54a) to give the title compound. (UPLC-MS) t$_R$ 0.88 min; ESI-MS 390.1 [M+H]$^+$.

Intermediate 55a: (2R,4R)-1-((4-bromo-3-chlorophenyl)sulfonyl)-4-fluoropyrrolidine-2-carboxamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (2R,4R)-4-fluoropyrrolidine-2-carboxamide to give the title compound as a colorless solid. (UPLC-MS) $t_R$ 0.85 min; ESI-MS 387.2 [M+H]$^+$.

Intermediate 55b: (2R,4R)-1-((3-chloro-4-(6-cyano-5-fluoropyridin-2-yl)phenyl)sulfonyl)-4-fluoropyrrolidine-2-carboxamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using (2R,4R)-1-((4-bromo-3-chlorophenyl)sulfonyl)-4-fluoropyrrolidine-2-carboxamide (Intermediate 55a) to give the title compound as an off-white solid. (UPLC-MS) $t_R$ 0.88 min; ESI-MS 427.1 [M−H]$^-$.

Intermediate 56a: 4-bromo-3-chloro-N-(2,3-dichlorophenyl)benzenesulfonamide

The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and 2,3-dichloroaniline. The reaction mixture was stirred at RT for 5.5 h. The title compound was obtained as a colorless solid. (UPLC-MS) $t_R$ 1.30 min; ESI-MS 411.9/413.9/415.9/417.9 [M−H]$^-$.

Intermediate 56b: 3-chloro-4-(6-cyano-5-fluoropyridin-2-yl)-N-(2,3-dichlorophenyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(2,3-dichlorophenyl)benzenesulfonamide (Intermediate 56a) to give the title compound. (UPLC-MS) $t_R$ 1.25 min; ESI-MS 454.0/456.0 [M−H]$^-$.

Intermediate 57a: (R)-1-((4-bromo-3-chlorophenyl)sulfonyl)pyrrolidin-3-ol

The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and (R)-pyrrolidin-3-ol. The reaction mixture was stirred at 0° C. for 60 min. The title compound was obtained as a yellow solid. (UPLC-MS) $t_R$ 0.91 min; ESI-MS 340.0/342.1 [M+H]$^+$.

Intermediate 57b: (R)-6-(2-chloro-4-((3-hydroxypyrrolidin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using (R)-1-((4-bromo-3-chlorophenyl)sulfonyl)pyrrolidin-3-ol (Intermediate 57a) to give the title compound. (UPLC-MS) $t_R$ 0.92 min; ESI-MS 382.1 [M+H]$^+$.

Intermediate 58a: 4-bromo-3-chloro-N-((1R,4R)-4-hydroxy-4-methylcyclohexyl)benzenesulfonamide The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and (1R,4R)-4-amino-1-methylcyclohexanol. The reaction mixture was stirred at 0° C. for 30 min and at RT for 6.5 h, then diluted with EtOAc. The organic layer was washed twice with a 1N aq. NH$_4$Cl. The aq. layer was extracted twice with EtOAc. The combined organic layers were washed with brine, dried over anhydrous MgSO$_4$, filtered and concentrated under reduced pressure. The crude material was purified by silica gel column chromatography (0 to 40% EtOAc in Cyclohexane) to give the title compound as a white solid. (UPLC-MS) $t_R$ 0.94 min; 380.0/382.1/384.0 [M−H]$^-$.

Intermediate 58b: 3-chloro-4-(6-cyano-5-fluoropyridin-2-yl)-N-((1R,4R)-4-hydroxy-4-methylcyclohexyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) 4-bromo-3-chloro-N-((1R,4R)-4-hydroxy-4-methylcyclohexyl)benzenesulfonamide (Intermediate 58a) to give the title compound. (UPLC-MS) $t_R$ 0.95 min; ESI-MS 422.1 [M−H]$^-$.

Intermediate 59b: N-(3-chloro-4-(6-cyano-5-fluoropyridin-2-yl)phenyl)-1-phenylmethanesulfonamide The title compound was prepared in an analogous manner to 4-chloro-N-(3-chloro-4-(6-cyano-5-fluoropyridin-2-yl)phenyl)benzenesulfonamide (Intermediate 3b) using phenylmethanesulfonyl chloride and 6-(4-amino-2-chlorophenyl)-3-fluoropicolinonitrile (Intermediate 3a) at 0° C. for 2 h without extracting workup to afford the title compound as a pale yellow solid. (UPLC-MS) $t_R$ 1.12 min; ESI-MS 402.1 [M+H]$^+$; ESI-MS 400.1 [M−H]$^-$.

Intermediate 61b: N-(5-(N-(3-chloro-4-(6-cyano-5-fluoropyridin-2-yl)phenyl)sulfamoyl)-2-methoxyphenyl)acetamide To a solution of 6-(4-amino-2-chlorophenyl)-3-fluoropicolinonitrile (56 mg, 0.226 mmol) in Pyridine (3 mL) cooled down to 0° C. was added 3-acetamido-4-methoxybenzene-1-sulfonyl chloride (59.6 mg, 0.226 mmol). The reaction was stirred at this temperature for 5 h. 0.6 eq of 3-acetamido-4-methoxybenzene-1-sulfonyl chloride was added and the reaction was stirred overnight at RT. The mixture was quenched with a sat. aq. NH$_4$Cl solution and EtOAc was added. Both phases were separated and the aq. layer was extracted twice with EtOAc. The combined organic layers were dried over anhydrous MgSO$_4$, filtered and evaporated to under reduced pressure. The residue was purified by silica gel column chromatography (0 to 100% EtOAc in Cyclohexane) to afford the title compound as a light yellow foam. (UPLC-MS) $t_R$ 1.01 min; ESI-MS 475.1 [M+H]$^+$; ESI-MS 473.1 [M−H]$^-$.

Intermediate 62b: N-(3-chloro-4-(6-cyano-5-fluoropyridin-2-yl)phenyl)-3-(trifluoromethyl)benzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-(trifluoromethyl)benzene-1-sulfonyl chloride and 6-(4-amino-2-chlorophenyl)-3-fluoropicolinonitrile (Intermediate 3a) at 0° C. for 2 h to afford the title compound as a white solid. (UPLC-MS) $t_R$ 1.20 min; ESI-MS 456.1 [M+H]$^+$; ESI-MS 454.1 [M–H]$^-$.

Intermediate 63a: 3-((4-bromo-3-chlorophenyl)sulfonyl)-3-azabicyclo[3.1.0]hexane The title compound was prepared in an analogous manner to 4-bromo-3-chloro-N-((1s,3s)-3-hydroxy-3-(trifluoromethyl)cyclobutyl)benzenesulfonamide (Intermediate 1a) using 3-azabicyclo[3.1.0]hexane to give the title compound as a colorless solid. (UPLC-MS) $t_R$ 1.17 min; ESI-MS 338.0 [M+H]$^+$.

Intermediate 63b: 6-(4-(3-azabicyclo[3.1.0]hexan-3-ylsulfonyl)-2-chlorophenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 3-((4-bromo-3-chlorophenyl)sulfonyl)-3-azabicyclo[3.1.0]hexane (Intermediate 63a) to give the title compound. (UPLC-MS) $t_R$ 1.19 min; ESI-MS 378.2 [M+H]$^+$.

Intermediate 64a: 4-bromo-N-((1S,3S)-3-hydroxycyclobutyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1S,3S)-3-aminocyclobutanol to give the title compound as a colorless solid. (UPLC-MS) $t_R$ 0.82 min; ESI-MS 320.0 [M+H]$^+$.

Intermediate 64b: 4-(6-cyano-5-fluoropyridin-2-yl)-N-((1S,3S)-3-hydroxycyclobutyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-((1S,3S)-3-hydroxycyclobutyl)-3-methylbenzenesulfonamide (Intermediate 64a) to give the title compound. (UPLC-MS) $t_R$ 0.83 min; ESI-MS 362.0 [M+H]$^+$.

Intermediate 65a: 4-bromo-N-(3-hydroxycyclohexyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and 3-aminocyclohexanol to give the title compound as a colorless solid. (UPLC-MS) $t_R$ 0.91 min; ESI-MS 348.1/350.0 [M+H]$^+$.

Intermediate 65b: 4-(6-cyano-5-fluoropyridin-2-yl)-N-(3-hydroxycyclohexyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-(3-hydroxycyclohexyl)-3-methylbenzenesulfonamide (Intermediate 65a) to give the title compound. (UPLC-MS) $t_R$ 0.90 min; ESI-MS 390.2 [M+H]$^+$.

Intermediate 66a: 1-((4-bromo-3-methylphenyl)sulfonyl)-3-(trifluoromethyl)azetidin-3-ol The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and 3-(trifluoromethyl)azetidin-3-ol to give the title compound as a colorless solid. (UPLC-MS) $t_R$ 1.07 min; ESI-MS 372.2 [M–H]$^-$.

Intermediate 66b: 3-fluoro-6-(4-((3-hydroxy-3-(trifluoromethyl)azetidin-1-yl)sulfonyl)-2-methylphenyl)picolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 1-((4-bromo-3-methylphenyl)sulfonyl)-3-(trifluoromethyl)azetidin-3-ol (Intermediate 66a) to give the title compound. (UPLC-MS) $t_R$ 0.78 min; ESI-MS 428.1 [M+H]$^+$.

Intermediate 67b: N-(3-chloro-4-(6-cyano-5-fluoropyridin-2-yl)phenyl)-3-methoxybenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-methoxybenzene-1-sulfonyl chloride and 6-(4-amino-2-chlorophenyl)-3-fluoropicolinonitrile (Intermediate 3a) at 0° C. for 2 h to afford the title compound as white solid. (UPLC-MS) $t_R$ 1.12 min; ESI-MS 418.1 [M+H]$^+$; ESI-MS 416.1 [M–H]$^-$.

Intermediate 68a: 4-bromo-N-((1R,4R)-4-hydroxy-4-(trifluoromethyl)cyclohexyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1R,4R)-4-amino-1-(trifluoromethyl)cyclohexanol to give the title compound as a colorless solid. (UPLC-MS) $t_R$ 1.06 min; ESI-MS 414.1/416.1 [M–H]$^-$.

Intermediate 68b: 4-(6-cyano-5-fluoropyridin-2-yl)-N-((1r,4r)-4-hydroxy-4-(trifluoromethyl)cyclohexyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-((1r,4r)-4-hydroxy-4-

(trifluoromethyl)cyclohexyl)-3-methylbenzenesulfonamide (Intermediate 68a) to give the title compound. (UPLC-MS) $t_R$ 1.03 min; ESI-MS 458.2 [M+H]$^+$. Intermediate 69a: 4-bromo-N-((1S,4S)-4-hydroxycyclohexyl)-3-methylbenzenesulfonamide. The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1S,4S)-4-aminocyclohexanol to give the title compound as a colorless solid. (UPLC-MS) $t_R$ 0.96 min; ESI-MS 348.0/350.0 [M+H]$^+$.

Intermediate 69b: 4-(6-cyano-5-fluoropyridin-2-yl)-N-((1S,4S)-4-hydroxycyclohexyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using 4-bromo-N-((1S,4S)-4-hydroxycyclohexyl)-3-methylbenzenesulfonamide (Intermediate 69a) to give the title compound. (UPLC-MS) $t_R$ 0.92 min; ESI-MS 390.2 [M+H]$^+$.

Intermediate 70a: (S)-(1-((4-bromo-3-methylphenyl)sulfonyl)pyrrolidin-2-yl)methanol The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (S)-pyrrolidin-2-ylmethanol to give the title compound as a colorless solid. (UPLC-MS) $t_R$ 0.98 min; ESI-MS 336.0 [M+H]$^+$.

Intermediate 70b: (S)-3-fluoro-6-(4-((2-(hydroxymethyl)pyrrolidin-1-yl)sulfonyl)-2-methylphenyl)picolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using (S)-(1-((4-bromo-3-methylphenyl)sulfonyl)pyrrolidin-2-yl)methanol (Intermediate 70a) to give the title compound. (UPLC-MS) $t_R$ 0.98 min; ESI-MS 376.1 [M+H]$^+$.

Intermediate 71a: (S)-1-((4-bromo-3-chlorophenyl)sulfonyl)pyrrolidin-3-ol

The title compound was prepared in an analogous manner to (S)-1-((4-bromo-3-chlorophenyl)sulfonyl)pyrrolidin-3-ol (Intermediate 57a) using (S)-pyrrolidin-3-ol and purification was preceded by an aqueous workup whereby the reaction mixture was diluted with EtOAc and washed subsequently with 1N aq. NH$_4$Cl solution, 0.1M aq. LiBr solution, and brine. The organic layer was dried over anhydrous MgSO$_4$, filtered, and concentrated under reduced pressure to afford the title compound. (UPLC-MS) $t_R$ 0.91 min; ESI-MS 340.0/342.0 [M+H]$^+$.

Intermediate 71b: (S)-6-(2-chloro-4-((3-hydroxypyrrolidin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using (S)-1-((4-bromo-3-chlorophenyl)sulfonyl)pyrrolidin-3-ol (Intermediate 71a) to give the title compound. (UPLC-MS) $t_R$ 0.95 min; ESI-MS 382.1 [M+H]$^+$.

Intermediate 72a: 4-bromo-3-chloro-N-(2-hydroxyethyl)benzenesulfonamide

The title compound was prepared in an analogous manner to 4-bromo-3-chloro-N-((1s,3s)-3-hydroxy-3-(trifluoromethyl)cyclobutyl)benzenesulfonamide (Intermediate 1a) using 2-aminoethanol to give the title compound as a colorless solid. (UPLC-MS) $t_R$ 0.84 min; ESI-MS 311.9/313.9/315.9 [M–H]$^-$.

Intermediate 72b: 3-chloro-4-(6-cyano-5-fluoropyridin-2-yl)-N-(2-hydroxyethyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using 4-bromo-3-chloro-N-(2-hydroxyethyl)benzenesulfonamide (Intermediate 72a) to give the title compound. (UPLC-MS) $t_R$ 0.89 min; ESI-MS 356.1 [M+H]$^+$.

Intermediate 73a: N-benzyl-4-bromo-3-chlorobenzenesulfonamide

The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and benzylamine. The reaction mixture was stirred at 0° C. for 3.5 h. The title compound was obtained as a yellow solid. (UPLC-MS) $t_R$ 1.16 min; ESI-MS 357.9/359.9 [M+H]$^+$.

Intermediate 73b: N-benzyl-3-chloro-4-(6-cyano-5-fluoropyridin-2-yl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using N-benzyl-4-bromo-3-chlorobenzenesulfonamide (Intermediate 73a) to give the title compound. (UPLC-MS) $t_R$ 1.15 min; ESI-MS 402.1 [M+H]$^+$.

Intermediate 74a: 1-((4-bromo-3-chlorophenyl)sulfonyl)-3,3-difluoroazetidine

The title compound was prepared in an analogous manner to 4-bromo-3-chloro-N-((1s,3s)-3-hydroxy-3-(trifluoromethyl)cyclobutyl)benzenesulfonamide (Intermediate 1a) using 3,3-difluoroazetidine to give the title compound as a colorless solid. (UPLC-MS) $t_R$ 1.12 min; no ESI-MS ionization of parent observed.

Intermediate 74b: 6-(2-chloro-4-((3,3-difluoroazetidin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using 1-((4-bromo-3-chlorophenyl)sulfonyl)-3,3-difluoroazetidine (Intermediate 74a) to give the title compound. (UPLC-MS) $t_R$ 1.10 min; ESI-MS 384.3 [M+H]$^+$.

Intermediate 75a: 4-bromo-N-(tert-butyl)-3-fluorobenzenesulfonamide

The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-fluorobenzene-1-sulfonyl chloride and tert-butylamine to give the title compound as a colorless solid. (UPLC-MS) $t_R$ 1.12 min; ESI-MS 308.0/309.9 [M−H]⁻.

Intermediate 75b: 6-(2-chloro-4-((3,3-difluoroazetidin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-(tert-butyl)-3-fluorobenzenesulfonamide (Intermediate 75a) to give the title compound. (UPLC-MS) $t_R$ 1.11 min; ESI-MS 350.1 [M−H]⁻.

Intermediate 76b: N1-(3-chloro-4-(6-cyano-5-fluoropyridin-2-yl)phenyl)-N4-methyl benzene-1,4-disulfonamide The title compound was prepared in an analogous manner to 4-chloro-N-(3-chloro-4-(6-cyano-5-fluoropyridin-2-yl)phenyl)benzenesulfonamide (Intermediate 3b) using 4-(N-methylsulfamoyl)benzene-1-sulfonyl chloride and 6-(4-amino-2-chlorophenyl)-3-fluoropicolinonitrile (Intermediate 3a) at 0° C. for 2 h to afford the title compound as a pale yellow solid. (UPLC-MS) $t_R$ 1.03 min; ESI-MS 481.1 [M+H]⁺; ESI-MS 479.0 [M−H]⁻.

Intermediate 77a: 4-bromo-N-((1R,3R)-3-hydroxycyclobutyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride was used in place of 4-bromo-3-chlorobenzene-1-sulfonyl chloride and (1R,3R)-3-aminocyclobutanol to give the title compound as a colorless solid. (UPLC-MS) $t_R$ 0.84 min; ESI-MS 320.0 [M+H]⁺.

Intermediate 77b: 4-(6-cyano-5-fluoropyridin-2-yl)-N-((1R,3R)-3-hydroxycyclobutyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-N-((1R,3R)-3-hydroxycyclobutyl)-3-methylbenzenesulfonamide (Intermediate 77a) to give the title compound. (UPLC-MS) $t_R$ 0.79 min; ESI-MS 362.2 [M+H]⁺.

Intermediate 78b: N-(3-chloro-4-(6-cyano-5-fluoropyridin-2-yl)phenyl)-4-(trifluoromethyl)benzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 4-(trifluoromethyl)benzene-1-sulfonyl chloride and 6-(4-amino-2-chlorophenyl)-3-fluoropicolinonitrile (Intermediate 3a) at 0° C. for 1.5 h to afford the title compound as a yellow solid. (UPLC-MS) $t_R$ 1.23 min; ESI-MS 456.1 [M+H]⁺; ESI-MS 454.1 [M−H]⁻.

Intermediate 79b: N-(3-chloro-4-(6-cyano-5-fluoropyridin-2-yl)phenyl)-3,4-dimethoxybenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using a large excess of 3,4-dimethoxybenzene-1-sulfonyl chloride and 6-(4-amino-2-chlorophenyl)-3-fluoropicolinonitrile (Intermediate 3a) at RT for 2 days to afford the title compound as an off-white solid. (UPLC-MS) $t_R$ 1.08 min; ESI-MS 448.1 [M+H]⁺; ESI-MS 446.1 [M−H]⁻.

Intermediate 80a: 4-bromo-N-((1R,4R)-4-hydroxy-4-methylcyclohexyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and (1R,4R)-4-amino-1-methylcyclohexanol to give the title compound as a colorless solid. (UPLC-MS) $t_R$ 0.92 min; 362.1/364.0 [M+H]⁺.

Intermediate 80b: 4-(6-cyano-5-fluoropyridin-2-yl)-N-((1R,4R)-4-hydroxy-4-methylcyclohexyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4 bromo-N-((1R,4R)-4-hydroxy-4-methylcyclohexyl)-3-methylbenzenesulfonamide (Intermediate 80a) to give the title compound. (UPLC-MS) $t_R$ 0.91 min; ESI-MS 404.2 [M−H]⁻.

Intermediate 81a: 4-bromo-3-chloro-N-(2,3-difluorophenyl)benzenesulfonamide

The title compound was prepared in an analogous manner to 4-bromo-N-(3-hydroxy-3-(trifluoromethyl)cyclobutyl)-3-methylbenzenesulfonamide (Intermediate 2a) using 2,3-difluoroaniline. The reaction mixture was stirred at RT for 5.5 h. The title compound was obtained as an off-white solid. (UPLC-MS) $t_R$ 1.19 min; ESI-MS 380.0/382.0/383.5/384.8 [M−H]⁻.

Intermediate 81b: 3-chloro-4-(6-cyano-5-fluoropyridin-2-yl)-N-(2,3-difluorophenyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(2,3-difluorophenyl)benzenesulfonamide (Intermediate 82a) to give the title compound. (UPLC-MS) $t_R$ 1.16 min; ESI-MS 424.0 [M+H]⁺.

Intermediate 82b: N-(3-chloro-4-(6-cyano-5-fluoropyridin-2-yl)phenyl)naphthalene-2-sulfonamide The title compound was prepared in an analogous manner to 4-chloro-N-(3-chloro-4-(6-cyano-5-fluoropyridin-2-yl)

phenyl)benzenesulfonamide (Intermediate 3b) using naphthalene-2-sulfonyl chloride and 6-(4-amino-2-chlorophenyl)-3-fluoropicolinonitrile (Intermediate 3a) at 0° C. for 2 h to afford the title compound as an off-white solid. (UPLC-MS) $t_R$ 1.21 min; ESI-MS 438.1 [M+H]$^+$; ESI-MS 436.1 [M−H]$^−$.

Intermediate 83a: 2-(1-((4-bromo-3-methylphenyl)sulfonyl)pyrrolidin-3-yl)ethanol The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and 2-(pyrrolidin-3-yl)ethanol to give the title compound as a colorless solid. (UPLC-MS) $t_R$ 0.96 min; 348.2/350.0 [M+H]$^+$.

Intermediate 83b: 3-fluoro-6-(4-((3-(2-hydroxyethyl)pyrrolidin-1-yl)sulfonyl)-2-methylphenyl)picolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 2-(1-((4-bromo-3-methylphenyl)sulfonyl)pyrrolidin-3-yl)ethanol (Intermediate 83a) to give the title compound. (UPLC-MS) $t_R$ 0.94 min; ESI-MS 390.2 [M+H]$^+$.

Intermediate 84b: N-(3-chloro-4-(6-cyano-5-fluoropyridin-2-yl)phenyl)-3-methylbenzenesulfonamide The title compound was prepared in an analogous manner to 4-chloro-N-(3-chloro-4-(6-cyano-5-fluoropyridin-2-yl)phenyl)benzenesulfonamide (Intermediate 3b) using 3-methylbenzene-1-sulfonyl chloride and 6-(4-amino-2-chlorophenyl)-3-fluoropicolinonitrile (Intermediate 3a) at 0° C. for 2 h to afford the title compound as a white solid. (UPLC-MS) $t_R$ 1.15 min; ESI-MS 402.1 [M+H]$^+$; ESI-MS 400.1 [M−H]$^−$.

Intermediate 85a: 4-bromo-3-chloro-N-((1S,3S)-3-(hydroxymethyl)cyclobutyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using ((1S,3S)-3-aminocyclobutyl)methanol to give the title compound as a colorless solid. (UPLC-MS) $t_R$ 0.88 min; ESI-MS 356.1 [M+H]$^+$.

Intermediate 85b: 3-chloro-4-(6-cyano-5-fluoropyridin-2-yl)-N-((1S,3S)-3-(hydroxymethyl)cyclobutyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1S,3S)-3-(hydroxymethyl)cyclobutyl)benzenesulfonamide (Intermediate 85a) to give the title compound. (UPLC-MS) $t_R$ 0.92 min; ESI-MS 396.1 [M−H]$^−$.

Intermediate 86b: 4-acetyl-N-(3-chloro-4-(6-cyano-5-fluoropyridin-2-yl)phenyl)-3,4-dihydro-2H-benzo[b][1,4]oxazine-6-sulfonamide The title compound was prepared in an analogous manner to 4-chloro-N-(3-chloro-4-(6-cyano-5-fluoropyridin-2-yl)phenyl)benzenesulfonamide (Intermediate 3b) using an excess of 4-acetyl-3,4-dihydro-2H-benzo[b][1,4]oxazine-6-sulfonyl chloride and 6-(4-amino-2-chlorophenyl)-3-fluoropicolinonitrile (Intermediate 3a) at 0° C. to RT for 8 h to afford the title compound. (UPLC-MS) $t_R$ 1.04 min; ESI-MS 487.1 [M+H]$^+$; ESI-MS 485.1 [M−H]$^−$.

Intermediate 87a: 1-((4-bromo-3-chlorophenyl)sulfonyl)-3-phenoxyazetidine

The title compound was prepared in an analogous manner to 4-bromo-3-chloro-N-((1s,3s)-3-hydroxy-3-(trifluoromethyl)cyclobutyl)benzenesulfonamide (Intermediate 1a) using 3-phenoxyazetidine to give the title compound as a colorless solid. (UPLC-MS) $t_R$ 1.27 min; no ESI-MS ionization of parent observed.

Intermediate 87b: 6-(2-chloro-4-((3-phenoxyazetidin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 1-((4-bromo-3-chlorophenyl)sulfonyl)-3-phenoxyazetidine (Intermediate 87a) to give the title compound. (UPLC-MS) $t_R$ 1.23 min; ESI-MS 444.2 [M+H]$^+$.

Intermediate 88b: N-(3-chloro-4-(6-cyano-5-fluoropyridin-2-yl)phenyl)-4-(trifluoromethoxy)benzenesulfonamide To a solution of 6-(4-amino-2-chlorophenyl)-3-fluoropicolinonitrile (60 mg, 0.242 mmol) in DCM (4 mL) cooled down to 0° C. were added 4-(trifluoromethoxy)benzene-1-sulfonyl chloride (0.042 mL, 0.254 mmol) and DIPEA (0.085 mL, 0.485 mmol). The reaction was warmed up to RT and stirred at this temperature for 24 h. The mixture was quenched with a sat. aq. NaHCO$_3$ solution and EtOAc was added. Both phases were separated and the aq. layer was extracted twice with EtOAc. The combined organic layers were dried over anhydrous MgSO$_4$, filtered and evaporated under reduced pressure. The residue was purified by silica gel column chromatography (0 to 20% EtOAc in Cyclohexane) to afford the title compound. (UPLC-MS) $t_R$ 1.22 min; ESI-MS 472.0 [M+H]$^+$; ESI-MS 470.0 [M−H]$^−$.

Intermediate 89a: 2-(4-((4-bromo-3-chlorophenyl)sulfonyl)piperazin-2-yl)-1,1,1-trifluoropropan-2-ol The title compound was prepared in an analogous manner to 4-bromo-3-chloro-N-((1s,3s)-3-hydroxy-3-(trifluoromethyl)cyclobutyl)benzenesulfonamide (Intermediate 1a) using 1,1,1-trifluoro-2-(piperazin-2-yl)propan-2-ol to give the title compound as a colorless solid. (UPLC-MS) $t_R$ 0.96 min; ESI-MS 453.2 [M+H]$^+$.

Intermediate 89b: 6-(2-chloro-4-((3-(1,1,1-trifluoro-2-hydroxypropan-2-yl)piperazin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 2-(4-((4-bromo-3-chlorophenyl)

sulfonyl)piperazin-2-yl)-1,1,1-trifluoropropan-2-ol (Intermediate 89a) to give the title compound. (UPLC-MS) $t_R$ 0.96 min; ESI-MS 493.4 [M+H]$^+$.

Intermediate 90a: 4-bromo-3-chloro-N-(3-chlorophenyl)benzenesulfonamide

The title compound was prepared in an analogous manner to 4-bromo-N-(3-hydroxy-3-(trifluoromethyl)cyclobutyl)-3-methylbenzenesulfonamide (Intermediate 2a) using 4-bromo-3-chlorobenzene-1-sulfonyl chloride and 3-chloroaniline I. The reaction mixture was stirred at RT for 4.5 h. The title compound was obtained as a colorless solid. (UPLC-MS) $t_R$ 1.23 min; ESI-MS 377.9/379.9/381.9 [M−H]$^-$.

Intermediate 90b: 3-chloro-N-(3-chlorophenyl)-4-(6-cyano-5-fluoropyridin-2-yl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(3-chlorophenyl)benzenesulfonamide (Intermediate 90a) to give the title compound. (UPLC-MS) $t_R$ 1.22 min; ESI-MS 422.1/242.0 [M+H]$^+$.

Intermediate 91a: 4-bromo-N-(2-hydroxycyclohexyl)-3-methylbenzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 4-bromo-3-methylbenzene-1-sulfonyl chloride and 2-aminocyclohexanol to give the title compound as a yellow solid. (UPLC-MS) $t_R$ 1.04 min; ESI-MS 346.1/348.1 [M−H]$^-$.

Intermediate 91b: 4-(6-cyano-5-fluoropyridin-2-yl)-N-(2-hydroxycyclohexyl)-3-methylbenzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1b) using 4-bromo-N-(2-hydroxycyclohexyl)-3-methylbenzenesulfonamide (Intermediate 91a) to give the title compound. (UPLC-MS) $t_R$ 1.01 min; ESI-MS 390.2 [M+H]$^+$.

Intermediate 92a: 4-bromo-3-chloro-N-(1,1-dioxidothietan-3-yl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using 3-aminothietane 1,1-dioxide to give the title compound as a colorless oil. (UPLC-MS) $t_R$ 0.89 min; ESI-MS 373.9 [M−H]$^-$.

Intermediate 92b: 3-chloro-4-(6-cyano-5-fluoropyridin-2-yl)-N-(1,1-dioxidothietan-3-yl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-(1,1-dioxidothietan-3-yl)benzenesulfonamide (Intermediate 92a) to give the title compound as a yellow solid. (UPLC-MS) $t_R$ 0.92 min; ESI-MS 414.0 [M−H]$^-$.

Intermediate 93a: 1-((4-bromo-3-chlorophenyl)sulfonyl)-3-(methylsulfonyl)azetidine The title compound was prepared in an analogous manner to 4-bromo-3-chloro-N-((1s,3s)-3-hydroxy-3-(trifluoromethyl)cyclobutyl)benzenesulfonamide (Intermediate 1a) using 3-(methylsulfonyl)azetidine to give the title compound as a colorless oil. (UPLC-MS) $t_R$ 0.93 min; no ESI ionization of parent observed.

Intermediate 93b: 6-(2-chloro-4-((3-(methylsulfonyl)azetidin-1-yl)sulfonyl)phenyl)-3-fluoropicolinonitrile The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 1-((4-bromo-3-chlorophenyl)sulfonyl)-3-(methylsulfonyl)azetidine (Intermediate 93a) to give the title compound. (UPLC-MS) $t_R$ 0.95 min; ESI-MS 432.0 [M+H]$^+$.

Intermediate 94a: 4-bromo-3-chloro-N-((1S,2S)-2-hydroxycyclopentyl)benzenesulfonamide The title compound was prepared in an analogous manner to 4-bromo-3-chloro-N-((1s,3s)-3-hydroxy-3-(trifluoromethyl)cyclobutyl)benzenesulfonamide (Intermediate 1a) using (1S,2S)-2-aminocyclopentanol to give the title compound as a colorless oil. (UPLC-MS) $t_R$ 0.93 min; ESI-MS 354.0 [M−H]$^-$.

Intermediate 94b: 3-chloro-4-(6-cyano-5-fluoropyridin-2-yl)-N-((1S,2S)-2-hydroxycyclopentyl)benzenesulfonamide The title compound was prepared in an analogous manner to 3-chloro-4-(6-cyano-5-fluoropyridin-2-yl)-N-(3-hydroxy-3-(trifluoromethyl)cyclobutyl)benzenesulfonamide (Intermediate 1 b) using 4-bromo-3-chloro-N-((1S,2S)-2-hydroxycyclopentyl)benzenesulfonamide (Intermediate 94a) to give the title compound. (UPLC-MS) $t_R$ 0.94 min; ESI-MS 394.1 [M−H]$^+$.

EXAMPLES

Example 1: 4-(3-amino-1H-pyrazolo[4,3-b]pyridin-5-yl)-3-chloro-N-((1s,3s)-3-hydroxy-3-(trifluoromethyl)cyclobutyl)benzenesulfonamide

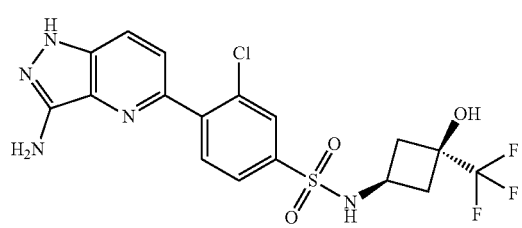 [SMILES: Nc1n[nH]c2ccc(-c3ccc(S(=O)(=O)N[C@H]4C[C@](O)(C(F)(F)F)C4)cc3Cl)nc12]

In a vial, a solution of 3-chloro-4-(6-cyano-5-fluoropyridin-2-yl)-N-((1s,3s)-3-hydroxy-3-(trifluoromethyl)cyclobutyl)benzenesulfonamide (Intermediate 1b, 148 mg, 0.29 mmol) in EtOH (2 mL) was treated with aq. hydrazine hydrate (78%, 274 μL, 4.39 mmol). The vial was sealed and the reaction mixture stirred at 80° C. for 2 h. The reaction mixture was partitioned between a sat. aq. NaHCO$_3$ solution and EtOAc. The aq. layer was extracted twice with EtOAc. The combined organic layers were dried over MgSO$_4$, filtered, and concentrated under reduced pressure. The residue was purified by silica gel column chromatography (0 to 20% MeOH in DCM) to give the title compound as a yellow solid. $^1$H NMR (400 MHz, DMSO-d6) δ ppm 11.85 (s, 1H) 8.39 (d, 1H) 7.93 (m, 1H) 7.86-7.81 (m, 3H) 7.56 (d, 1H) 6.66 (s, 1H) 5.46 (s, 2H) 3.44 (q, 1H) 2.62-2.54 (m, 2H) 2.12-2.03 (m, 2H). (UPLC-MS) t$_R$ 0.79 min; ESI-MS 462.1 [M+H]$^+$.

Example 2: 4-(3-amino-1H-pyrazolo[4,3-b]pyridin-5-yl)-N-((1s,3s)-3-hydroxy-3-(trifluoromethyl)cyclobutyl)-3-methylbenzenesulfonamide

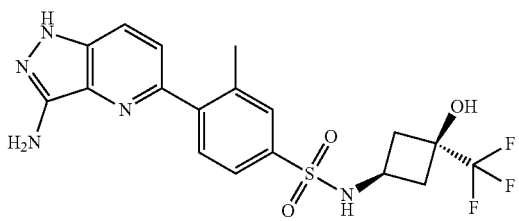 [SMILES: Cc1cc(S(=O)(=O)N[C@H]2C[C@](O)(C(F)(F)F)C2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 4-(6-cyano-5-fluoropyridin-2-yl)-N-((1s,3s)-3-hydroxy-3-(trifluoromethyl)cyclobutyl)-3-methylbenzenesulfonamide (Intermediate 2b). The reaction mixture was concentrated under reduced pressure without extractive workup. The crude product was purified by silica gel column chromatography (0 to 15% MeOH in DCM) to give the title compound as a yellow solid. $^1$H NMR (400 MHz, acetonitrile-d$_3$) δ ppm 10.03 (s, 1H), 7.84 (d, 1H), 7.80 (d, 1H), 7.75 (dd, 1H), 7.65 (d, 1H), 7.47 (d, 1H), 6.14 (d, 1H), 4.67 (s, 2H), 4.39 (s, 1H), 3.64-3.52 (m, 1H), 2.77-2.68 (m, 2H), 2.49 (s, 3H), 2.14-2.09 (m, 2H). (UPLC-MS) t$_R$ 1.26 min; API-MS 442.2 [M+H]$^+$.

Example 3: N-(4-(3-amino-1H-pyrazolo[4,3-b]pyridin-5-yl)-3-chlorophenyl)-4-chlorobenzenesulfonamide

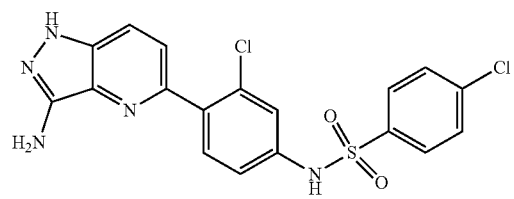 [SMILES: Nc1n[nH]c2ccc(-c3ccc(NS(=O)(=O)c4ccc(Cl)cc4)cc3Cl)nc12]

To a MW vial containing a solution of 4-chloro-N-(3-chloro-4-(6-cyano-5-fluoropyridin-2-yl)phenyl)benzenesulfonamide (Intermediate 3b, 94 mg, 0.211 mmol) in EtOH (3 mL) was added hydrazine hydrate 55% in water (0.187 mL, 2.115 mmol). The vial was sealed and the mixture was heated up and stirred at 80° C. for 6 h. The reaction was cooled down to RT and concentrated under reduced pressure without any extracting workup. The residue was purified by silica gel column chromatography (0 to 3% MeOH in DCM) to afford the title product as pale yellow solid. $^1$H NMR (400 MHz, DMSO-d6) δ ppm 11.72 (s, 1H) 10.79 (br s, 1H) 7.84 (d, 2H) 7.74 (d, 1H) 7.69 (d, 2H) 7.48 (d, 1H) 7.41 (d, 1H) 7.24 (d, 1H) 7.18 (dd, 1H) 5.36 (s, 2H). (UPLC-MS) t$_R$ 0.92 min; ESI-MS 434.1/436.1 [M+H]$^+$; ESI-MS 432.1/434.1 [M−H]$^-$.

Example 4: 4-(3-amino-1H-pyrazolo[4,3-b]pyridin-5-yl)-3-chloro-N-(3,3-difluorocyclobutyl)benzenesulfonamide

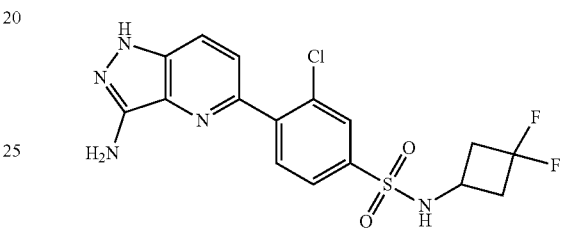

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(3,3-difluorocyclobutyl)benzenesulfonamide (Intermediate 4b). $^1$H NMR (400 MHz, DMSO-d$_6$) δ ppm 11.85 (s, 1H) 8.41 (d, 1H) 7.95 (d, 1H) 7.89-7.81 (m, 3H) 7.57 (d, 1H) 5.45 (s, 2H) 3.61-3.72 (m, 1H) 2.89-2.75 (m, 2H) 2.54-2.38 (m, 2H). (UPLC-MS) t$_R$ 0.82 min; ESI-MS 414.2 [M+H]$^+$; ESI-MS 412.2 [M−H]$^-$.

Example 5: N-(4-(3-amino-1H-pyrazolo[4,3-b]pyridin-5-yl)-3-chlorophenyl)-4-methoxybenzenesulfonamide

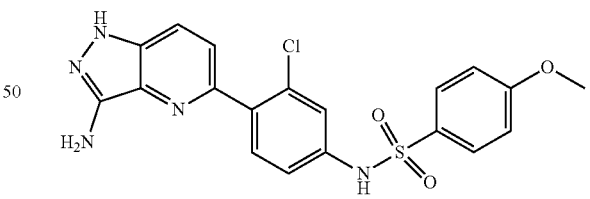

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-4-methoxybenzenesulfonamide (Intermediate 5b) at 80° C. for 4.5 h. The residue was purified by reverse phase column chromatography (Method 2) (10% to 30% ACN in water). A second purification using silica gel column chromatography (0 to 3% MeOH in DCM) afforded the title compound as pale yellow solid. $^1$H NMR (400 MHz, DMSO-d$_6$) δ ppm 11.71 (s, 1H) 10.57 (br s, 1H) 7.75-7.80 (m, 2H) 7.73 (d, 1H) 7.46 (d, 1H) 7.40 (d, 1H) 7.24 (d, 1H) 7.18 (dd, 1H) 7.12 (m, 2H) 5.35 (s, 2H) 3.82 (s, 3H). (UPLC-MS) $t_R$ 0.83 min; ESI-MS 430.2 [M+H]$^+$; ESI-MS 428.2 [M–H]$^-$.

Example 6: N-(4-(3-amino-1H-pyrazolo[4,3-b]pyridin-5-yl)-3-chlorophenyl)-4-fluorobenzenesulfonamide

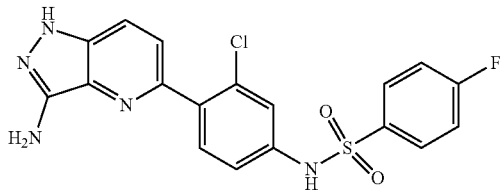 [SMILES: Nc1n[nH]c2ccc(-c3ccc(NS(=O)(=O)c4ccc(F)cc4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-4-fluorobenzenesulfonamide (Intermediate 6b) at 80° C. for 6 h. The residue was purified by silica gel column chromatography (0 to 3% MeOH in DCM) to afford the title compound as yellow solid. $^1$H NMR (400 MHz, DMSO-d$_6$) δ ppm 11.72 (s, 1H) 10.73 (br s, 1H) 7.90 (m, 2H) 7.74 (d, 1H) 7.50-7.43 (m, 3H) 7.41 (d, 1H) 7.24 (d, 1H) 7.18 (dd, 1H) 5.35 (s, 2H). (UPLC-MS) $t_R$ 0.85 min; ESI-MS 418.1 [M+H]$^+$; ESI-MS 416.1 [M–H]$^-$.

Example 7: 4-(3-amino-1H-pyrazolo[4,3-b]pyridin-5-yl)-3-chloro-N-((1R,2S)-2-hydroxycyclopentyl)benzenesulfonamide

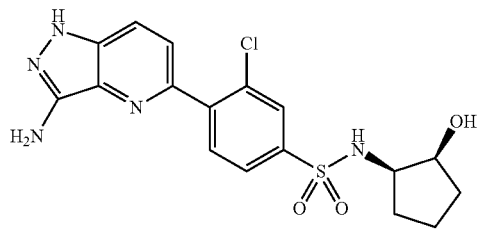 [SMILES: Nc1n[nH]c2ccc(-c3ccc(S(=O)(=O)N[C@@H]4CCC[C@@H]4O)cc3Cl)nc12]

In a vial, a solution of 3-chloro-4-(6-cyano-5-fluoropyridin-2-yl)-N-((1R,2S)-2-hydroxycyclopentyl)benzenesulfonamide (Intermediate 7b, 55 mg, 0.14 mmol) in THF (2 mL) was treated with hydrazine anhydrous (1M solution in THF, 0.70 mL, 0.70 mmol). The vial was sealed and the reaction mixture stirred at 80° C. for 1 h. The reaction mixture was concentrated under reduced pressure and the residue was purified by silica gel column chromatography (0 to 4% MeOH in DCM) to afford the title compound as a yellow solid. $^1$H NMR (400 MHz, DMSO-d6) b ppm 11.83 (br s, 1H) 8.02 (d, 1H) 7.90 (dd, 1H) 7.81 (dd, 2H) 7.60-7.54 (m, 2H) 5.45 (br s, 2H) 4.71 (d, 1H) 3.84-3.77 (m, 1H) 3.41-3.33 (m, 1H) 1.70-1.56 (m, 2H) 1.52-1.34 (m, 4H). (UPLC-MS) $t_R$ 0.70 min; ESI-MS 408.1 [M+H]$^+$; ESI-MS 414.2 [M+H]$^+$; ESI-MS 406.1 [M–H]$^-$.

Example 8: 4-(3-amino-1H-pyrazolo[4,3-b]pyridin-5-yl)-N-(3,3-difluorocyclobutyl)-3-methylbenzenesulfonamide

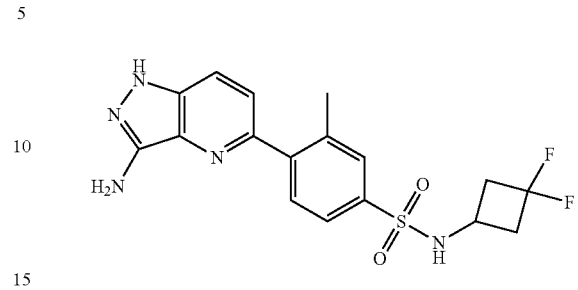

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 4-(6-cyano-5-fluoropyridin-2-yl)-N-(3,3-difluorocyclobutyl)-3-methylbenzenesulfonamide (Intermediate 8b). $^1$H NMR (400 MHz, DMSO-d$_6$) δ ppm 11.76 (br s, 1H) 8.18 (d, 1H) 7.81 (d, 1H) 7.74 (s, 1H) 7.71 (br d, 1H) 7.65-7.61 (m, 1H) 7.45 (d, 1H) 5.41 (s, 2H) 3.61 (quin, 1H) 2.85-2.71 (m, 2H) 2.44 (s, 3H) 2.48-2.38 (m, 2H). (UPLC-MS) $t_R$ 0.78 min; ESI-MS 394.2 [M+H]$^+$; ESI-MS 392.2 [M–H]$^-$.

Example 9: 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide

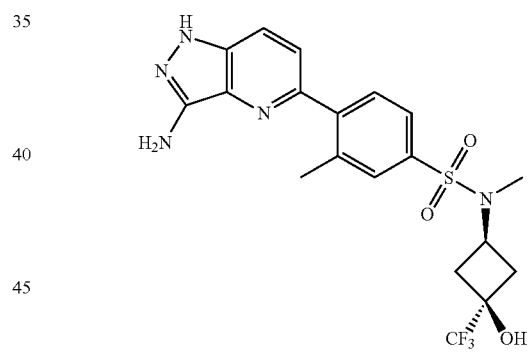

In a vial, a solution of 4-(6-cyano-5-fluoropyridin-2-yl)-N-((1s,3s)-3-hydroxy-3-(trifluoromethyl)cyclobutyl)-N,3-dimethylbenzenesulfonamide (Intermediate 9b, 1.50 g, 2.37 mmol) in EtOH (20 mL) was treated with aq. hydrazine hydrate (78%, 2.21 mL, 35.5 mmol). The vial was sealed and the reaction mixture stirred at 80° C. for 60 min. The reaction mixture was partitioned between a sat. aq. NaHCO$_3$ solution and EtOAc. The aq. layer was extracted twice with EtOAc. The combined organic layers were dried over MgSO$_4$, filtered, and concentrated under reduced pressure. The residue was purified by silica gel column chromatography (0 to 20% MeOH in DCM) and by reverse phase column chromatography (Method 2) (5% to 50% ACN in water) to give the title compound as an off-white solid. The stereo-configuration of the title compound was determined by X-ray crystallography. $^1$H NMR (400 MHz, DMSO-d$_6$) δ ppm 11.79 (5, 1H) 7.82 (d, 1H) 7.69 (d, 3H) 7.47 (d, 1H) 6.72 (s, 1H) 5.45 (br s, 2H) 3.75 (quin, 1H) 2.71 (s, 3H)

2.66-2.58 (m, 2H) 2.47 (s, 3H) 2.38-2.32 (m, 2H). (UPLC-MS) $t_R$ 0.81 min; ESI-MS 456.2 [M+H]$^+$ ESI-MS 454.2 [M−H]$^−$.

Example 10: N-(4-(3-amino-1H-pyrazolo[4,3-b]pyridin-5-yl)-3-chlorophenyl)-3,4-difluorobenzenesulfonamide

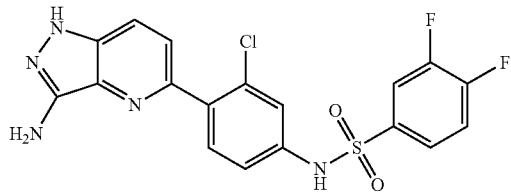 [SMILES: Nc1n[nH]c2ccc(-c3ccc(NS(=O)(=O)c4ccc(F)c(F)c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3,4-difluorobenzenesulfonamide (Intermediate 10b) at 80° C. for 1.5 h. The residue was purified twice by silica gel column chromatography (0 to 4% MeOH in DCM) to afford the title compound as yellow solid. $^1$H NMR (600 MHz, DMSO-d6) δ ppm 11.75 (s, 1H) 10.84 (s, 1H) 7.93 (m, 1H) 7.75 (d, 1H) 7.70-7.73 (m, 2H) 7.50 (d, 1H) 7.42 (d, 1H) 7.26 (d, 1H) 7.21 (dd, 1H) 5.38 (br s, 2H). (UPLC-MS) $t_R$ 0.88 min; ESI-MS 436.1 [M+H]$^+$; ESI-MS 434.1 [M−H]$^−$.

Example 11: N-(4-(3-amino-1H-pyrazolo[4,3-b]pyridin-5-yl)-3-chlorophenyl)benzo[d][1,3]dioxole-5-sulfonamide

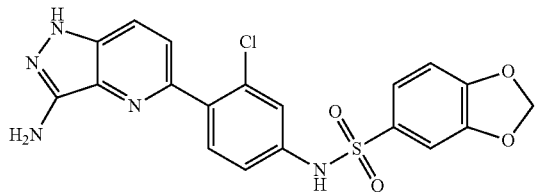 [SMILES: Nc1n[nH]c2ccc(-c3ccc(NS(=O)(=O)c4ccc5c(c4)OCO5)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)benzo[d][1,3]dioxole-5-sulfonamide (Intermediate 11b) at 80° C. for 2 h. The residue was purified twice by normal phase column chromatography (0 to 3% MeOH in DCM) to afford the title compound as pale yellow solid. $^1$H NMR (400 MHz, DMSO-d6) δ ppm 11.72 (s, 1H) 10.58 (s, 1H) 7.74 (d, 1H) 7.48 (d, 1H) 7.37-7.44 (m, 2H) 7.28 (d, 1H) 7.25 (d, 1H) 7.20 (dd, 1H) 7.08 (d, 1H) 6.16 (s, 2H) 5.36 (s, 2H). (UPLC-MS) $t_R$ 0.83 min; ESI-MS 444.1 [M+H]$^+$; ESI-MS 442.1 [M−H]$^−$.

Example 12: 4-(3-amino-1H-pyrazolo[4,3-b]pyridin-5-yl)-3-chloro-N-(2-hydroxycyclohexyl)benzenesulfonamide

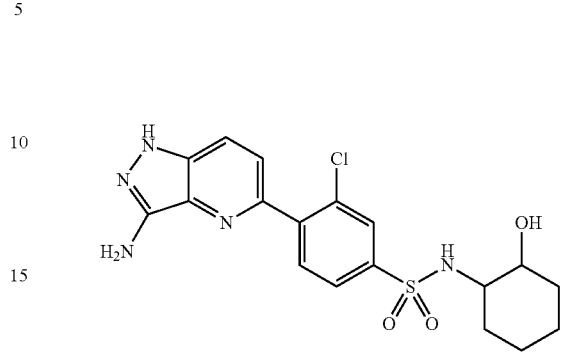

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 3-chloro-4-(6-cyano-5-fluoropyridin-2-yl)-N-(2-hydroxycyclohexyl)benzenesulfonamide (Intermediate 12b). $^1$H NMR (400 MHz, DMSO-d$_6$) δ ppm 11.83 (s, 1H) 8.01 (d, 1H) 7.89 (dd, 1H) 7.81 (dd, 2H) 7.60 (d, 1H) 7.55 (d, 1H) 5.45 (br s, 2H) 4.60 (d, 1H) 3.66-3.59 (m, 1H) 3.20-3.10 (m, 1H) 1.66-1.32 (m, 5H) 1.26-1.09 (m, 3H). (UPLC-MS) $t_R$ 0.76 min; ESI-MS 422.1 [M+H]$^+$; ESI-MS 420.2 [M−H]$^−$.

Example 13: N-(4-(3-amino-1H-pyrazolo[4,3-b]pyridin-5-yl)-3-chlorophenyl)-4-chloro-3-fluorobenzenesulfonamide

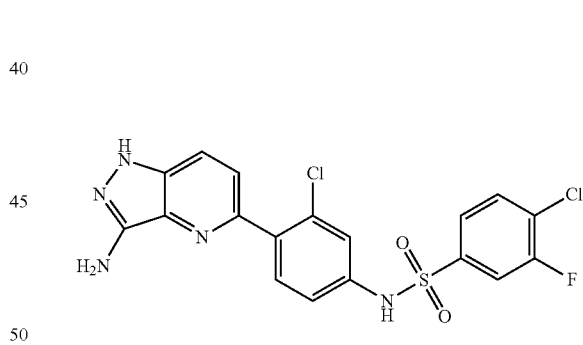

The title compound was prepared in an analogous manner to N-(4-(3-amino-1H-pyrazolo[4,3-b]pyridin-5-yl)-3-chlorophenyl)-4-chlorobenzenesulfonamide (Example 3) using 4-chloro-N-(3-chloro-4-(6-cyano-5-fluoropyridin-2-yl)phenyl)-3-fluorobenzenesulfonamide (Intermediate 13b) at 80° C. for 2 h. The residue was purified by preparative HPLC (Method 3, 5% to 50% ACN (+7.3 mM NH$_4$OH) in water (+7.3 mM NH$_4$OH)). A second purification by silica gel column chromatography (0 to 2% MeOH in DCM) afforded the title compound as pale yellow solid. $^1$H NMR (400 MHz, DMSO-d$_6$) δ ppm 11.73 (s, 1H) 10.87 (br s, 1H) 7.92-7.83 (m, 2H) 7.75 (d, 1H) 7.68 (dd, 1H) 7.51 (d, 1H) 7.42 (d, 1H) 7.26 (d, 1H) 7.21 (dd, 1H) 5.36 (s, 2H). (UPLC-MS) $t_R$ 0.95 min; ESI-MS 452.1 [M+H]$^+$; ESI-MS 450.0 [M−H]$^−$.

Example 14: (1S,2R)-N-(4-(3-amino-1H-pyrazolo[4,3-b]pyridin-5-yl)-3-chlorophenyl)-2-hydroxycyclohexane-1-sulfonamide

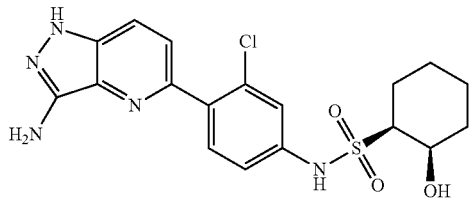 [SMILES: Nc1n[nH]c2ccc(-c3ccc(NS(=O)(=O)[C@H]4CCCC[C@H]4O)cc3Cl)nc12]

The title compound was obtained by chiral separation of N-(4-(3-amino-1H-pyrazolo[4,3-b]pyridin-5-yl)-3-chlorophenyl)-2-hydroxycyclohexane-1-sulfonamide (Example 17) using SEPIATEC ASAP HPLC System (column Chiralpak AD-H, 5□m, 250×20 mm; mobile phase: n-heptane:EtOH:MeOH 70:15:15 (v:v:v)+0.1% DEA; flowrate 10 mL/min; detection 270 nm) to afford the title compound. $^1$H NMR (400 MHz, DMSO-d6) δ ppm 11.72 (s, 1H), 9.62 (s, 1H), 7.75 (d, 1H), 7.53 (d, 1H), 7.45 (d, 1H), 7.35 (d, 1H), 7.28 (dd, 1H), 5.34 (s, 2H), 5.05 (d, 1H), 3.77 (s, 1H), 3.01-2.91 (m, 1H), 2.05 (d, 1H), 1.88 (d, 1H), 1.65 (d, 2H), 1.47 (d, 1H), 1.33-1.12 (m, 4H). (UPLC-MS) $t_R$ 0.78 min; ESI-MS 422.1 [M+H]$^+$; ESI-MS 420.1 [M−H]$^−$.

Example 15: N-(4-(3-amino-1H-pyrazolo[4,3-b]pyridin-5-yl)-3-chlorophenyl)cyclohexanesulfonamide

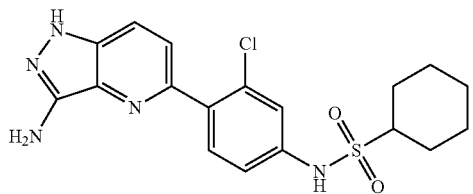 [SMILES: Nc1n[nH]c2ccc(-c3ccc(NS(=O)(=O)C4CCCCC4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)cyclohexanesulfonamide (Intermediate 15b) at 80° C. for 7 hr. The crude material was first purified by silica gel column chromatography (0% to 3% MeOH in DCM). A second purification by preparative HPLC (Method 1, 5% to 95% ACN in water (+0.1% TFA)) was performed. A third purification by silica gel column chromatography (0 to 4% MeOH in DCM) afforded the title compound as yellow solid. $^1$H NMR (400 MHz, DMSO-d6) δ ppm 11.74 (s, 1H) 10.12 (s, 1H) 7.77 (d, 1H) 7.55 (d, 1H) 7.47 (d, 1H) 7.37 (d, 1H) 7.30 (dd, 1H) 5.35 (s, 2H) 3.11 (tt, 1H) 2.09-2.02 (m, 2H) 1.82-1.73 (m, 2H) 1.60 (dq, 1H) 1.51-1.38 (m, 2H) 1.32-1.19 (m, 2H) 1.19-1.07 (m, 1H). (UPLC-MS) $t_R$ 0.88 min; ESI-MS 406.1 [M+H]$^+$; ESI-MS 404.2 [M−H]$^−$.

Example 16: 4-(3-amino-1H-pyrazolo[4,3-b]pyridin-5-yl)-3-methyl-N-phenylbenzenesulfonamide

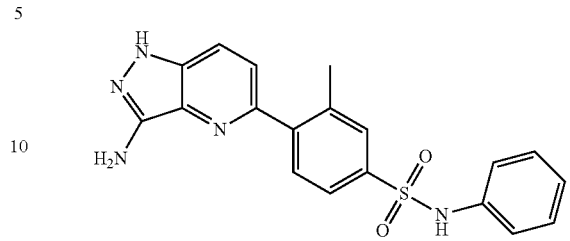

In a vial, a solution of 4-(6-cyano-5-fluoropyridin-2-yl)-3-methyl-N-phenylbenzenesulfonamide (Intermediate 16b, 30 mg, 0.039 mmol) in aq. hydrazine hydrate (64%, 0.10 mL, 3.15 mmol) was stirred at 100° C. for 80 min. The reaction mixture was partitioned between a sat. aq. NaHCO$_3$ solution and EtOAc. The organic layer was washed three times with water and once with brine, then dried over MgSO$_4$, filtered, and concentrated under reduced pressure. The residue was purified by reverse phase column chromatography (Method 2, 2 to 100% ACN in water) to afford the title compound as an off-white solid. $^1$H NMR (400 MHz, DMSO-d6) δ ppm 11.73 (s, 1H) 10.31 (s, 1H) 7.77 (d, 1H) 7.73-7.69 (m, 1H) 7.66 (dd, 1H) 7.55 (d, 1H) 7.40 (d, 1H) 7.28-7.22 (m, 2H) 7.17-7.15 (m, 1H) 7.15-7.12 (m, 1H) 7.07-7.00 (m, 1H) 5.40 (br s, 2H) 2.35 (s, 3H). (UPLC-MS) $t_R$ 0.85 min; ESI-MS 380.1 [M+H]$^+$; ESI-MS 378.2 [M−H]$^−$.

Example 17: N-(4-(3-amino-1H-pyrazolo[4,3-b]pyridin-5-yl)-3-chlorophenyl)-2-hydroxycyclohexane-1-sulfonamide

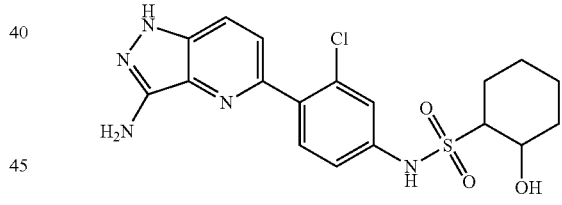

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-2-hydroxycyclohexane-1-sulfonamide (Intermediate 17b) at 80° C. for 2 h. The reaction was quenched with a sat. aq. NaHCO$_3$ solution and extracted twice with EtOAc. The combined organic layers were dried over MgSO$_4$, filtered and evaporated under reduced pressure. The residue was purified first using silica gel column chromatography (0 to 20% MeOH in DCM). Second purification by reverse phase column chromatography (Method 2) (2 to 100% ACN in water). A third purification by normal phase column chromatography (0 to 4% MeOH in DCM) afforded the title compound as beige foam. $^1$H NMR (400 MHz, DMSO-d6) δ ppm 11.73 (s, 1H) 9.64 (br s, 1H) 7.77 (d, 1H) 7.54 (d, 1H) 7.47 (d, 1H) 7.37 (d, 1H) 7.29 (dd, 1H) 5.35 (s, 2H) 5.07 (br s, 1H) 3.83-3.75 (m, 1H) 2.92-3.03 (m, 1H) 2.11-2.02 (m, 1H) 1.94-1.86 (m, 1H) 1.74-1.65 (m, 1H) 1.65-1.58 (m, 1H)

1.54-1.42 (m, 1H) 1.31-1.17 (m, 3H). (UPLC-MS) $t_R$ 0.79 min; ESI-MS 422.2 [M+H]⁺; ESI-MS 420.1 [M−H]⁻.

Example 18: (S)-(1-((4-(3-amino-1H-pyrazolo[4,3-b]pyridin-5-yl)-3-chlorophenyl)sulfonyl)-4,4-difluoropyrrolidin-2-yl)methanol

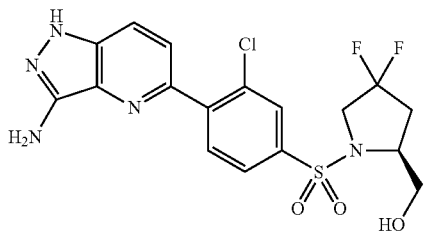 [SMILES: Nc1n[nH]c2ccc(-c3ccc(S(=O)(=O)N4CC(F)(F)C[C@H]4CO)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using (S)-6-(2-chloro-4-((4,4-difluoro-2-(hydroxymethyl)pyrrolidin-1-yl)sulfonyl)phenyl)-3-fluoropicolinonitrile (Intermediate 18b). The reaction mixture was concentrated under reduced pressure without extractive workup. The crude product was purified by silica gel column chromatography (0 to 25% MeOH in DCM) to afford the title compound as a yellow solid. ¹H NMR (400 MHz, acetonitrile-d₃) δ ppm 10.11 (s, 1H), 8.04 (d, 1H), 7.91 (dd, 1H), 7.88-7.84 (m, 2H), 7.64 (d, 1H), 4.68 (s, 2H), 3.99 (dtd, 1H), 3.89 (dddd, 1H), 3.77 (dq, 2H), 3.72-3.66 (m, 1H), 3.20 (t, 1H), 2.52-2.31 (m, 2H). (UPLC-MS) $t_R$ 1.23 min; API-MS 444.2 [M+H]⁺.

Example 19: 4-(3-amino-1H-pyrazolo[4,3-b]pyridin-5-yl)-N-((1R,3S)-3-hydroxycyclopentyl)-3-methylbenzenesulfonamide

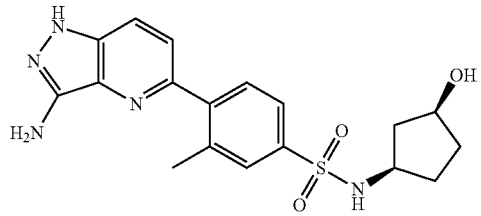 [SMILES: Cc1cc(S(=O)(=O)N[C@@H]2CC[C@H](O)C2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 4-(6-cyano-5-fluoropyridin-2-yl)-N-((1R,3S)-3-hydroxycyclopentyl)-3-methylbenzenesulfonamide (Intermediate 19b). ¹H NMR (400 MHz, DMSO-d6) δ ppm 11.75 (s, 1H) 7.80 (d, 1H) 7.74 (s, 1H) 7.73-7.69 (m, 1H) 7.67 (d, 1H) 7.60 (d, 1H) 7.44 (d, 1H) 5.42 (s, 2H) 4.57 (d, 1H) 3.97-3.88 (m, 1H) 3.44-3.37 (m, 1H) 2.43 (s, 3H) 1.98-1.89 (m, 1H) 1.66-1.39 (m, 4H) 1.29-1.20 (m, 1H). (UPLC-MS) $t_R$ 0.67 min; ESI-MS 388.3 [M+H]⁺; ESI-MS 368.3 [M−H]⁻.

Example 20: 4-(3-amino-1H-pyrazolo[4,3-b]pyridin-5-yl)-N-((1R,2S)-2-hydroxycyclopentyl)-3-methylbenzenesulfonamide

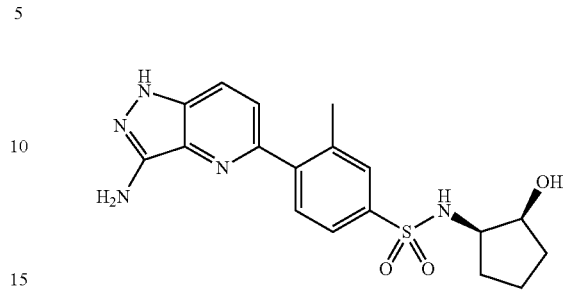

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 4-(6-cyano-5-fluoropyridin-2-yl)-N-((1R,2S)-2-hydroxycyclopentyl)-3-methylbenzene sulfonamide (Intermediate 20b). ¹H NMR (400 MHz, DMSO-d6) δ ppm 11.74 (br s, 1H) 7.82-7.78 (m, 2H) 7.75 (dd, 1H) 7.58 (d, 1H) 7.44 (d, 1H) 7.27 (d, 1H) 5.41 (br s, 2H) 4.63 (d, 1H) 3.83-3.76 (m, 1H) 3.30-3.25 (m, 1H) 2.42 (s, 3H) 1.69-1.54 (m, 2H) 1.51-1.28 (m, 4H). (UPLC-MS) $t_R$ 0.70 min; ESI-MS 388.1 [M+H]⁺; ESI-MS 386.1 [M−H]⁻.

Example 21: 5-(4-((hexahydrocyclopenta[c]pyrrol-2(1H)-yl)sulfonyl)-2-methylphenyl)-1H-pyrazolo[4,3-b]pyridin-3-amine

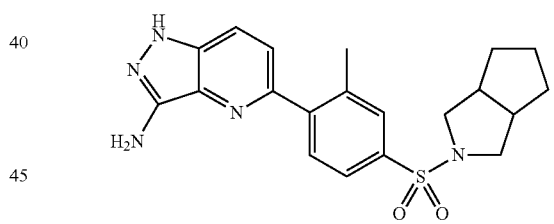

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 3-fluoro-6-(4-((hexahydrocyclopenta[c]pyrrol-2(1H)-yl)sulfonyl)-2-methylphenyl) picolinonitrile (Intermediate 21b). The product was further purified by preparative HPLC (Method 1, 5 to 95% ACN in water (+0.1% TFA)). Fractions containing pure product were combined and passed through a PL-HCO3 MP cartridge (Stratospheres, pre-conditioned with MeOH), following by washout with MeOH. The filtrate was concentrated under reduced pressure to afford the title compound as an off-white solid. ¹H NMR (400 MHz, DMSO-d₆) δ ppm 11.77 (br s, 1H) 7.81 (d, 1H) 7.70 (s, 1H) 7.66 (s, 2H) 7.46 (d, 1H) 5.42 (br s, 2H) 3.12 (m, 2H) 2.85 (dd, 2H) 2.58-2.52 (m, 2H) 2.45 (s, 3H) 1.75-1.64 (m, 2H) 1.58-1.37 (m, 2H) 1.36-1.27 (m, 2H). (UPLC-MS) $t_R$ 0.96 min; ESI-MS 398.3 [M+H]⁺; ESI-MS 396.2 [M−H]⁻.

Example 22: N-(4-(3-amino-1H-pyrazolo[4,3-b]pyridin-5-yl)-3-chlorophenyl)-3-cyanobenzenesulfonamide

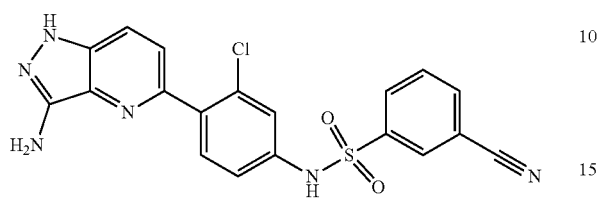

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3-cyanobenzenesulfonamide (Intermediate 22b) at 80° C. for 2.5 h. The residue was purified by reverse phase column chromatography (Method 2, 10% to 35% ACN in water). A second purification using silica gel column chromatography (0 to 3% MeOH in DCM) afforded the title product as pale yellow solid. $^1$H NMR (400 MHz, DMSO-d6) δ ppm 11.73 (s, 1H) 10.89 (br s, 1H) 8.28 (s, 1H) 8.18-8.10 (m, 2H) 7.84 (t, 1H) 7.74 (d, 1H) 7.50 (d, 1H) 7.41 (d, 1H) 7.25 (d, 1H) 7.21 (dd, 1H) 5.36 (s, 2H). (UPLC-MS) $t_R$ 0.82 min; ESI-MS 425.1 [M+H]$^+$; ESI-MS 423.1 [M−H]$^−$.

Example 23: 4-(3-amino-1H-pyrazolo[4,3-b]pyridin-5-yl)-3-chloro-N-((1R,3S)-3-hydroxycyclopentyl)benzenesulfonamide

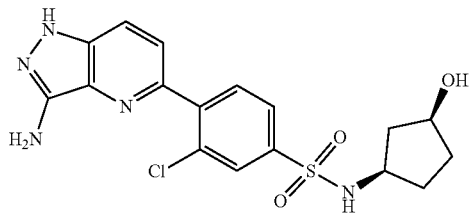 [SMILES: Nc1n[nH]c2ccc(-c3ccc(S(=O)(=O)N[C@@H]4CC[C@H](O)C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-((1R,3S)-3-hydroxycyclopentyl)benzenesulfonamide (Intermediate 23b). $^1$H NMR (400 MHz, DMSO-d6) b ppm 11.85 (s, 1H), 8.03-7.78 (m, 5H), 7.58 (d, 1H), 5.47 (s, 2H), 4.61 (d, 1H), 3.95 (s, 1H), 3.47 (q, 1H), 3.18 (d, 1H), 1.97 (dt, 1H), 1.79-1.39 (m, 4H), 1.38-1.19 (m, 2H). (UPLC-MS) $t_R$ 0.67 min; ESI-MS 408.2 [M+H]$^+$; ESI-MS 406.2 [M−H]$^−$.

Example 24: 4-(3-amino-1H-pyrazolo[4,3-b]pyridin-5-yl)-3-chloro-N-(4,4-dimethylcyclohexyl)benzenesulfonamide

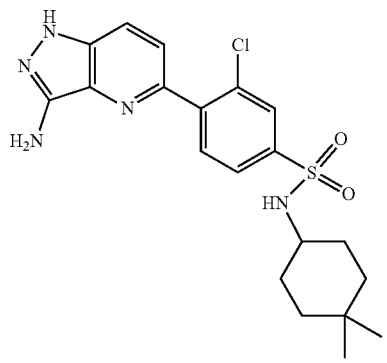 [SMILES: CC1(C)CCC(NS(=O)(=O)c2ccc(-c3ccc4[nH]nc(N)c4n3)c(Cl)c2)CC1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) except 3-chloro-4-(6-cyano-5-fluoropyridin-2-yl)-N-(4,4-dimethylcyclohexyl)benzenesulfonamide (Intermediate 24b) was used in place of 3-chloro-4-(6-cyano-5-fluoropyridin-2-yl)-N-(3-hydroxy-3-(trifluoromethyl)cyclobutyl)benzenesulfonamide (Intermediate 1b). $^1$H NMR (400 MHz, DMSO-d6) δ ppm 11.82 (s, 1H), 7.93 (d, 1H), 7.88-7.78 (m, 4H), 7.55 (d, 1H), 5.43 (s, 2H), 2.98 (s, 1H), 1.52-1.42 (m, 2H), 1.42-1.19 (m, 5H), 1.17-1.03 (m, 2H), 0.82 (d, 6H). (UPLC-MS) $t_R$ 1.04 min; ESI-MS 434.2 [M+H]$^+$.

Example 25: N-(4-(3-amino-1H-pyrazolo[4,3-b]pyridin-5-yl)-3-chlorophenyl)-4-methylbenzenesulfonamide

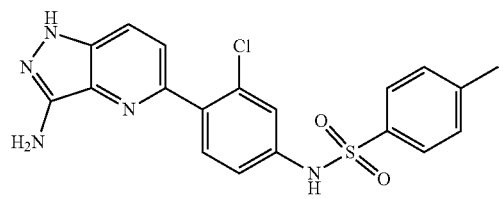 [SMILES: Cc1ccc(S(=O)(=O)Nc2ccc(-c3ccc4[nH]nc(N)c4n3)c(Cl)c2)cc1]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-4-methylbenzenesulfonamide (Intermediate 25b) at 80° C. for 2 h. The residue was purified by silica gel column chromatography (0 to 4% MeOH in DCM). A second purification by preparative HPLC (Method 1, 5% to 95% ACN in water (+0.1% TFA)) afforded the title compound as pale yellow solid. $^1$H NMR (400 MHz, DMSO-d6) δ ppm 11.71 (s, 1H) 10.64 (s, 1H) 7.76-7.70 (m, 3H) 7.46 (d, 1H) 7.40 (d, 3H) 7.24 (d, 1H) 7.18 (dd, 1H) 5.35 (s, 2H) 2.36 (s, 3H). (UPLC-MS) $t_R$ 0.89 min; ESI-MS 414.2 [M+H]$^+$; ESI-MS 412.1 [M−H]$^−$.

Example 26: 4-(3-amino-1H-pyrazolo[4,3-b]pyridin-5-yl)-N-(1-(hydroxymethyl)cyclopentyl)-3-methylbenzenesulfonamide

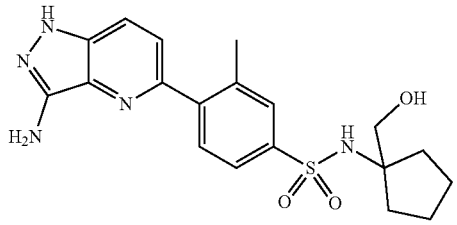 [SMILES: Cc1cc(S(=O)(=O)NC2(CO)CCCC2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 4-(6-cyano-5-fluoropyridin-2-yl)-N-(1-(hydroxymethyl)cyclopentyl)-3-methylbenzenesulfonamide (Intermediate 26b). The product was further purified by preparative HPLC (Method 1, 5 to 95% ACN in water (+0.1% TFA)). Fractions containing pure product were combined and passed through a PL-HCO3 MP cartridge (Stratospheres, pre-conditioned with MeOH), following by washout with MeOH. The filtrate was concentrated under reduced pressure to afford the title compound as a yellow solid. $^1$H NMR (400 MHz, DMSO-d6) δ ppm 11.74 (br s, 1H) 7.80 (d, 1H) 7.75 (br s, 1H) 7.74-7.70 (m, 1H) 7.58 (d, 1H) 7.45-7.41 (m, 2H) 5.42 (br s, 2H) 4.72 (t, 1H) 3.37 (d, 2H) 2.42 (s, 3H) 1.79-1.68 (m, 2H) 1.66-1.54 (m, 2H) 1.49-1.34 (m, 4H). (UPLC-MS) $t_R$ 0.70 min; ESI-MS 402.3 [M+H]$^+$; ESI-MS 400.2 [M–H]$^-$.

Example 27: N-(4-(3-amino-1H-pyrazolo[4,3-b]pyridin-5-yl)-3-chlorophenyl)-3-chloro-4-fluorobenzenesulfonamide

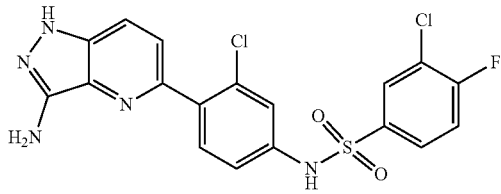 [SMILES: Nc1n[nH]c2ccc(-c3ccc(NS(=O)(=O)c4ccc(F)c(Cl)c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using 3-chloro-N-(3-chloro-4-(6-cyano-5-fluoropyridin-2-yl)phenyl)-4-fluorobenzenesulfonamide (Intermediate 27b) at 80° C. for 2 h. The residue was purified by reverse phase column chromatography (Method 2, 10% to 45% ACN in water). The product was purified by silica gel column chromatography (0 to 3% MeOH in DCM) to afford the title compound as pale yellow solid. $^1$H NMR (600 MHz, DMSO-d6) δ ppm 11.75 (s, 1H) 10.84 (s, 1H) 8.06-8.03 (m, 1H) 7.83-7.87 (m, 1H) 7.75 (d, 1H) 7.68 (t, 1H) 7.51 (d, 1H) 7.42 (d, 1H) 7.26 (d, 1H) 7.21 (dd, 1H) 5.38 (br s, 2H). (UPLC-MS) $t_R$ 0.93 min; ESI-MS 452.1/454.0 [M+H]$^+$; ESI-MS 450.1/452.1 [M–H]$^-$.

Example 28: N-(4-(3-amino-1H-pyrazolo[4,3-b]pyridin-5-yl)-3-chlorophenyl)-3-chlorobenzenesulfonamide

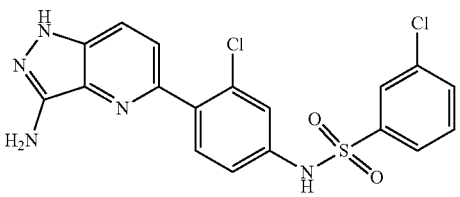 [SMILES: Nc1n[nH]c2ccc(-c3ccc(NS(=O)(=O)c4cccc(Cl)c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using 3-chloro-N-(3-chloro-4-(6-cyano-5-fluoropyridin-2-yl)phenyl)benzenesulfonamide (Intermediate 28b) at 80° C. for 3.5 h. The crude material was purified by reverse phase column chromatography (Method 2, 5% to 45% ACN in water). The product was further purified by silica gel column chromatography (0 to 3% MeOH in DCM) to afford the title compound as yellow solid. $^1$H NMR (400 MHz, DMSO-d$_6$) δ ppm 11.73 (s, 1H) 10.81 (s, 1H) 7.85 (t, 1H) 7.82-7.72 (m, 3H) 7.65 (t, 1H) 7.50 (d, 1H) 7.41 (d, 1H) 7.25 (d, 1H) 7.20 (dd, 1H) 5.36 (s, 2H). (UPLC-MS) $t_R$ 0.91 min; ESI-MS 434.1/436.1 [M+H]$^+$; ESI-MS 432.1/434.1 [M–H]$^-$.

Example 29: 4-(3-amino-1H-pyrazolo[4,3-b]pyridin-5-yl)-3-chloro-N-((1R,2R)-2-hydroxycyclopentyl)benzenesulfonamide

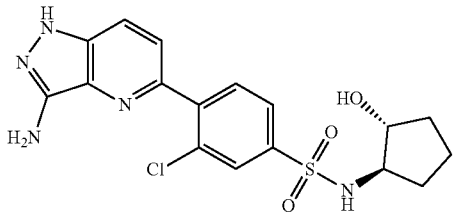 [SMILES: Nc1n[nH]c2ccc(-c3ccc(S(=O)(=O)N[C@@H]4CCC[C@H]4O)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-((1R,2R)-2-hydroxycyclopentyl)benzenesulfonamide (Intermediate 29b). $^1$H NMR (400 MHz, DMSO-d6) δ ppm 11.84 (br s, 1H) 7.96 (d, 1H) 7.89-7.85 (m, 1H) 7.85-7.78 (m, 3H) 7.56 (d, 1H) 5.46 (br s, 2H) 4.74 (d, 1H) 3.84-3.77 (m, 1H) 3.24 (br s, 1H) 1.81-1.70 (m, 2H) 1.60-1.50 (m, 2H) 1.43-1.25 (m, 2H). (UPLC-MS) $t_R$ 0.67 min; ESI-MS 408.2 [M+H]$^+$; ESI-MS 406.1 [M–H]$^-$.

Example 30: 4-(3-amino-1H-pyrazolo[4,3-b]pyridin-5-yl)-3-chloro-N-(1-(hydroxymethyl)cyclopentyl)benzenesulfonamide

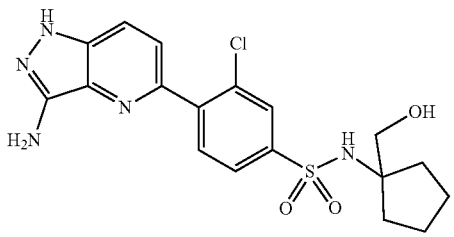 [SMILES: Nc1n[nH]c2ccc(-c3ccc(S(=O)(=O)NC4(CO)CCCC4)cc3Cl)nc12]

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 3-chloro-4-(6-cyano-5-fluoropyridin-2-yl)-N-(1-(hydroxymethyl)cyclopentyl)benzene sulfonamide (Intermediate 30b). The product was further purified by preparative HPLC (Method 1, 5 to 95% ACN in water (+0.1% TFA)). Fractions containing pure product were combined, solid NaHCO$_3$ was added, acetonitrile was evaporated under reduced pressure, and the resulting aqueous layer was extracted three times with DCM. The combined organic layers were washed with brine, dried over anhydrous MgSO$_4$, filtered and concentrated under reduced pressure to afford the title compound as a yellow solid. $^1$H NMR (400 MHz, DMSO-d6) δ ppm 11.83 (br s, 1H) 7.97 (d, 1H) 7.89-7.85 (m, 1H) 7.84-7.77 (m, 2H) 7.67 (s, 1H) 7.55 (d, 1H) 5.46 (br s, 2H) 4.78 (t, 1H) 3.36 (d, 2H) 1.78-1.70 (m, 2H) 1.67-1.57 (m, 2H) 1.51-1.37 (m, 4H). (UPLC-MS) t$_R$ 0.74 min; ESI-MS 422.2 [M+H]$^+$; ESI-MS 420.2 [M−H]$^−$.

Example 31: 4-(3-amino-1H-pyrazolo[4,3-b]pyridin-5-yl)-3-chloro-N-(1,1-dioxidotetrahydrothiophen-3-yl)benzenesulfonamide

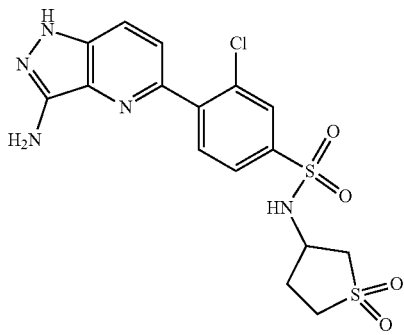 [SMILES: Nc1n[nH]c2ccc(-c3ccc(S(=O)(=O)NC4CCS(=O)(=O)C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(1,1-dioxidotetrahydrothiophen-3-yl)benzenesulfonamide (Intermediate 31b). $^1$H NMR (400 MHz, DMSO-d6) δ ppm 11.85 (br s, 1H) 8.49 (d, 1H) 7.98 (d, 1H) 7.92-7.88 (m, 1H) 7.87-7.82 (m, 2H) 7.58 (d, 1H) 5.45 (br s, 2H) 4.12-4.00 (m, 1H) 3.30-3.20 (m, 2H) 3.16- 3.07 (m, 1H) 2.88 (dd, 1H) 2.31-2.22 (m, 1H) 2.09-1.95 (m, 1H). (UPLC-MS) t$_R$ 0.65 min; ESI-MS 442.2 [M+H]$^+$; ESI-MS 440.1 [M−H]$^−$.

Example 32: N-(4-(3-amino-1H-pyrazolo[4,3-b]pyridin-5-yl)-3-chlorophenyl)-2-hydroxy-5-methylbenzenesulfonamide

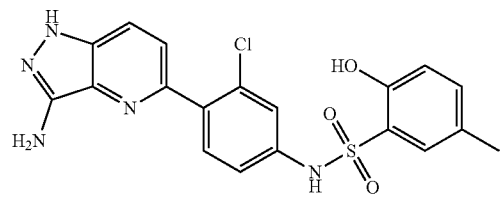 [SMILES: Cc1ccc(O)c(S(=O)(=O)Nc2ccc(-c3ccc4[nH]nc(N)c4n3)c(Cl)c2)c1]

The title compound was prepared in an analogous manner to N-(4-(3-amino-1H-pyrazolo[4,3-b]pyridin-5-yl)-3-chlorophenyl)-2-hydroxycyclohexane-1-sulfonamide (Example 17) using N-(3-chloro-4-(6-cyano-5-fluoropyridin-2-yl)phenyl)-2-hydroxy-5-methylbenzenesulfonamide (Intermediate 32b) at 80° C. for 1 hr. The product was purified twice using reverse phase column chromatography (Method 2, 2-100% ACN in water) to afford the title compound as white solid. $^1$H NMR (400 MHz, DMSO-d6) δ ppm 11.69 (br s, 1H) 7.72 (d, 1H) 7.55 (s, 1H) 7.43-7.37 (m, 2H) 7.28-7.20 (m, 2H) 7.20-7.14 (m, 1H) 6.84 (d, J=8.19 Hz, 1H) 5.35 (br s, 1H) 2.23 (s, 3H). (UPLC-MS) t$_R$ 0.79 min; ESI-MS 430.2 [M+H]$^+$; ESI-MS 428.3 [M−H]$^−$.

Example 33: N-(4-(3-amino-1H-pyrazolo[4,3-b]pyridin-5-yl)-3-methylphenyl)-3-fluorobenzenesulfonamide

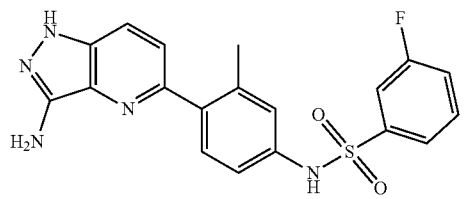 [SMILES: Cc1cc(NS(=O)(=O)c2cccc(F)c2)ccc1-c1ccc2[nH]nc(N)c2n1]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(4-(6-cyano-5-fluoropyridin-2-yl)-3-methylphenyl)-3-fluorobenzenesulfonamide (Intermediate 33b) at 80° C. for 20 hr. The crude material was purified by reverse phase column chromatography (Method 2, 10 to 30% ACN in water). The product was further purified by silica gel column chromatography (0 to 3% MeOH in DCM) to afford the title product as pale yellow solid. $^1$H NMR (400 MHz, DMSO-d$_6$) δ ppm 11.63 (s, 1H) 10.45 (s, 1H) 7.71 (d, 1H) 7.67-7.63 (m, 2H) 7.63-7.58 (m, 1H) 7.56-7.48 (m, 1H) 7.32-7.25 (m, 2H) 7.06-7.00 (m, 2H) 5.32 (br s, 2H) 2.24 (s, 3H). (UPLC-MS) t$_R$ 0.82 min; ESI-MS 398.2 [M+H]$^+$; ESI-MS 396.1 [M−H]$^−$.

Example 34: 1-((4-(3-amino-1H-pyrazolo[4,3-b]pyridin-5-yl)-3-methylphenyl)sulfonyl)-4,4-difluoropyrrolidine-2-carboxamide

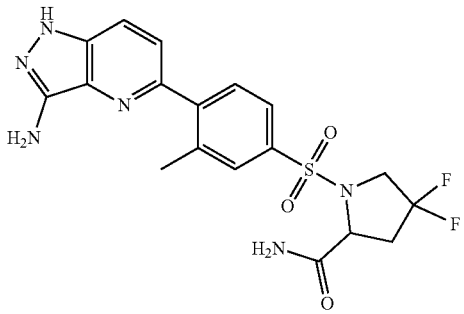 [SMILES: Cc1cc(S(=O)(=O)N2CC(F)(F)CC2C(N)=O)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 1-((4-(6-cyano-5-fluoropyridin-2-yl)-3-methyl phenyl)sulfonyl)-4,4-difluoropyrrolidine-2-carboxamide (Intermediate 34b). $^1$H NMR (400 MHz, DMSO-$d_6$) δ ppm 11.78 (s, 1H), 7.87 (s, 1H), 7.83 (d, 2H), 7.69-7.63 (m, 2H), 7.47 (d, 1H), 7.39 (s, 1H), 5.45 (s, 2H), 4.32 (dd, 1H), 3.95-3.83 (m, 2H), 2.48 (s, 3H). (UPLC-MS) $t_R$ 0.65 min; ESI-MS 437.2 [M+H]$^+$; ESI-MS 435.2 [M−H]$^−$.

Example 35: 4-(3-amino-1H-pyrazolo[4,3-b]pyridin-5-yl)-3-chloro-N-((1S,2R)-2-hydroxycyclopentyl)benzenesulfonamide

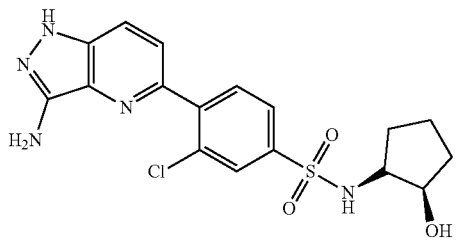

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-((1S,2R)-2-hydroxycyclopentyl)benzene sulfonamide (Intermediate 35b). $^1$H NMR (400 MHz, DMSO-d6) δ ppm 11.83 (s, 1H) 8.02 (d, 1H) 7.90 (dd, 1H) 7.81 (dd, 2H) 7.61-7.54 (m, 2H) 5.45 (s, 2H) 4.71 (d, 1H) 3.83-3.78 (m, 1H) 3.41-3.33 (m, 1H) 1.71-1.56 (m, 2H) 1.52-1.32 (m, 4H). (UPLC-MS) $t_R$ 0.72 min; ESI-MS 408.2 [M+H]$^+$; ESI-MS 406.2 [M−H]$^−$.

Example 36: 4-(3-amino-1H-pyrazolo[4,3-b]pyridin-5-yl)-3-chloro-N-(4-methylcyclohexyl)benzenesulfonamide

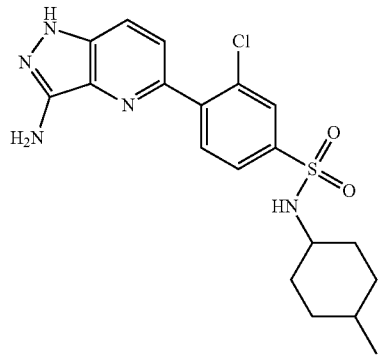 [SMILES: CC1CCC(NS(=O)(=O)c2ccc(-c3ccc4[nH]nc(N)c4n3)c(Cl)c2)CC1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(4-methylcyclohexyl) benzenesulfonamide (Intermediate 36b). $^1$H NMR (400 MHz, DMSO-d6) δ ppm 11.82 (s, 1H), 7.94 (dd, 1H), 7.89-7.75 (m, 4H), 7.55 (d, 1H), 5.43 (s, 2H), 3.26-2.89 (m, 1H), 1.68-0.87 (m, 9H), 0.86-0.76 (m, 3H). (UPLC-MS) $t_R$ 0.99 min; ESI-MS 420.2 [M+H]$^+$; ESI-MS 418.2 [M−H]$^−$.

Example 37: (S)-(1-((4-(3-amino-1H-pyrazolo[4,3-b]pyridin-5-yl)-3-methylphenyl)sulfonyl)-4,4-difluoropyrrolidin-2-yl)methanol

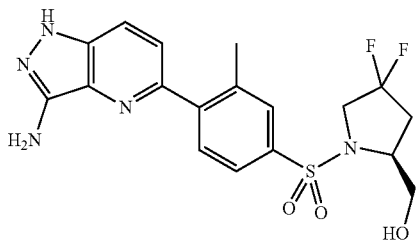 [SMILES: Cc1cc(S(=O)(=O)N2CC(F)(F)C[C@H]2CO)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using (S)-6-(4-((4,4-difluoro-2-(hydroxymethyl)pyrrolidin-1-yl)sulfonyl)-2-methylphenyl)-3-fluoropicolinonitrile (Intermediate 37b). The reaction mixture was concentrated under reduced pressure without extractive workup. The crude product was purified by normal phase chromatography (0 to 25% MeOH in DCM) to give the title compound as a yellow solid. $^1$H NMR (400 MHz, acetonitrile-d3) δ ppm 10.07 (s, 1H), 7.86-7.81 (m, 2H), 7.79 (dd, 1H), 7.67 (d, 1H), 7.46 (d, 1H), 4.70 (s, 2H), 3.95 (ddt, 1H), 3.90-3.82 (m, 1H), 3.82-3.74 (m, 2H), 3.74-3.67 (m, 1H), 3.21 (t, 1H), 2.50 (s, 3H), 2.48-2.39 (m, 1H), 2.39-2.27 (m, 1H). (UPLC-MS) $t_R$ 1.19 min; API-MS 424.2 [M+H]$^+$.

Example 38: 4-(3-amino-1H-pyrazolo[4,3-b]pyridin-5-yl)-3-chloro-N-phenylbenzenesulfonamide

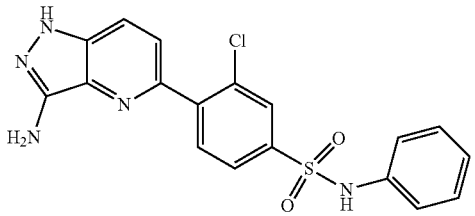 [SMILES: Nc1n[nH]c2ccc(-c3ccc(S(=O)(=O)Nc4ccccc4)cc3Cl)nc12]

In a vial, a solution of 5-chloro-1H-pyrazolo[4,3-b]pyridin-3-amine (Intermediate 38b, 100 mg, 0.48 mmol) in anhydrous dioxane (2.5 mL) was treated with hexamethylditin (171 mg, 0.52 mmol) and Pd(PPh$_3$)$_4$ (27.4 mg, 0.024 mmol) in an argon atmosphere and stirred at 110° C. for 24 h. 4-Bromo-3-chloro-N-phenylbenzenesulfonamide (Intermediate 38c) was added, and the reaction mixture was irradiated in a microwave reactor at 140° C. for 2 h. The reaction mixture was then partitioned between water and EtOAc. The aq. layer was extracted three times with EtOAc, and the combined organic layers were dried over MgSO$_4$, filtered, and concentrated under reduced pressure. The product was purified by silica gel chromatography (0 to 4% MeOH in DCM) to give the title compound as a yellow solid. $^1$H NMR (400 MHz, DMSO-d6) δ ppm 11.82 (s, 1H) 10.46 (s, 1H) 7.88 (d, 1H) 7.82-7.75 (m, 3H) 7.52 (d, 1H) 7.32-7.26 (m, 2H) 7.16 (d, 2H) 7.11-7.06 (m, 1H) 5.44 (br s, 2H). (UPLC-MS) t$_R$ 0.84 min; ESI-MS 400.1 [M+H]$^+$; ESI-MS 398.2 [M−H]$^−$.

Example 39: 4-(3-amino-1H-pyrazolo[4,3-b]pyridin-5-yl)-N-cyclohexyl-3-methylbenzenesulfonamide

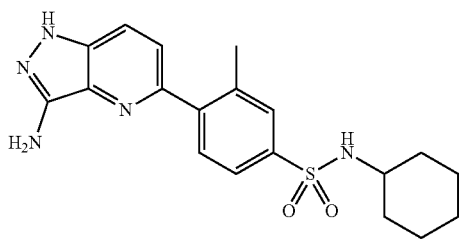 [SMILES: Cc1cc(S(=O)(=O)NC2CCCCC2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 4-(6-cyano-5-fluoropyridin-2-yl)-N-cyclohexyl-3-methylbenzenesulfonamide (Intermediate 39b). $^1$H NMR (400 MHz, DMSO-d$_6$) δ ppm 11.75 (br s, 1H) 7.80 (d, 1H) 7.75 (d, 1H) 7.71 (dd, 1H) 7.65 (d, 1H) 7.60 (d, 1H) 7.45 (d, 1H) 5.41 (br s, 2H) 2.98 (m, 1H) 2.42 (s, 3H) 1.68-1.54 (m, 4H) 1.50-1.40 (m, 1H) 1.27-0.99 (m, 5H). (UPLC-MS) t$_R$ 0.90 min; ESI-MS 386.2 [M+H]$^+$; ESI-MS 384.2 [M−H]$^−$.

Example 40: 4-(3-amino-1H-pyrazolo[4,3-b]pyridin-5-yl)-N-cyclohexyl-3-methylbenzenesulfonamide

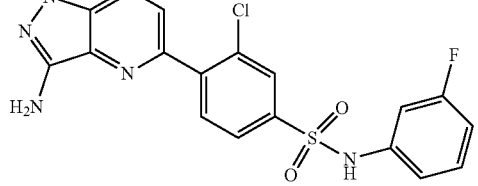

The title compound was prepared in an analogous manner to 4-(3-amino-1H-pyrazolo[4,3-b]pyridin-5-yl)-3-methyl-N-phenylbenzenesulfonamide (Example 16) using 3-chloro-4-(6-cyano-5-fluoropyridin-2-yl)-N-(3-fluorophenyl)benzenesulfonamide (Intermediate 40b). $^1$H NMR (400 MHz, DMSO-d6) δ ppm 11.83 (br s, 1H) 10.78 (s, 1H) 7.93 (d, 1H) 7.86-7.77 (m, 3H) 7.53 (d, 1H) 7.38-7.29 (m, 1H) 7.02-6.88 (m, 3H) 5.46 (br s, 2H). (UPLC-MS) t$_R$ 0.91 min; ESI-MS 418.1 [M+H]$^+$; ESI-MS 416.1 [M−H]$^−$.

Example 41: N-(4-(3-amino-1H-pyrazolo[4,3-b]pyridin-5-yl)-3-chlorophenyl)-3-fluorobenzenesulfonamide

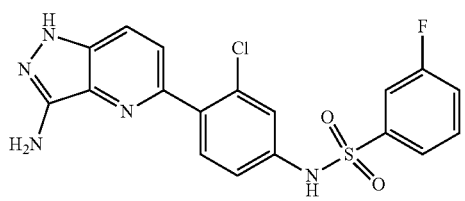 [SMILES: Nc1n[nH]c2ccc(-c3ccc(NS(=O)(=O)c4cccc(F)c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3-fluorobenzenesulfonamide (Intermediate 41 b) at 80° C. for 3.5 h. The crude material was purified by reverse phase column chromatography (Method 2, 5% to 45% ACN in water). The residue was further purified by silica gel column chromatography (0% to 3% MeOH in DCM) to afford the product as yellow solid. $^1$H NMR (400 MHz, DMSO-d6) δ ppm 11.72 (s, 1H) 10.81 (s, 1H) 7.74 (d, 1H) 7.68 (m, 2H) 7.64 (br d, 1H) 7.60-7.52 (m, 1H) 7.50 (d, 1H) 7.41 (d, 1H) 7.25 (d, 1H) 7.21 (dd, 1H) 5.36 (br s, 2H). (UPLC-MS) t$_R$ 0.85 min; ESI-MS 418.1 [M+H]$^+$; ESI-MS 416.1 [M−H]$^−$.

Example 42: N-(4-(3-amino-1H-pyrazolo[4,3-b]pyridin-5-yl)-3-methylphenyl)-3-chlorobenzenesulfonamide

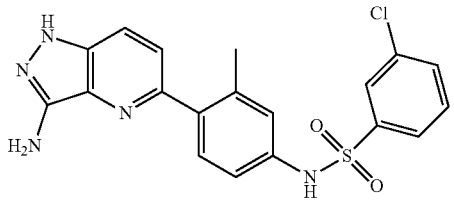 [SMILES: Cc1cc(NS(=O)(=O)c2cccc(Cl)c2)ccc1-c1ccc2[nH]nc(N)c2n1]

The title compound was prepared in an analogous manner to N-(4-(3-amino-1H-pyrazolo[4,3-b]pyridin-5-yl)-3-chlorophenyl)-4-chlorobenzenesulfonamide (Example 3) using 3-chloro-N-(4-(6-cyano-5-fluoropyridin-2-yl)-3-methylphenyl)benzenesulfonamide (Intermediate 42b) at 80° C. for 2.5 h then, RT overnight. The residue was purified by reverse phase column chromatography (Method 2, 10% to 35% ACN in water). The residue was further purified by silica gel column chromatography (0 to 3% MeOH in DCM) to afford the title compound as pale yellow solid. $^1$H NMR (400 MHz, DMSO-d6) δ ppm 11.63 (s, 1H) 10.46 (br s, 1H) 7.82 (d, 1H) 7.78-7.69 (m, 3H) 7.65-7.59 (dt, 1H) 7.29 (dt, 2H) 7.02 (m, 2H) 5.32 (br s, 2H) 2.24 (s, 3H). (UPLC-MS) $t_R$ 0.88 min; ESI-MS 414.1 [M+H]$^+$; ESI-MS 412.1 [M−H]$^-$.

Example 43: N-(4-(3-amino-1H-pyrazolo[4,3-b]pyridin-5-yl)-3-chlorophenyl)-3,4-dichlorobenzenesulfonamide

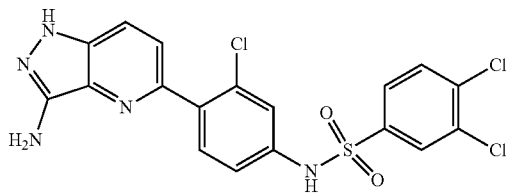 [SMILES: Nc1n[nH]c2ccc(-c3ccc(NS(=O)(=O)c4ccc(Cl)c(Cl)c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using 3,4-dichloro-N-(3-chloro-4-(6-cyano-5-fluoropyridin-2-yl)phenyl)benzenesulfonamide (Intermediate 43b) at 80° C. for 2 h. The residue was purified by preparative HPLC (Method 3, 20% to 70% ACN (+7.3 mM NH$_4$OH) in water (+7.3 mM NH$_4$OH)). The residue was further purified by silica gel column chromatography (0% to 3% MeOH in DCM) to afford the title compound as pale yellow solid. $^1$H NMR (400 MHz, DMSO-d6) δ ppm 11.73 (s, 1H) 10.86 (br s, 1H) 8.04 (d, 1H) 7.91 (d, 1H) 7.79-7.76 (dd, 1H) 7.75 (d, 1H) 7.51 (d, 1H) 7.42 (d, 1H) 7.26 (d, 1H) 7.21 (dd, 1H) 5.36 (s, 2H). (UPLC-MS) $t_R$ 1.00 min; ESI-MS 468.1/470.1/472.1 [M+H]$^+$; ESI-MS 466.0/468.0/470.0 [M−H]$^-$.

Example 44: 4-(3-amino-1H-pyrazolo[4,3-b]pyridin-5-yl)-3-chloro-N-(3-hydroxycyclohexyl)benzenesulfonamide

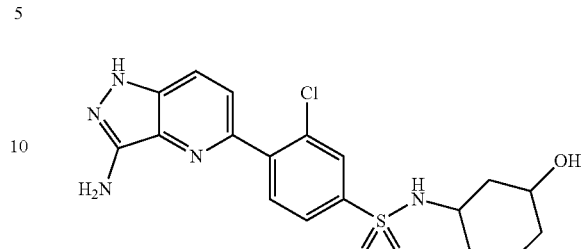

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 3-chloro-4-(6-cyano-5-fluoropyridin-2-yl)-N-(3-hydroxycyclohexyl)benzenesulfonamide (Intermediate 44b). The crude product was purified by preparative HPLC (Method 1, 5% to 95% ACN in water (+0.1% TFA)). Fractions containing purified product were combined and passed through a PL-HCO3 MP cartridge (Stratospheres, pre-conditioned with MeOH). After washout with MeOH, the filtrate was concentrated under reduced pressure. This product was further purified by silica gel column chromatography (0 to 10% MeOH in DCM) to afford the title compound as a yellow solid diastereoisomeric mixture. $^1$H NMR (400 MHz, DMSO-d6) δ ppm 11.83 (s, 1H) 7.96-7.91 (m, 1H) 7.89-7.79 (m, 3H) 7.98-7.78 (m, 1H) 7.56 (d, 1H) 5.46 (br s, 2H) 4.65-4.41 (m, 1H) 3.87-3.36 (m, 1H) 3.31-2.98 (m, 1H) 1.86-1.65 (m, 1H) 1.63-1.30 (m, 4H) 1.27-0.82 (m, 3H) (UPLC-MS) $t_R$ 0.68 min; ESI-MS 422.2 [M+H]$^+$; ESI-MS 420.2 [M−H]$^-$.

Example 45: 4-(3-amino-1H-pyrazolo[4,3-b]pyridin-5-yl)-3-chloro-N-((1r,4r)-4-hydroxycyclohexyl)benzenesulfonamide

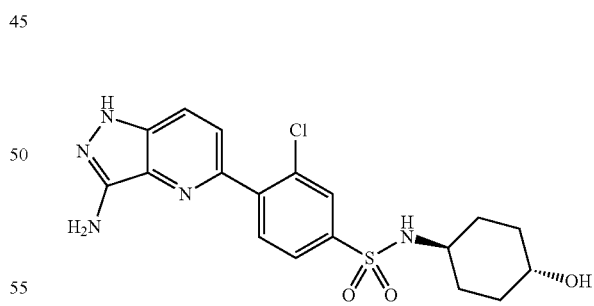

The title compound was prepared in an analogous manner to 4-(3-amino-1H-pyrazolo[4,3-b]pyridin-5-yl)-3-chloro-N-(3-hydroxycyclohexyl)benzenesulfonamide (Example 44) using 3-chloro-4-(6-cyano-5-fluoropyridin-2-yl)-N-((1r,4r)-4-hydroxycyclohexyl)benzenesulfonamide (Intermediate 45b). $^1$H NMR (400 MHz, DMSO-d$_6$) δ ppm 11.84 (s, 1H) 7.94 (s, 1H) 7.89-7.79 (m, 4H) 7.57 (d, 1H) 5.45 (s, 2H) 4.50 (d, 1H) 3.05-2.94 (m, 1H) 1.77-1.69 (m, 2H) 1.68-1.60 (m, 2H) 1.28-1.04 (m, 5H). (UPLC-MS) $t_R$ 0.65 min; ESI-MS 422.2 [M+H]$^+$; ESI-MS 420.2 [M−H]$^-$.

Example 46: N-(4-(3-amino-1H-pyrazolo[4,3-b]pyridin-5-yl)-3-chlorophenyl)benzenesulfonamide

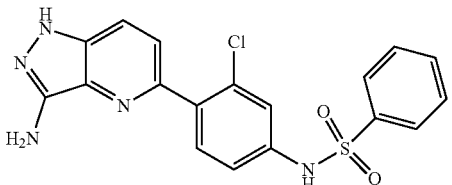

In a MW vial, a solution of 5-chloro-1H-pyrazolo[4,3-b]pyridin-3-amine (Intermediate 38b) (30 mg, 0.142 mmol) in ACN (0.75 mL) was treated with N-(3-chloro-4-(4,4,5,5-tetramethyl-1,3,2-dioxaborolan-2-yl)phenyl)benzenesulfonamide (Intermediate 46b, 119 mg, 0.184 mmol), Pd(PPh$_3$)$_2$Cl$_2$ (9.99 mg, 0.014 mmol) and a 2M aq. Na$_2$CO$_3$ solution (214 μL, 0.427 mmol) in an argon atmosphere and irradiated in a microwave reactor at 120° C. for 2 h. After removing the volatiles under reduced pressure, the crude product was purified by reverse phase column chromatography (Method 2, 2% to 100% ACN in water). Fractions containing the product were combined, concentrated under reduced pressure and the so obtained product was further purified by silica gel column chromatography (0 to 6% MeOH in DCM) to afford the title compound as a beige solid. $^1$H NMR (400 MHz, DMSO-d$_6$) δ ppm 11.72 (br s, 1H) 10.73 (s, 1H) 7.88-7.82 (m, 2H) 7.73 (d, 1H) 7.69-7.58 (m, 3H) 7.47 (d, 1H) 7.40 (d, 1H) 7.24 (d, 1H) 7.19 (dd, 1H) 5.36 (br s, 2H). (UPLC-MS) t$_R$ 0.81 min; ESI-MS 400.1 [M+H]$^+$; ESI-MS 398.1 [M−H]$^−$.

Example 47: 4-(3-amino-1H-pyrazolo[4,3-b]pyridin-5-yl)-N-((1s,3s)-3-(hydroxymethyl)cyclobutyl)-3-methyl benzenesulfonamide

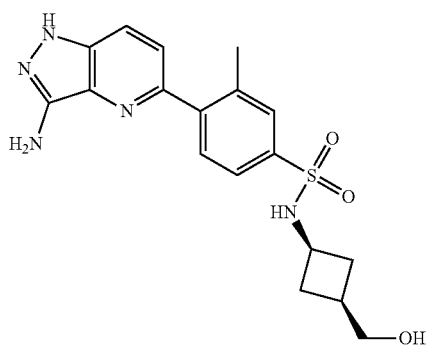 [SMILES: Cc1cc(S(=O)(=O)N[C@H]2C[C@@H](CO)C2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(4-methylcyclohexyl)benzenesulfonamide (Intermediate 36b). $^1$H NMR (400 MHz, DMSO-d$_6$) δ ppm 11.75 (s, 1H) 7.85 (d, 1H) 7.80 (d, 1H) 7.71 (d, 1H) 7.69 (dd, 1H) 7.62-7.58 (m, 1H) 7.44 (d, 1H) 5.41 (s, 2H) 4.42 (t, 1H) 3.61-3.49 (m, 1H) 3.23 (t, 2H) 2.43 (s, 3H) 2.04-1.95 (m, 2H) 1.95-1.85 (m, 1H) 1.55-1.45 (m, 2H). (UPLC-MS) t$_R$ 0.59 min; ESI-MS 388.3 [M+H]$^+$; ESI-MS 386.3 [M−H]$^−$.

Example 48: 4-(3-amino-1H-pyrazolo[4,3-b]pyridin-5-yl)-3-chloro-N-((1s,4s)-4-hydroxycyclohexyl)benzenesulfonamide

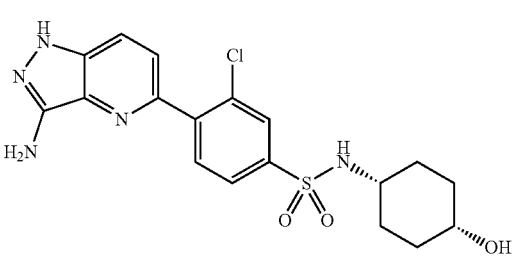 [SMILES: Nc1n[nH]c2ccc(-c3ccc(S(=O)(=O)N[C@H]4CC[C@@H](O)CC4)cc3Cl)nc12]

The title compound was prepared in an analogous manner to 4-(3-amino-1H-pyrazolo[4,3-b]pyridin-5-yl)-3-chloro-N-(3-hydroxycyclohexyl)benzenesulfonamide (Example 44) using 3-chloro-4-(6-cyano-5-fluoropyridin-2-yl)-N-((1s,4s)-4-hydroxycyclohexyl)benzenesulfonamide (Intermediate 48b). $^1$H NMR (400 MHz, DMSO-d$_6$) δ ppm 11.83 (s, 1H) 7.96 (d, 1H) 7.90-7.86 (m, 1H) 7.86-7.80 (m, 3H) 7.56 (d, 1H) 5.46 (s, 2H) 4.36 (d, 1H) 3.63-3.56 (m, 1H) 3.13-3.02 (m, 1H) 1.63-1.48 (m, 4H) 1.45-1.32 (m, 4H). (UPLC-MS) t$_R$ 0.69 min; ESI-MS 422.2 [M+H]$^+$; ESI-MS 420.2 [M−H]$^−$.

Example 49: 4-(3-amino-1H-pyrazolo[4,3-b]pyridin-5-yl)-3-fluoro-N-phenylbenzenesulfonamide

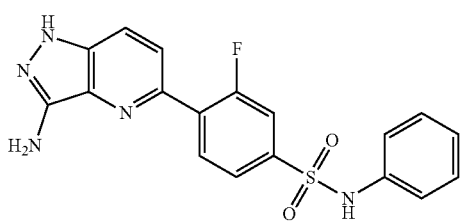 [SMILES: Nc1n[nH]c2ccc(-c3ccc(S(=O)(=O)Nc4ccccc4)cc3F)nc12]

The title compound was prepared in an analogous manner to N-(4-(3-amino-1H-pyrazolo[4,3-b]pyridin-5-yl)-3-chlorophenyl)benzenesulfonamide (Example 46) using 3-fluoro-N-phenyl-4-(4,4,5,5-tetramethyl-1,3,2-dioxaborolan-2-yl)benzenesulfonamide (Intermediate 49b). After removing the volatiles under reduced pressure, the crude product was purified twice by silica gel column chromatography (first 0 to 20% MeOH in DCM, then 0 to 100% EtOAc in cyclohexane). The so obtained product was further purified by reverse phase column chromatography (Method 2, 2% to 100% ACN in water) to afford the title compound as an off-white solid. $^1$H NMR (400 MHz, DMSO-d$_6$) δ ppm 11.84 (s, 1H) 10.42 (s, 1H) 8.13 (t, 1H) 7.81 (d, 1H) 7.71-7.62 (m, 3H) 7.31-7.23 (m, 2H) 7.14 (d, 2H) 7.07 (t, 1H) 5.48 (s, 2H). (UPLC-MS) t$_R$ 0.81 min; ESI-MS 384.1 [M+H]$^+$; ESI-MS 382.1 [M−H]$^−$.

Example 50: 4-(3-amino-1H-pyrazolo[4,3-b]pyridin-5-yl)-3-chloro-N-(1,1-dioxidotetrahydro-2H-thiopyran-4-yl)benzenesulfonamide

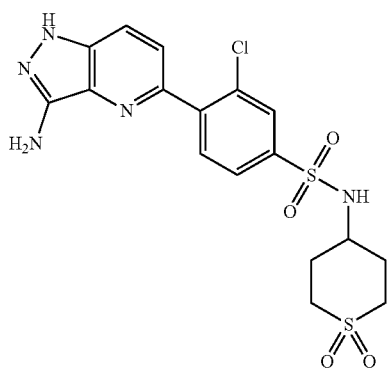 [SMILES: Nc1n[nH]c2ccc(-c3ccc(S(=O)(=O)NC4CCS(=O)(=O)CC4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(1,1-dioxidotetrahydro-2H-thiopyran-4-yl)benzenesulfonamide (Intermediate 50b). $^1$H NMR (400 MHz, DMSO-d6) δ ppm 11.85 (s, 1H) 8.20 (br s, 1H) 7.96 (s, 1H) 7.80-7.92 (m, 3H) 7.57 (d, 1H) 5.44 (s, 2H) 3.55 (br s, 1H) 3.15-3.25 (m, 2H) 3.05 (br d, 2H) 2.03-1.82 (m, 4H). (UPLC-MS) $t_R$ 0.64 min; ESI-MS 456.2 [M+H]$^+$; ESI-MS 454.2 [M−H]$^−$.

Example 51: 5-(2-chloro-4-((hexahydrocyclopenta[c]pyrrol-2(1H)-yl)sulfonyl)phenyl)-1H-pyrazolo[4,3-b]pyridin-3-amine

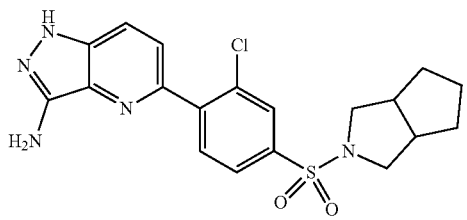 [SMILES: Nc1n[nH]c2ccc(-c3ccc(S(=O)(=O)N4CC5CCCC5C4)cc3Cl)nc12]

The title compound was prepared in an analogous manner to 4-(3-amino-1H-pyrazolo[4,3-b]pyridin-5-yl)-3-chloro-N-(1-(hydroxymethyl)cyclopentyl)benzenesulfonamide (Example 30) using 6-(2-chloro-4-((hexahydrocyclopenta[c]pyrrol-2(1H)-yl)sulfonyl)phenyl)-3-fluoropicolinonitrile (Intermediate 51b). $^1$H NMR (400 MHz, DMSO-d6) δ ppm 11.86 (s, 1H) 7.90-7.81 (m, 4H) 7.58 (d, 1H) 5.45 (br s, 2H) 3.18 (br dd, 2H) 2.89 (dd, 2H) 2.61-2.53 (m, 2H) 1.76-1.65 (m, 2H) 1.59-1.38 (m, 2H) 1.37-1.28 (m, 2H). (UPLC-MS) $t_R$ 1.00 min; ESI-MS 418.2 [M+H]$^+$; ESI-MS 416.1 [M−H]$^−$.

Example 52: 4-(3-amino-1H-pyrazolo[4,3-b]pyridin-5-yl)-3-chloro-N-(3-chloro-2-fluorophenyl)benzenesulfonamide

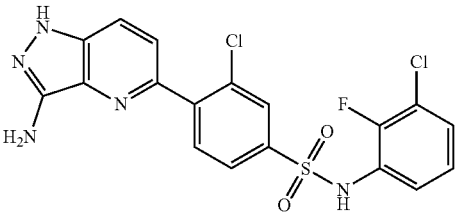

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-N-(3-chloro-2-fluorophenyl)-4-(6-cyano-5-fluoropyridin-2-yl)benzenesulfonamide (Intermediate 52b). The reaction mixture was concentrated under reduced pressure to afford a yellow oil that underwent purification by reverse phase column chromatography (Method 2, 5% to 50% ACN in water) to afford the title compound as a yellow solid. $^1$H NMR (400 MHz, DMSO-d6) δ ppm 11.85 (br s, 1H) 10.70 (br s, 1H) 7.89 (d, 1H) 7.85-7.77 (m, 3H) 7.55 (d, 1H) 7.47-7.41 (m, 1H) 7.33-7.26 (m, 1H) 7.25-7.18 (m, 1H) 5.47 (br s, 2H). (UPLC-MS) $t_R$ 0.92 min; ESI-MS 452.2/454.1 [M+H]$^+$; ESI-MS 450.2/452.2 [M−H]$^−$.

Example 53: N-(4-(3-amino-1H-pyrazolo[4,3-b]pyridin-5-yl)-3-chlorophenyl)-3,4-dihydro-2H-benzo[b][1,4]oxazine-6-sulfonamide

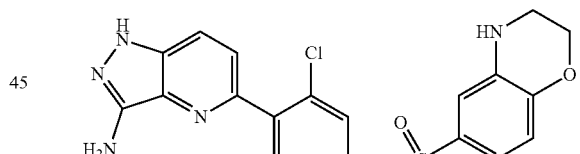

A solution of 4-acetyl-N-(3-chloro-4-(6-cyano-5-fluoropyridin-2-yl)phenyl)-3,4-dihydro-2H-benzo[b][1,4]oxazine-6-sulfonamide (Intermediate 53b) (82 mg, 0.168 mmol) in hydrazine hydrate 78% in water (600 μL, 9.63 mmol) was heated up and stirred at 100° C. for 1 h. The reaction was diluted with EtOAc and washed three times with water and brine, dried over anhydrous MgSO$_4$, filtered and concentrated under reduced pressure. The residue was purified by reverse phase column chromatography (Method 2, 2% to 100% ACN in water) to afford the title compound as white solid. $^1$H NMR (400 MHz, DMSO-d6) δ ppm 11.69 (s, 1H), 10.47 (s, 1H), 7.72 (d, 1H), 7.42 (dd, 2H), 7.22 (d, 1H), 7.15 (dd, 1H), 7.03 (d, 1H), 6.93 (dd, 1H), 6.76 (d, 1H), 6.34 (s, 1H), 5.34 (s, 2H), 4.20-4.09 (m, 2H), 3.27 (s, 2H). (UPLC-MS) $t_R$ 0.78 min; ESI-MS 457.2 [M+H]$^+$; ESI-MS 455.1 [M−H]$^−$.

Example 54: 4-(3-amino-1H-pyrazolo[4,3-b]pyridin-5-yl)-N-((1r,4r)-4-hydroxycyclohexyl)-3-methylbenzenesulfonamide

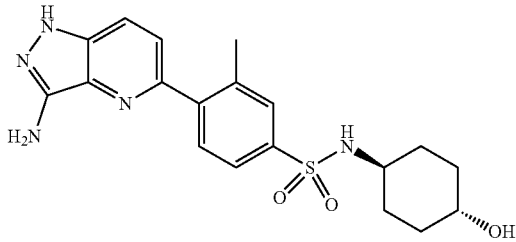 [SMILES: Cc1cc(S(=O)(=O)N[C@H]2CC[C@H](O)CC2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 4-(6-cyano-5-fluoropyridin-2-yl)-N-((1r,4r)-4-hydroxycyclohexyl)-3-methylbenzenesulfonamide (Intermediate 54b). $^1$H NMR (400 MHz, DMSO-d6) δ ppm 11.75 (br s, 1H) 7.80 (d, 1H) 7.76-7.73 (m, 1H) 7.73-7.69 (m, 1H) 7.65-7.58 (m, 2H) 7.45 (d, 1H) 5.42 (br s, 2H) 4.48 (br s, 1H) 3.37-3.24 (m, 1H) 3.00-2.88 (m, 1H) 2.42 (s, 3H) 1.76-1.69 (m, 2H) 1.68-1.60 (m, 2H) 1.25-1.02 (m, 4H). (UPLC-MS) $t_R$ 0.60 min; ESI-MS 402.3 [M+H]$^+$; ESI-MS 400.3 [M−H]$^−$.

Example 55: (2R,4R)-1-((4-(3-amino-1H-pyrazolo[4,3-b]pyridin-5-yl)-3-chlorophenyl)sulfonyl)-4-fluoropyrrolidine-2-carboxamide

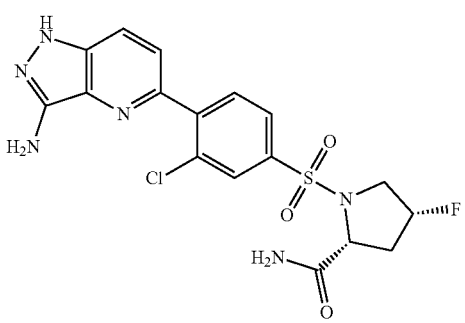 [SMILES: NC(=O)[C@H]1C[C@@H](F)CN1S(=O)(=O)c1ccc(-c2ccc3[nH]nc(N)c3n2)c(Cl)c1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using (2R,4R)-1-((3-chloro-4-(6-cyano-5-fluoropyridin-2-yl)phenyl)sulfonyl)-4-fluoropyrrolidine-2-carboxamide (Intermediate 55b). $^1$H NMR (400 MHz, DMSO-d6) δ ppm 11.85 (s, 1H) 8.05 (d, 1H) 7.96 (dd, 1H) 7.88-7.81 (m, 2H) 7.58 (d, 1H) 7.30 (br d, 2H) 5.45 (s, 2 H) 5.32-5.12 (m, 1H) 4.32 (d, 1H) 3.77-3.64 (m, 1H) 3.63-3.46 (m, 1H) 2.31-2.18 (m, 1H) 2.11-1.89 (m, 1H). (UPLC-MS) $t_R$ 0.62 min; ESI-MS 439.2 [M+H]$^+$; ESI-MS 437.1 [M−H]$^−$.

Example 56: 4-(3-amino-1H-pyrazolo[4,3-b]pyridin-5-yl)-3-chloro-N-(2,3-dichlorophenyl)benzenesulfonamide

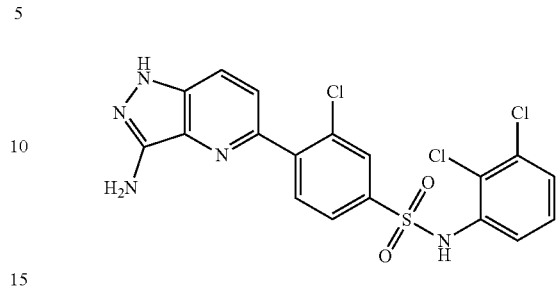

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(2,3-dichlorophenyl)benzenesulfonamide (Intermediate 56b). The reaction mixture was concentrated under reduced pressure to afford a crude material that underwent purification by reverse phase column chromatography (Method 2, 5% to 50% ACN in water). Fractions containing pure title compound were combined and extracted three times with DCM. The combined organic layers were washed with brine, dried over anhydrous MgSO$_4$, and concentrated under reduced pressure to afford the title compound as a yellow solid. $^1$H NMR (400 MHz, DMSO-d6) δ ppm 11.85 (br s, 1H) 10.54 (br s, 1H) 7.89 (d, 1H) 7.85-7.77 (m, 3H) 7.57-7.51 (m, 2H) 7.40-7.33 (m, 1H) 7.32-7.27 (m, 1H) 5.47 (br s, 2H). (UPLC-MS) $t_R$ 0.99 min; ESI-MS 468.0/470.0/472.0 [M+H]$^+$; ESI-MS 466.0/468.0/470.0 [M−H]$^−$.

Example 57: (R)-1-((4-(3-amino-1H-pyrazolo[4,3-b]pyridin-5-yl)-3-chlorophenyl)sulfonyl) pyrrolidin-3-ol

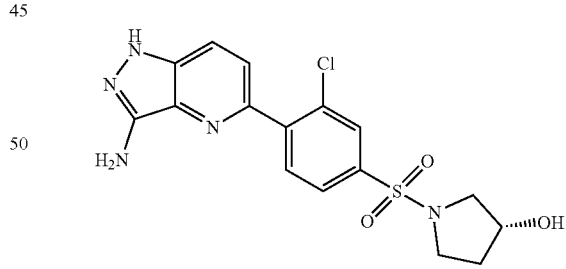

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using (R)-6-(2-chloro-4-(((3-hydroxypyrrolidin-1-yl)sulfonyl)phenyl)-3-fluoropicolinonitrile (Intermediate 57b). $^1$H NMR (400 MHz, DMSO-d6) δ ppm 11.84 (s, 1H) 7.91 (s, 1H) 7.89-7.81 (m, 3H) 7.57 (d, 1H) 5.46 (s, 2H) 4.96 (d, 1H) 4.25-4.18 (m, 1H) 3.40-3.22 (m, 3H) 3.11 (br d, 1H) 1.88-1.77 (m, 1H) 1.75-1.65 (m, 1H). (UPLC-MS) $t_R$ 0.66 min; ESI-MS 394.1 [M+H]$^+$; ESI-MS 392.1 [M−H]$^−$.

Example 58: 4-(3-amino-1H-pyrazolo[4,3-b]pyridin-5-yl)-3-chloro-N-((1r,4r)-4-hydroxy-4-methylcyclohexyl)benzenesulfonamide

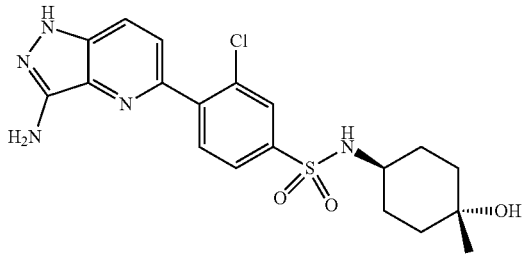

The title compound was prepared in an analogous manner to 4-(3-amino-1H-pyrazolo[4,3-b]pyridin-5-yl)-3-chloro-N-(1-(hydroxymethyl)cyclopentyl)benzenesulfonamide (Example 30) using 3-chloro-4-(6-cyano-5-fluoropyridin-2-yl)-N-((1r,4r)-4-hydroxy-4-methylcyclohexyl)benzenesulfonamide (Intermediate 58b). $^1$H NMR (400 MHz, DMSO-$d_6$) δ ppm 11.83 (s, 1H) 7.95 (d, 1H) 7.89-7.85 (m, 1H) 7.84-7.79 (m, 3H) 7.56 (d, 1H) 5.45 (br s, 2H) 4.15 (s, 1H) 3.14 (br s, 1H) 1.69-1.59 (m, 2H) 1.55-1.46 (m, 2H) 1.35-1.22 (m, 4H) 1.07 (s, 3H). (UPLC-MS) $t_R$ 0.68 min; ESI-MS 436.1 [M+H]$^+$; ESI-MS 434.2 [M−H]$^−$.

Example 59: N-(4-(3-amino-1H-pyrazolo[4,3-b]pyridin-5-yl)-3-chlorophenyl)-1-phenylmethanesulfonamide

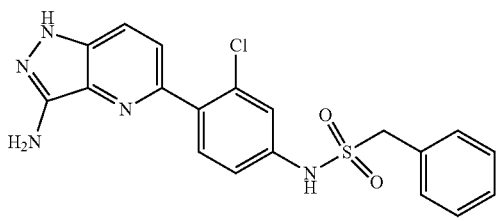 [SMILES: Nc1n[nH]c2ccc(-c3ccc(NS(=O)(=O)Cc4ccccc4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-1-phenylmethanesulfonamide (Intermediate 59b) at 80° C. for 2.5 h. The residue was first purified by purification by reverse phase column chromatography (Method 2, 10% to 30% ACN in water). Fractions containing the product were combined and concentrated under reduced pressure and the so obtained product was further purified by silica gel column chromatography (0 to 3% MeOH in DCM) to afford the title compound as a pale yellow solid. $^1$H NMR (400 MHz, DMSO-d6) δ ppm 11.74 (s, 1H) 10.19 (br s, 1H) 7.78 (d, 1H) 7.55 (d, 1H) 7.47 (d, 1H) 7.41-7.35 (m, 3H) 7.33-7.29 (m, 2H) 7.28-7.22 (m, 2H) 5.36 (s, 2H) 4.58 (s, 2H). (UPLC-MS) $t_R$ 0.83 min; ESI-MS 414.2 [M+H]$^+$; ESI-MS 412.1 [M−H]$^−$.

Example 60: (1R,2S)-N-(4-(3-amino-1H-pyrazolo[4,3-b]pyridin-5-yl)-3-chlorophenyl)-2-hydroxycyclohexane-1-sulfonamide

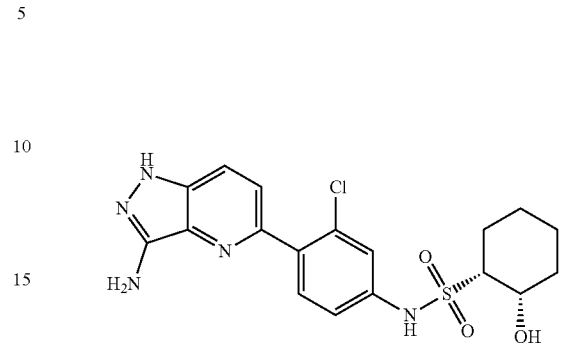

The title compound was obtained by chiral separation of N-(4-(3-amino-1H-pyrazolo[4,3-b]pyridin-5-yl)-3-chlorophenyl)-2-hydroxycyclohexane-1-sulfonamide (Example 17) using the same conditions described for (1S,2R)-N-(4-(3-amino-1H-pyrazolo[4,3-b]pyridin-5-yl)-3-chlorophenyl)-2-hydroxycyclohexane-1-sulfonamide (Example 14) to afford the title compound. $^1$H NMR (400 MHz, DMSO-d6) δ ppm 11.72 (s, 1H) 9.62 (s, 1H) 7.75 (d, 1H) 7.53 (d, 1H) 7.46 (d, 1H) 7.35 (d, 1H) 7.28 (dd, 1H) 5.34 (s, 2H) 5.05 (d, 1H) 3.77 (d, 1H) 3.02-2.92 (m, 1H) 2.05 (d, 1H) 1.88 (d, 1H) 1.65 (d, 2H) 1.54-1.38 (m, 1H) 1.25 (dd, 4H). (UPLC-MS) $t_R$ 0.76 min; ESI-MS 422.1 [M+H]$^+$; ESI-MS 420.1 [M−H]$^−$.

Example 61: N-(5-(N-(4-(3-amino-1H-pyrazolo[4,3-b]pyridin-5-yl)-3-chlorophenyl)sulfamoyl)-2-methoxyphenyl)acetamide

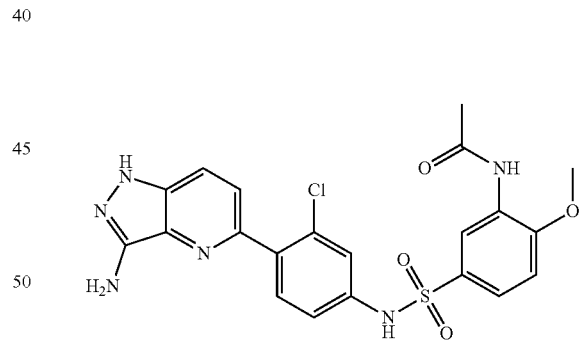

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(5-(N-(3-chloro-4-(6-cyano-5-fluoropyridin-2-yl)phenyl)sulfamoyl)-2-methoxyphenyl)acetamide (Intermediate 61b) at 80° C. for 3.5 h. The residue was purified by reverse phase column chromatography (Method 2, 2% to 100% ACN in water) to afford the title compound. $^1$H NMR (400 MHz, DMSO-d6) δ ppm 11.71 (s, 1H) 10.64 (br s, 1H) 9.37 (s, 1H) 8.63 (s, 1H) 7.73 (d, 1H) 7.55 (dd, 1H) 7.44 (d, 1H) 7.40 (d, 1H) 7.15-7.25 (m, 3H) 5.35 (s, 2H) 3.90 (s, 3H) 2.12 (s, 3H). (UPLC-MS) $t_R$ 0.72 min; ESI-MS 487.3 [M+H]$^+$; ESI-MS 485.3 [M−H]$^−$.

Example 62: N-(4-(3-amino-1H-pyrazolo[4,3-b]pyridin-5-yl)-3-chlorophenyl)-3-(trifluoromethyl)benzenesulfonamide

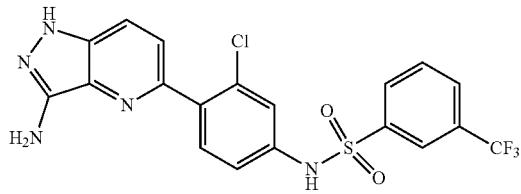 [SMILES: Nc1n[nH]c2ccc(-c3ccc(NS(=O)(=O)c4cccc(C(F)(F)F)c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3-(trifluoromethyl)benzenesulfonamide (Intermediate 62B) at 80° C. for 2 h. The residue was purified by preparative HPLC (Method 1, 5% to 95% ACN in water (+0.1% TFA)). The residue was further purified by silica gel column chromatography (0 to 4% MeOH in DCM) to afford the title compound as yellow solid. $^1$H NMR (400 MHz, DMSO-d6) b ppm 11.73 (s, 1H) 10.86 (s, 1H) 8.06-8.14 (m, 3H) 7.87 (t, 1H) 7.74 (d, 1H) 7.50 (d, 1H) 7.40 (d, 1H) 7.25 (d, 1H) 7.20 (dd, 1H) 5.35 (s, 2H). (UPLC-MS) $t_R$ 0.95 min; ESI-MS 468.1 [M+H]$^+$; ESI-MS 466.1 [M–H]$^-$.

Example 63: 5-(4-(3-azabicyclo[3.1.0]hexan-3-ylsulfonyl)-2-chlorophenyl)-1H-pyrazolo[4,3-b]pyridin-3-amine

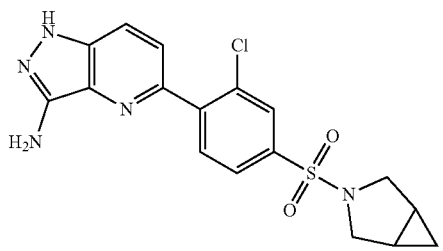 [SMILES: Nc1n[nH]c2ccc(-c3ccc(S(=O)(=O)N4CC5CC5C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 6-(4-(3-azabicyclo[3.1.0]hexan-3-ylsulfonyl)-2-chlorophenyl)-3-fluoropicolinonitrile (Intermediate 63b). $^1$H NMR (400 MHz, DMSO-d$_6$) δ ppm 11.85 (s, 1H) 7.91-7.81 (m, 4H) 7.59 (d, 1H) 5.45 (br s, 2H) 3.45 (d, 2H) 3.17-3.11 (m, 2H) 1.57-1.51 (m, 2H) 0.64-0.56 (m, 1H) 0.11-0.06 (m, 1H). (UPLC-MS) $t_R$ 0.87 min; ESI-MS 390.0 [M+H]$^+$; ESI-MS 388.1 [M–H]$^-$.

Example 64: 4-(3-amino-1H-pyrazolo[4,3-b]pyridin-5-yl)-N-((1s,3s)-3-hydroxycyclobutyl)-3-methylbenzenesulfonamide

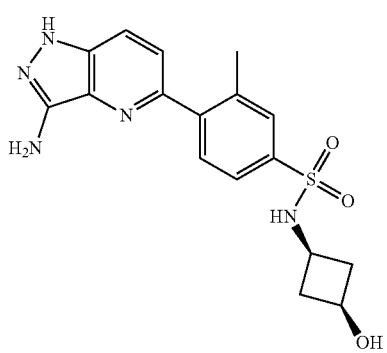 [SMILES: Cc1cc(S(=O)(=O)N[C@H]2C[C@@H](O)C2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 4-(6-cyano-5-fluoropyridin-2-yl)-N-((1s,3s)-3-hydroxycyclobutyl)-3-methylbenzenesulfonamide (Intermediate 64b). $^1$H NMR (400 MHz, DMSO-d6) δ ppm 11.75 (br s, 1H) 7.87 (d, 1H) 7.80 (d, 1H) 7.71 (s, 1H) 7.68 (d, 1H) 7.62-7.58 (m, 1H) 7.44 (d, 1H) 5.42 (br s, 2H) 5.01 (d, 1H) 3.71-3.60 (m, 1H) 3.19-3.11 (m, 1H) 2.43 (s, 3H) 2.31-2.23 (m, 2H) 1.65-1.55 (m, 2H). (UPLC-MS) $t_R$ 0.60 min; ESI-MS 374.1 [M+H]$^+$; ESI-MS 372.1 [M–H]$^-$.

Example 65: 4-(3-amino-1H-pyrazolo[4,3-b]pyridin-5-yl)-N-(3-hydroxycyclohexyl)-3-methylbenzenesulfonamide

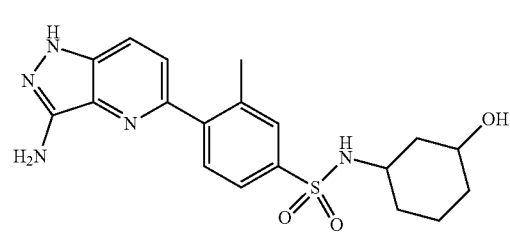 [SMILES: Cc1cc(S(=O)(=O)NC2CCCC(O)C2)ccc1-c1ccc2[nH]nc(N)c2n1]

The title compound was prepared in an analogous manner to 5-(4-((hexahydrocyclopenta[c]pyrrol-2(1H)-yl)sulfonyl)-2-methylphenyl)-1H-pyrazolo[4,3-b]pyridin-3-amine (Example 21) using 4-(6-cyano-5-fluoropyridin-2-yl)-N-(3-hydroxycyclohexyl)-3-methylbenzenesulfonamide (Intermediate 65b) to give a mixture of diastereomers that was not characterized by $^1$H NMR. (UPLC-MS) $t_R$ 0.64 min; ESI-MS 402.3 [M+H]$^+$; ESI-MS 400.2 [M–H]$^-$.

Example 66: 1-((4-(3-amino-1H-pyrazolo[4,3-b]pyridin-5-yl)-3-methylphenyl)sulfonyl)-3-(trifluoromethyl)azetidin-3-ol

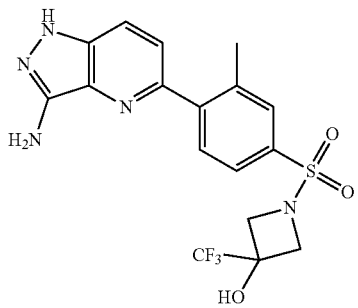 [SMILES: Cc1cc(S(=O)(=O)N2CC(O)(C(F)(F)F)C2)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-fluoro-6-(4-((3-hydroxy-3-(trifluoromethyl)azetidin-1-yl)sulfonyl)-2-methylphenyl)picolinonitrile (Intermediate 66b). $^1$H NMR (400 MHz, DMSO-d6) δ 11.77 (s, 1H), 7.82 (s, 2H), 7.77-7.68 (m, 2H), 7.46 (s, 2H), 5.42 (s, 2H), 4.05 (d, 2H), 3.75 (d, 2H), 2.51-2.45 (m, 3H). (UPLC-MS) $t_R$ 0.78 min; ESI-MS 428.1 [M+H]$^+$; ESI-MS 426.1 [M−H]$^−$.

Example 67: N-(4-(3-amino-1H-pyrazolo[4,3-b]pyridin-5-yl)-3-chlorophenyl)-3-methoxybenzenesulfonamide

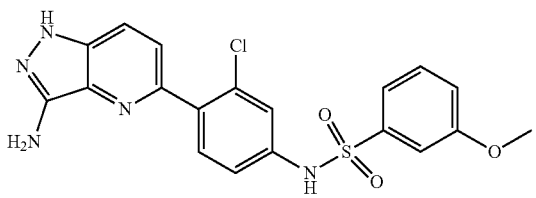 [SMILES: COc1cccc(S(=O)(=O)Nc2ccc(-c3ccc4[nH]nc(N)c4n3)c(Cl)c2)c1]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3-methoxybenzenesulfonamide (Intermediate 67b) at 80° C. for 2.5 h. The residue was purified by reverse phase column chromatography (Method 2, 10% to 30% ACN in water). The residue was further purified by silica gel column chromatography (0 to 3% of MeOH in DCM) to afford the title compound as pale yellow solid. $^1$H NMR (400 MHz, DMSO-d$_6$) δ ppm 11.72 (s, 1H) 10.68 (br s, 1H) 7.74 (d, 1H) 7.55-7.50 (m, 1H) 7.48 (d, 1H) 7.43-7.38 (m, 2H) 7.33 (t, 1H) 7.25 (d, 1H) 7.24-7.17 (m, 2H) 5.35 (s, 2H) 3.80 (s, 3H). (UPLC-MS) $t_R$ 0.85 min; ESI-MS 430.2 [M+H]$^+$; ESI-MS 428.1 [M−H]$^−$.

Example 68: 4-(3-amino-1H-pyrazolo[4,3-b]pyridin-5-yl)-N-((1r,4r)-4-hydroxy-4-(trifluoromethyl)cyclohexyl)-3-methylbenzenesulfonamide

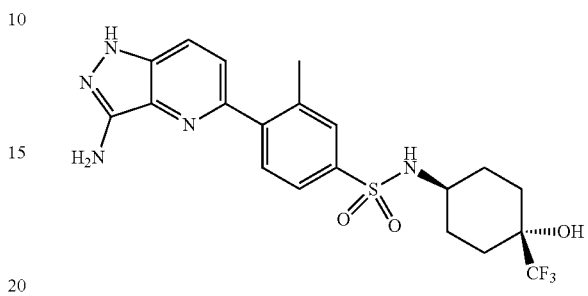

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 4-(6-cyano-5-fluoropyridin-2-yl)-N-((1r,4r)-4-hydroxy-4-(trifluoromethyl)cyclohexyl)-3-methylbenzenesulfonamide (Intermediate 68b). $^1$H NMR (400 MHz, DMSO-d6) δ ppm 11.75 (s, 1H) 7.80 (d, 1H) 7.71-7.78 (m, 3H) 7.62 (d, 1H) 7.45 (d, 1H) 5.66 (s, 1H) 5.41 (br s, 2H) 3.25 (br s, 1H) 2.43 (s, 3H) 1.88-1.77 (m, 2H) 1.76-1.64 (br t, J=13.14 Hz, 2H) 1.57-1.42 (m, 4H). (UPLC-MS) $t_R$ 0.75 min; ESI-MS 470.2 [M+H]$^+$; ESI-MS 468.2 [M−H]$^−$.

Example 69: 4-(3-amino-1H-pyrazolo[4,3-b]pyridin-5-yl)-N-((1s,4s)-4-hydroxycyclohexyl)-3-methylbenzenesulfonamide

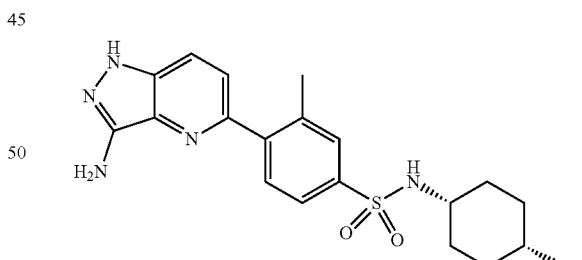

The title compound was prepared in an analogous manner to 5-(4-((hexahydrocyclopenta[c]pyrrol-2(1H)-yl)sulfonyl)-2-methylphenyl)-1H-pyrazolo[4,3-b]pyridin-3-amine (Example 21) using 4-(6-cyano-5-fluoropyridin-2-yl)-N-((1s,4s)-4-hydroxycyclohexyl)-3-methylbenzenesulfonamide (Intermediate 69b). $^1$H NMR (400 MHz, DMSO-d6) δ ppm 11.75 (br s, 1H) 7.80 (d, 1H) 7.75 (s, 1H) 7.74-7.70 (m, 1H) 7.64-7.58 (m, 2H) 7.45 (d, 1H) 5.44 (br s, 2H) 4.34 (br s, 1H) 3.58 (br s, 1H) 3.09-2.93 (m, 1H) 2.42 (s, 3H) 1.64-1.46 (m, 4H) 1.44-1.29 (m, 4H). (UPLC-MS) $t_R$ 0.64 min; ESI-MS 402.3 [M+H]$^+$; ESI-MS 400.2 [M−H]$^−$.

Example 70: (S)-(1-((4-(3-amino-1H-pyrazolo[4,3-b]pyridin-5-yl)-3-methylphenyl)sulfonyl)pyrrolidin-2-yl)methanol

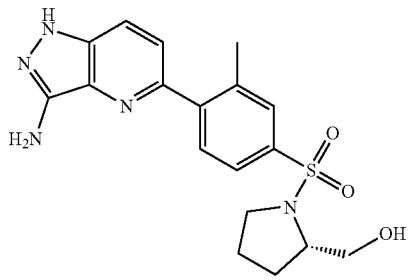 [SMILES: Cc1cc(S(=O)(=O)N2CCC[C@H]2CO)ccc1-c1ccc2[nH]nc(N)c2n1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using (S)-3-fluoro-6-(4-((2-(hydroxymethyl)pyrrolidin-1-yl)sulfonyl)-2-methylphenyl)picolinonitrile (Intermediate 70b). $^1$H NMR (400 MHz, DMSO-$d_6$) δ ppm 11.76 (s, 1H) 7.81 (d, 1H) 7.76 (s, 1H) 7.74-7.70 (m, 1H) 7.68-7.63 (m, 1H) 7.46 (d, 1H) 5.42 (s, 2H) 4.84 (t, 1H) 3.64-3.55 (m, 2H) 3.38-3.32 (m, 2H) 3.16-3.07 (m, 1H) 2.46 (s, 3H) 1.86-1.74 (m, 2H) 1.56-1.39 (m, 2H). (UPLC-MS) $t_R$ 0.65 min; ESI-MS 388.2 [M+H]$^+$; ESI-MS 386.2 [M−H]$^−$.

Example 71: (S)-1-((4-(3-amino-1H-pyrazolo[4,3-b]pyridin-5-yl)-3-chlorophenyl)sulfonyl) pyrrolidin-3-ol

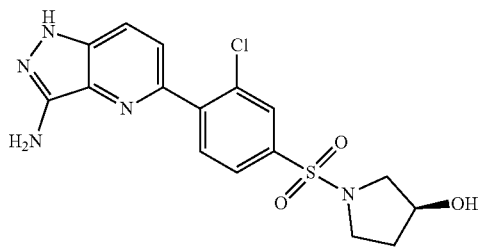 [SMILES: Nc1n[nH]c2ccc(-c3ccc(S(=O)(=O)N4CC[C@H](O)C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using (S)-6-(2-chloro-4-((3-hydroxypyrrolidin-1-yl)sulfonyl)phenyl)-3-fluoropicolinonitrile (Intermediate 71b). $^1$H NMR (400 MHz, DMSO-d6) δ ppm 11.84 (s, 1H) 7.92 (d, 1H) 7.89-7.81 (m, 3H) 7.57 (d, 1H) 5.46 (s, 2H) 4.96 (d, 1H) 4.21 (br d, 1H) 3.40-3.32 (m, 2H) 3.30-3.22 (m, 1H) 3.11 (d, 1H) 1.88-1.78 (m, 1H) 1.75-1.66 (m, 1H). (UPLC-MS) $t_R$ 0.64 min; ESI-MS 394.3 [M+H]$^+$; ESI-MS 392.3 [M−H]$^−$.

Example 72: 4-(3-amino-1H-pyrazolo[4,3-b]pyridin-5-yl)-3-chloro-N-(2-hydroxyethyl)benzenesulfonamide

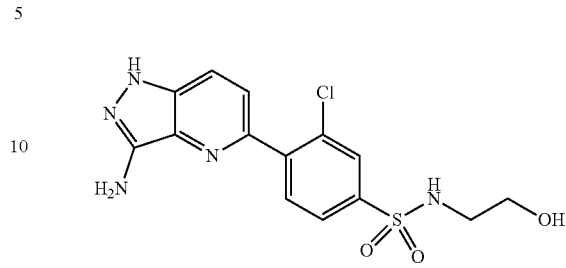

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 3-chloro-4-(6-cyano-5-fluoropyridin-2-yl)-N-(2-hydroxyethyl)benzenesulfonamide (Intermediate 72b). $^1$H NMR (400 MHz, DMSO-$d_6$) δ ppm 11.83 (br s, 1H) 7.94 (s, 1H) 7.88-7.80 (m, 4H) 7.56 (d, 1H) 5.45 (s, 2H) 4.74 (t, 1H) 3.41 (q, 2H) 2.87 (q, 2H). (UPLC-MS) $t_R$ 0.61 min; ESI-MS 368.1 [M+H]$^+$; ESI-MS 366.0 [M−H]$^−$.

Example 73: 4-(3-amino-1H-pyrazolo[4,3-b]pyridin-5-yl)-N-benzyl-3-chlorobenzenesulfonamide

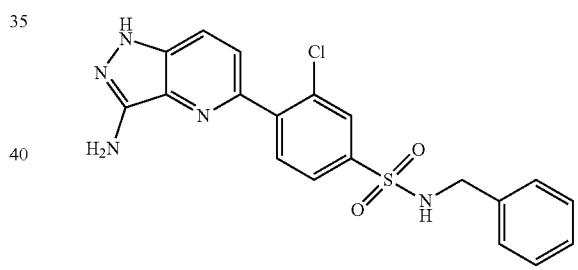

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using N-benzyl-3-chloro-4-(6-cyano-5-fluoropyridin-2-yl)benzenesulfonamide (Intermediate 73b). The reaction mixture was concentrated under reduced pressure without extractive workup. The crude product was purified by reverse phase HPLC (Method 3, 5% to 50% ACN (+7.3 mM NH$_4$OH) in water (+7.3 mM NH$_4$OH)). Fractions were combined, ACN was removed under reduced pressure, and the aq. layer was extracted three times with DCM. The combined organic layers were washed with brine, dried over anhydrous MgSO$_4$, filtered and concentrated under reduced pressure to afford a yellow solid. This material was further purified by silica gel column chromatography (0 to 2% MeOH in DCM) to give the title compound as an off-white solid. $^1$H NMR (400 MHz, DMSO-d6) δ ppm 11.84 (s, 1H) 8.38 (br s, 1H) 7.89-7.76 (m, 4H) 7.54 (d, 1H) 7.34-7.20 (m, 5H) 5.44 (s, 2H) 4.08 (s, 2H). (UPLC-MS) $t_R$ 0.89 min; ESI-MS 414.1 [M+H]$^+$; ESI-MS 412.1 [M−H]$^−$.

Example 74: 5-(2-chloro-4-((3,3-difluoroazetidin-1-yl)sulfonyl)phenyl)-1H-pyrazolo[4,3-b]pyridin-3-amine

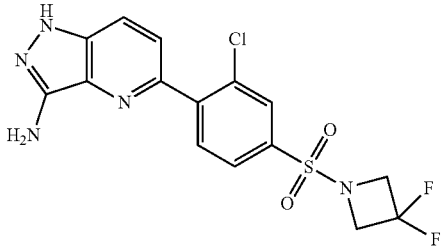 [SMILES: Nc1n[nH]c2ccc(-c3ccc(S(=O)(=O)N4CC(F)(F)C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 6-(2-chloro-4-((3,3-difluoroazetidin-1-yl)sulfonyl)phenyl)-3-fluoropicolinonitrile (Intermediate 74b). $^1$H NMR (400 MHz, DMSO-d6) δ ppm 11.87 (s, 1H) 8.08 (d, 1H) 8.02-7.97 (m, 1H) 7.95-7.91 (m, 1H) 7.85 (d, 1H) 7.59 (d, 1H) 5.48 (s, 2H) 4.40 (t, 4H). (UPLC-MS) $t_R$ 0.85 min; ESI-MS 400.0 [M+H]$^+$; ESI-MS 398.0 [M−H]$^-$.

Example 75: 4-(3-amino-1H-pyrazolo[4,3-b]pyridin-5-yl)-N-tert-butyl-3-fluorobenzenesulfonamide

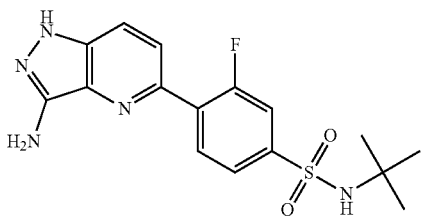 [SMILES: CC(C)(C)NS(=O)(=O)c1ccc(-c2ccc3[nH]nc(N)c3n2)c(F)c1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using N-(tert-butyl)-4-(6-cyano-5-fluoropyridin-2-yl)-3-fluorobenzenesulfonamide (Intermediate 75b). The crude product was purified by preparative HPLC (Method 1, 5% to 95% ACN in water (+0.1% TFA)). Fractions containing pure product were combined, solid NaHCO$_3$ was added, ACN was evaporated under reduced pressure, and the resulting aqueous layer was extracted three times with DCM. The combined organic layers were washed with brine, dried over anhydrous MgSO$_4$, filtered and concentrated under reduced pressure to afford the title compound as a yellow solid. $^1$H NMR (400 MHz, DMSO-d$_6$) δ 11.84 (s, 1H) 8.18 (t, 1H), 7.84 (d, 1H), 7.78 (d, 1H), 7.69-7.76 (m, 3H), 5.50 (s, 2H), 1.15 (s, 9H). (UPLC-MS) $t_R$ 0.82 min; ESI-MS 364.2 [M+H]$^+$; ESI-MS 362.1 [M−H]$^-$.

Example 76: N1-(4-(3-amino-1H-pyrazolo[4,3-b]pyridin-5-yl)-3-chlorophenyl)-N4-methylbenzene-1,4-disulfonamide

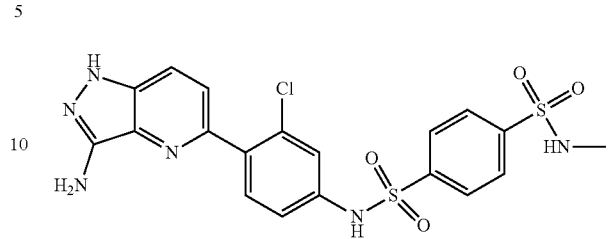

The title compound was prepared in an analogous manner to N-(4-(3-amino-1H-pyrazolo[4,3-b]pyridin-5-yl)-3-chlorophenyl)-4-chlorobenzenesulfonamide (Example 3) using N1-(3-chloro-4-(6-cyano-5-fluoropyridin-2-yl)phenyl)-N4-methylbenzene-1,4-disulfonamide (Intermediate 76b) at 80° C. for 6 h. The residue was purified twice by silica gel column chromatography (0 to 3% MeOH in DCM) to afford the title compound as pale yellow solid. $^1$H NMR (400 MHz, DMSO-d6) δ ppm 11.73 (s, 1H) 10.88 (s, 1H) 8.19 (s, 1H) 8.07 (d, 1H) 8.03 (d, 1H) 7.86 (t, 1H) 7.70-7.76 (m, 2H) 7.49 (d, 1H) 7.39 (d, 1H) 7.24 (s, 1H) 7.20 (dd, 1H) 5.35 (s, 2H) 2.37 (d, 3H). (UPLC-MS) $t_R$ 0.80 min; ESI-MS 493.2 [M+H]$^+$; ESI-MS 491.1 [M−H]$^-$.

Example 77: 4-(3-amino-1H-pyrazolo[4,3-b]pyridin-5-yl)-N-((1r,3r)-3-hydroxycyclobutyl)-3-methylbenzenesulfonamide

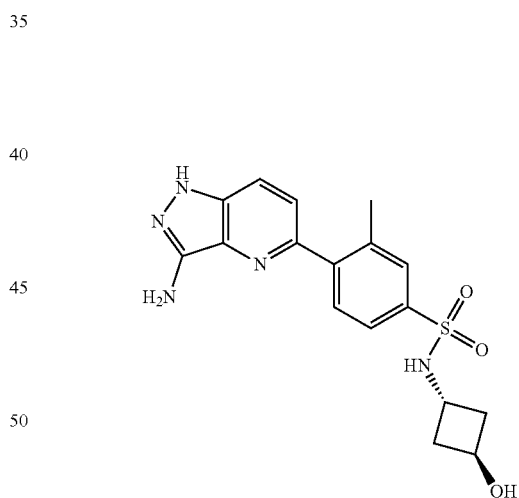

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 4-(6-cyano-5-fluoropyridin-2-yl)-N-((1r,3r)-3-hydroxycyclobutyl)-3-methylbenzenesulfonamide (Intermediate 77b). $^1$H NMR (400 MHz, DMSO-d6) δ ppm 11.75 (s, 1H) 7.90 (d, 1H) 7.80 (d, 1H) 7.71-7.69 (m, 1H) 7.69-7.64 (m, 1H) 7.63-7.59 (m, 1H) 7.44 (d, 1H) 5.41 (br s, 2H) 4.93 (d, 1H) 4.15 (br d, 1H) 3.81-3.71 (m, 1H) 2.43 (s, 3H) 2.05-1.96 (m, 2H) 1.96-1.87 (m, 2H). (UPLC-MS) $t_R$ 0.55 min; ESI-MS 374.1 [M+H]$^+$; ESI-MS 372.1 [M−H]$^-$.

Example 78: N-(4-(3-amino-1H-pyrazolo[4,3-b]pyridin-5-yl)-3-chlorophenyl)-4-(trifluoromethyl)benzenesulfonamide

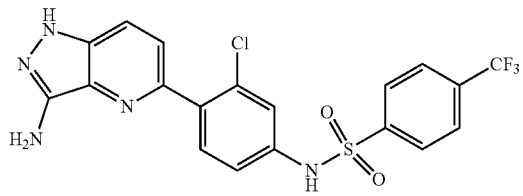 [SMILES: Nc1n[nH]c2ccc(-c3ccc(NS(=O)(=O)c4ccc(C(F)(F)F)cc4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-4-(trifluoromethyl)benzenesulfonamide (Intermediate 78b) at 80° C. for 2.5 h. The residue was purified by silica gel column chromatography (0 to 3% MeOH in DCM) to afford the title compound as yellow solid. $^1$H NMR (400 MHz, DMSO-d6) δ ppm 11.73 (s, 1H) 10.95 (br s, 1H) 7.99-8.09 (m, 4H) 7.74 (d, 1H) 7.50 (d, 1H) 7.41 (d, 1H) 7.27 (d, 1H) 7.21 (dd, 1H) 5.36 (s, 2H). (UPLC-MS) $t_R$ 0.95 min; ESI-MS 468.1 [M+H]$^+$; ESI-MS 466.1 [M−H]$^-$.

Example 79: N-(4-(3-amino-1H-pyrazolo[4,3-b]pyridin-5-yl)-3-chlorophenyl)-3,4-dimethoxybenzenesulfonamide

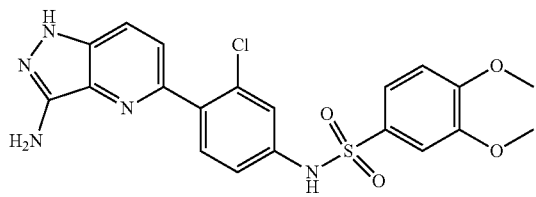 [SMILES: COc1ccc(S(=O)(=O)Nc2ccc(-c3ccc4[nH]nc(N)c4n3)c(Cl)c2)cc1OC]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3,4-dimethoxybenzenesulfonamide (Intermediate 79b) at 80° C. for 3 h. The residue was purified by preparative HPLC (Method 3, 5% to 95% ACN (+7.3 mM NH$_4$OH) in water (+7.3 mM NH$_4$OH)). The residue was further purified by silica gel column chromatography (0 to 3% MeOH in DCM) to afford the title compound as pale yellow solid. $^1$H NMR (400 MHz, DMSO-d6) δ ppm 11.72 (s, 1H) 10.51 (s, 1H) 7.74 (d, 1H) 7.47 (d, 1H) 7.43-7.41 (m, 1H) 7.41-7.38 (m, 1H) 7.34 (d, 1H) 7.26 (d, 1H) 7.19 (dd, Hz, 1H) 7.11 (d, 1H) 5.35 (s, 2H) 3.80 (d, 6H). (UPLC-MS) $t_R$ 0.81 min; ESI-MS 460.2 [M+H]$^+$; ESI-MS 458.1 [M−H]$^-$.

Example 80: 4-(3-amino-1H-pyrazolo[4,3-b]pyridin-5-yl)-N-((1r,4r)-4-hydroxy-4-methylcyclohexyl)-3-methylbenzenesulfonamide

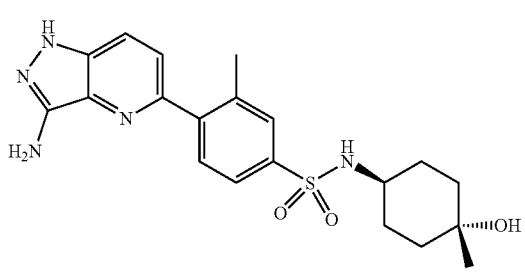 [SMILES: Cc1cc(S(=O)(=O)N[C@H]2CC[C@](C)(O)CC2)ccc1-c1ccc2[nH]nc(N)c2n1]

The title compound was prepared in an analogous manner to 4-(3-amino-1H-pyrazolo[4,3-b]pyridin-5-yl)-3-chloro-N-(3-hydroxycyclohexyl)benzenesulfonamide (Example 44) using 4-(6-cyano-5-fluoropyridin-2-yl)-N-((1r,4r)-4-hydroxy-4-methylcyclohexyl)-3-methylbenzenesulfonamide (Intermediate 80b). $^1$H NMR (400 MHz, DMSO-d6) δ ppm 11.75 (br s, 1H) 7.80 (d, 1H) 7.75 (s, 1H) 7.72 (d, 1H) 7.60 (dd, 2H) 7.45 (d, 1H) 5.42 (br s, 2H) 4.13 (br s, 1H) 3.12-3.03 (m, 1H) 2.42 (s, 3H) 1.67-1.56 (m, 2H) 1.55-1.47 (m, 2H) 1.34-1.22 (m, 4H) 1.06 (s, 3H). (UPLC-MS) $t_R$ 0.64 min; ESI-MS 416.3 [M+H]$^+$; ESI-MS 414.2 [M−H]$^-$.

Example 81: 4-(3-amino-1H-pyrazolo[4,3-b]pyridin-5-yl)-3-chloro-N-(2,3-difluorophenyl)benzenesulfonamide

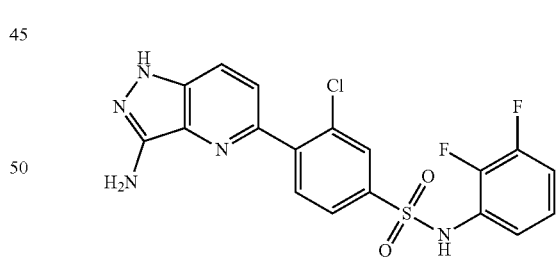

The title compound was prepared in an analogous manner to 4-(3-amino-1H-pyrazolo[4,3-b]pyridin-5-yl)-3-chloro-N-(2,3-dichlorophenyl)benzenesulfonamide (Example 56) using 3-chloro-4-(6-cyano-5-fluoropyridin-2-yl)-N-(2,3-difluorophenyl)benzenesulfonamide (Intermediate 81 b). $^1$H NMR (400 MHz, DMSO-d$_6$) δ ppm 11.85 (br s, 1H) 10.72 (br s, 1H) 7.90 (d, 1H) 7.85-7.77 (m, 3H) 7.55 (d, 1H) 7.34-7.26 (m, 1H) 7.23-7.15 (m, 1H) 7.15-7.09 (m, 1H) 5.47 (br s, 2H). (UPLC-MS) $t_R$ 0.87 min; ESI-MS 436.2 [M+H]$^+$; ESI-MS 434.2 [M−H]$^-$.

Example 82: N-(4-(3-amino-1H-pyrazolo[4,3-b]pyridin-5-yl)-3-chlorophenyl)naphthalene-2-sulfonamide

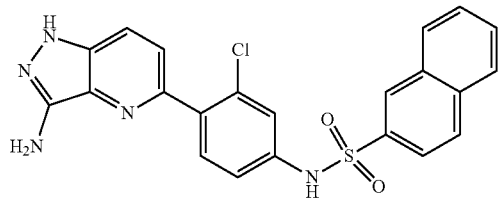 [SMILES: Nc1n[nH]c2ccc(-c3ccc(NS(=O)(=O)c4ccc5ccccc5c4)cc3Cl)nc12]

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)naphthalene-2-sulfonamide (Intermediate 82b) at 80° C. for 4 h. The residue was purified by reverse phase column chromatography (Method 2, 5% to 40% ACN in water) to afford the title compound as yellow solid. $^1$H NMR (600 MHz, DMSO-d6) δ ppm 11.70 (s, 1H) 10.85 (br s, 1H) 8.56 (s, 1H) 8.19 (d, 1H) 8.15 (d, 1H) 8.03 (d, 1H) 7.84 (dd, 1H) 7.66-7.75 (m, 3H) 7.43 (d, 1H) 7.36 (d, 1H) 7.29 (d, 1H) 7.23 (dd, 1H) 5.35 (s, 2H). (UPLC-MS) $t_R$ 0.94 min; ESI-MS 450.1 [M+H]$^+$; ESI-MS 448.1 [M−H]$^−$.

Example 83: 2-(1-((4-(3-amino-1H-pyrazolo[4,3-b]pyridin-5-yl)-3-methylphenyl)sulfonyl)pyrrolidin-3-yl)ethanol

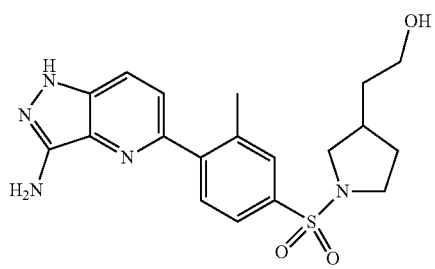 [SMILES: Cc1cc(S(=O)(=O)N2CCC(CCO)C2)ccc1-c1ccc2[nH]nc(N)c2n1]

The title compound was prepared in an analogous manner to 5-(4-((hexahydrocyclopenta[c]pyrrol-2(1H)-yl)sulfonyl)-2-methylphenyl)-1H-pyrazolo[4,3-b]pyridin-3-amine (Example 21) except 3-fluoro-6-(4-((3-(2-hydroxyethyl)pyrrolidin-1-yl)sulfonyl)-2-methylphenyl)picolinonitrile (Intermediate 83b) was used in place of 3-fluoro-6-(4-((hexahydrocyclopenta[c]pyrrol-2(1H)-yl)sulfonyl)-2-methylphenyl)picolinonitrile (Intermediate 21b). $^1$H NMR (400 MHz, DMSO-d6) δ ppm 11.76 (s, 1H) 7.81 (d, 1H) 7.74 (s, 1H) 7.72-7.69 (m, 1H) 7.67-7.63 (m, 1H) 7.46 (d, 1H) 5.42 (br s, 2H) 4.42 (br t, 1H) 3.47-3.40 (m, 1H) 3.26-3.39 (m, 3H) 3.09-3.18 (m, 1H) 2.74-2.83 (m, 1H) 2.45 (s, 3H) 2.11-1.98 (m, 1H) 1.96-1.86 (m, 1H) 1.41-1.31 (m, 2H). (UPLC-MS) $t_R$ 0.68 min; ESI-MS 402.3 [M+H]$^+$; ESI-MS 400.3 [M−H]$^−$.

Example 84: N-(4-(3-amino-1H-pyrazolo[4,3-b]pyridin-5-yl)-3-chlorophenyl)-3-methylbenzenesulfonamide

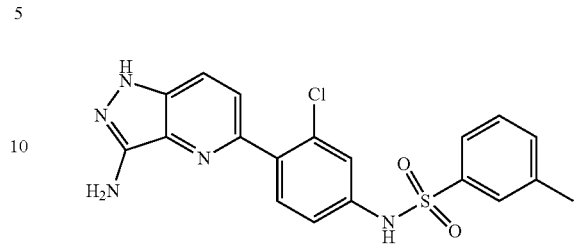

The title compound was prepared in an analogous manner to N-(4-(3-amino-1H-pyrazolo[4,3-b]pyridin-5-yl)-3-chlorophenyl)-4-chlorobenzenesulfonamide (Example 3) using N-(3-chloro-4-(6-cyano-5-fluoropyridin-2-yl)phenyl)-3-methylbenzenesulfonamide (Intermediate 84b) at 80° C. for 2 h. The residue was purified by preparative HPLC (Method 1, 5 to 65% ACN in water (+0.1% TFA)). The residue was further purified by silica gel column chromatography (0 to 3% MeOH in DCM) to afford the title product as pale yellow solid. $^1$H NMR (400 MHz, DMSO-d6) δ ppm 11.72 (s, 1H) 10.67 (s, 1H) 7.74 (d, 1H) 7.67 (s, 1H) 7.64 (br d, 1H) 7.52-7.45 (m, 3H) 7.40 (d, 1H) 7.24 (d, 1H) 7.19 (dd, 1H) 5.35 (br s, 2H) 2.38 (s, 3H). (UPLC-MS) $t_R$ 0.88 min; ESI-MS 414.2 [M+H]$^+$; ESI-MS 412.1 [M−H]$^−$.

Example 85: 4-(3-amino-1H-pyrazolo[4,3-b]pyridin-5-yl)-3-chloro-N-((1s,3s)-3-(hydroxymethyl)cyclobutyl)benzenesulfonamide

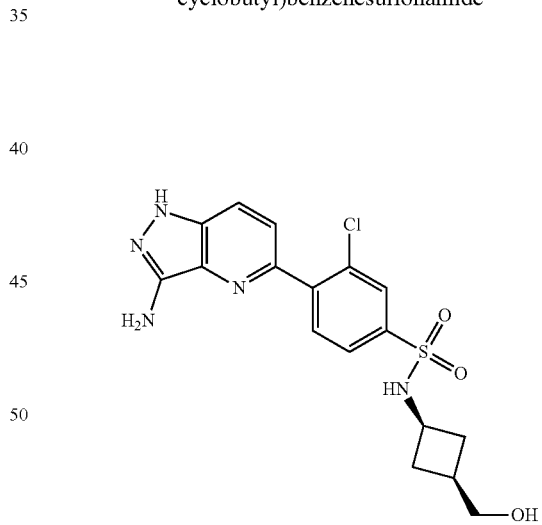

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-((1s,3s)-3-(hydroxymethyl)cyclobutyl)benzenesulfonamide (Intermediate 85b). $^1$H NMR (400 MHz, DMSO-d$_6$) δ ppm 11.83 (s, 1H) 8.07 (d, 1H) 7.92 (d, 1H) 7.87-7.79 (m, 3H) 7.56 (d, 1H) 5.45 (s, 2H) 4.45 (t, 1H) 3.65-3.53 (m, 1H) 3.24 (t, 2H) 2.06-1.86 (m, 3H) 1.58-1.45 (m, 2H). (UPLC-MS) $t_R$ 0.66 min; ESI-MS 408.1 [M+H]$^+$; ESI-MS 406.1 [M−H]$^−$.

Example 86: 4-acetyl-N-(4-(3-amino-1H-pyrazolo[4,3-b]pyridin-5-yl)-3-chlorophenyl)-3,4-dihydro-2H-benzo[b][1,4]oxazine-6-sulfonamide

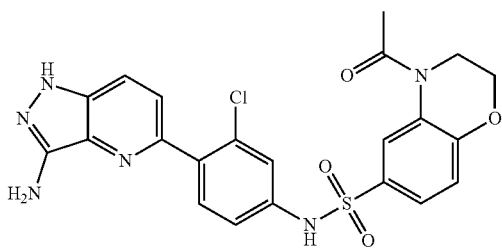 [SMILES: CC(=O)N1CCOc2ccc(S(=O)(=O)Nc3ccc(-c4ccc5[nH]nc(N)c5n4)c(Cl)c3)cc21]

The title compound was prepared in an analogous manner to N-(4-(3-amino-1H-pyrazolo[4,3-b]pyridin-5-yl)-3-chlorophenyl)-2-hydroxycyclohexane-1-sulfonamide (Example 17) using 4-acetyl-N-(3-chloro-4-(6-cyano-5-fluoropyridin-2-yl)phenyl)-3,4-dihydro-2H-benzo[b][1,4]oxazine-6-sulfonamide (Intermediate 86b) at 80° C. for 1 h. The residue was purified three times using reverse phase column chromatography (Method 2, 2-100% ACN in water) to afford the title compound. $^1$H NMR (400 MHz, DMSO-d6) δ ppm 11.72 (s, 1H) 10.64 (s, 1H) 7.74 (d, 1H) 7.52-7.44 (m, 2H) 7.40 (d, 1H) 7.25 (d, 1H) 7.20 (dd, 1H) 7.07 (d, 1H) 5.37-5.30 (m, 2H) 4.33 (t, 2H) 3.87 (t, 2H) 2.22 (br s, 3H). (UPLC-MS) $t_R$ 0.78 min; ESI-MS 499.2 [M+H]$^+$; ESI-MS 497.1 [M–H]$^-$.

Example 87: 5-(2-chloro-4-((3-phenoxyazetidin-1-yl)sulfonyl)phenyl)-1H-pyrazolo[4,3-b]pyridin-3-amine

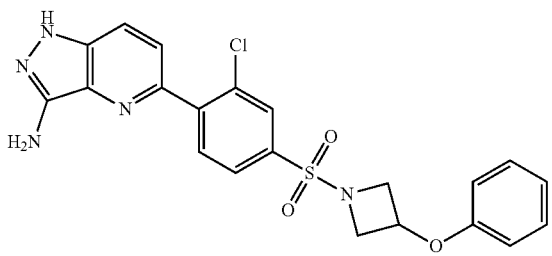 [SMILES: Nc1n[nH]c2ccc(-c3ccc(S(=O)(=O)N4CC(Oc5ccccc5)C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 6-(2-chloro-4-((3-phenoxyazetidin-1-yl)sulfonyl)phenyl)-3-fluoropicolinonitrile (Intermediate 87b). $^1$H NMR (400 MHz, DMSO-d6) δ 11.86 (s, 1H) 8.01-7.98 (m, 1H) 7.93 (d, 2H) 7.86 (d, 1H) 7.60 (d, 1H) 7.30-7.22 (m, 2H) 7.00-6.93 (m, 1H) 6.80-6.73 (m, 2H) 5.46 (br s, 2H) 4.97-4.88 (m, 1H) 4.34 (dd, 2H) 3.74 (dd, 2H). (UPLC-MS) $t_R$ 0.96 min; ESI-MS 456.2 [M+H]$^+$; ESI-MS 454.1 [M–H]$^-$.

Example 88: N-(4-(3-amino-1H-pyrazolo[4,3-b]pyridin-5-yl)-3-chlorophenyl)-4-(trifluoromethoxy)benzenesulfonamide

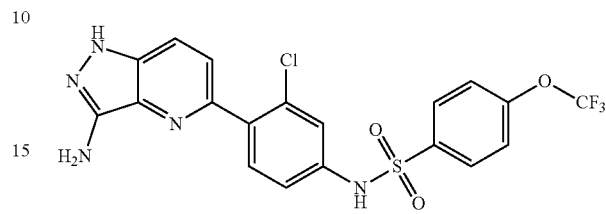

The title compound was prepared in an analogous manner to N-(4-(3-amino-1H-pyrazolo[4,3-b]pyridin-5-yl)-3-chlorophenyl)-2-hydroxycyclohexane-1-sulfonamide (Example 17) using N-(3-chloro-4-(6-cyano-5-fluoropyridin-2-yl)phenyl)-4-(trifluoromethoxy)benzenesulfonamide (Intermediate 88b) at 80° C. for 1 h. The residue was purified by silica gel column chromatography (0 to 20% MeOH in DCM) to afford the title compound as colorless oil. $^1$H NMR (400 MHz, DMSO-d$_6$) δ ppm 11.73 (s, 1H) 10.85 (s, 1H) 7.97 (d, 2H) 7.74 (d, 1H) 7.62 (br d, 2H) 7.50 (d, 1H) 7.41 (d, 1H) 7.25 (s, 1H) 7.20 (br d, 1H) 5.36 (s, 2H). (UPLC-MS) $t_R$ 0.94 min; ESI-MS 484.2 [M+H]$^+$; ESI-MS 482.2 [M–H]$^-$.

Example 89: 2-(4-((4-(3-amino-1H-pyrazolo[4,3-b]pyridin-5-yl)-3-chlorophenyl)sulfonyl)piperazin-2-yl)-1,1,1-trifluoropropan-2-ol

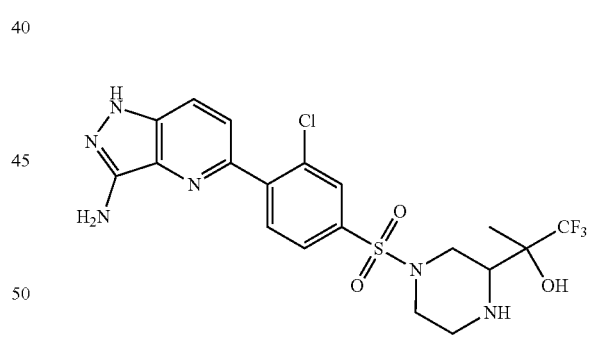

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 6-(2-chloro-4-((3-(1,1,1-trifluoro-2-hydroxypropan-2-yl)piperazin-1-yl)sulfonyl)phenyl)-3-fluoropicolinonitrile (Intermediate 89b). Purification by silica gel column chromatography was repeated twice to remove impurities from the title compound. $^1$H NMR (400 MHz, DMSO-d6) δ ppm 11.88 (s, 1H), 7.92 (d, 1H), 7.88-7.80 (m, 3H), 7.60 (d, 1H), 6.18 (s, 1H), 5.47 (s, 2H), 3.76 (d, 1H), 3.55 (d, 1H), 3.02 (d, 1H), 2.20-2.10 (m, 4H), 1.26 (s, 3H), 1.10-1.25 (m, 1H). (UPLC-MS) $t_R$ 0.71 min; ESI-MS 505.2 [M+H]$^+$; ESI-MS 503.2 [M–H]$^-$.

Example 90: 4-(3-amino-1H-pyrazolo[4,3-b]pyridin-5-yl)-3-chloro-N-(3-chlorophenyl)benzenesulfonamide

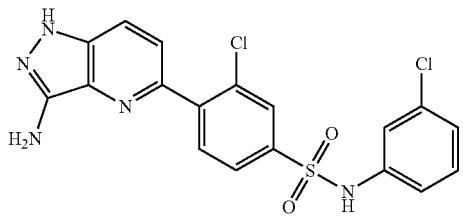 [SMILES: Nc1n[nH]c2ccc(-c3ccc(S(=O)(=O)Nc4cccc(Cl)c4)cc3Cl)nc12]

The title compound was prepared in an analogous manner to 4-(3-amino-1H-pyrazolo[4,3-b]pyridin-5-yl)-3-chloro-N-(2,3-dichlorophenyl)benzenesulfonamide (Example 56) using 3-chloro-N-(3-chlorophenyl)-4-(6-cyano-5-fluoropyridin-2-yl)benzenesulfonamide (Intermediate 90b). After preparative HPLC (Method 1), fractions containing pure product were combined, solid NaHCO₃ was added, ACN was evaporated under reduced pressure, and the resulting aq. layer was extracted three times with DCM. The combined organic layers were washed with brine, dried over anhydrous MgSO₄, filtered and concentrated under reduced pressure to afford the title compound as an off-white solid. ¹H NMR (400 MHz, 400 MHz, DMSO-d6) δ ppm 11.85 (s, 1H), 10.79 (s, 1H), 7.93 (d, 1H), 7.87-7.79 (m, 3H), 7.55 (d, 1H), 7.35 (t, 1H), 7.20 (d, 1H), 7.16 (d, 2H), 5.48 (s, 2H). (UPLC-MS) $t_R$ 0.97 min; ESI-MS 434.1/436.1 [M+H]⁺. ESI-MS 432.0/434.1 [M–H]⁻.

Example 91: 4-(3-amino-1H-pyrazolo[4,3-b]pyridin-5-yl)-N-(2-hydroxycyclohexyl)-3-methylbenzenesulfonamide

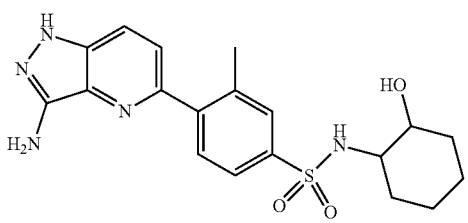 [SMILES: Cc1cc(S(=O)(=O)NC2CCCCC2O)ccc1-c1ccc2[nH]nc(N)c2n1]

The title compound was prepared in an analogous manner to 4-(3-amino-1H-pyrazolo[4,3-b]pyridin-5-yl)-3-chloro-N-((1R,2S)-2-hydroxycyclopentyl)benzenesulfonamide (Example 7) using 4-(6-cyano-5-fluoropyridin-2-yl)-N-(2-hydroxycyclohexyl)-3-methylbenzenesulfonamide (Intermediate 91b). The crude product was purified first by preparative HPLC (Method 1, 5% to 95% ACN in water (+0.1% TFA)). Fractions containing pure product were combined and passed through a PL-HCO3 MP cartridge (Stratospheres, pre-conditioned with MeOH), following by wash out with MeOH. The filtrate was concentrated under reduced pressure, and the residue was further purified by silica gel chromatography (0 to 11% MeOH in DCM) and by preparative achiral SFC (Column Waters VIRIDIS BEH 250× 30 mm, 5 μm, 100A; 18% to 22% CO₂ in MeOH) to afford the title compound as yellow solid. ¹H NMR (400 MHz, DMSO-d₆) δ ppm 11.74 (s, 1H) 7.82-7.77 (m, 2H) 7.74 (d, 1H) 7.58 (d, 1H) 7.44 (d, 1H) 7.31 (d, 1H) 5.41 (s, 2H) 4.53 (d, 1H) 3.62 (br s, 1H) 3.13-3.04 (m, 1H) 2.42 (s, 3H) 1.65-1.29 (m, 4H) 1.28-1.05 (m, 4H). (UPLC-MS) $t_R$ 0.73 min; ESI-MS 402.3 [M+H]⁺; ESI-MS 400.2 [M–H]⁻.

Example 92: 4-(3-amino-1H-pyrazolo[4,3-b]pyridin-5-yl)-3-chloro-N-(1,1-dioxidothietan-3-yl)benzenesulfonamide

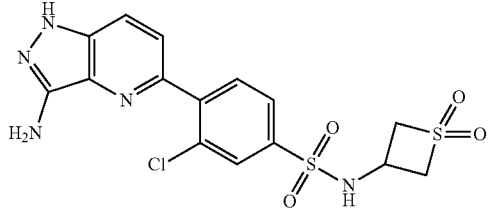 [SMILES: Nc1n[nH]c2ccc(-c3ccc(S(=O)(=O)NC4CS(=O)(=O)C4)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-(1,1-dioxidothietan-3-yl) benzenesulfonamide (Intermediate 92b). After extractive workup, the crude compound underwent purification by reverse phase column chromatography (5% to 95% ACN in water (+0.1% TFA)). Fractions containing pure product were combined, a sat. aq. NaHCO₃ solution was added, and the resulting mixture was extracted three times with EtOAc. The combined organic layers were washed with brine, dried over anhydrous MgSO₄, filtered and concentrated under reduced pressure to afford the title compound as a colorless solid. ¹H NMR (400 MHz, DMSO-d6) δ 11.86 (s, 1H), 7.95 (s, 1H), 7.85 (d, 3H), 7.59 (d, 1H), 5.45 (s, 2H), 4.49 (s, 2H), 4.04 (d, 3H). (UPLC-MS) $t_R$ 0.66 min; ESI-MS 428.1 [M+H]⁺; ESI-MS 426.1 [M–H]⁻.

Example 93: 5-(2-chloro-4-((3-(methylsulfonyl)azetidin-1-yl)sulfonyl)phenyl)-1H-pyrazolo[4,3-b]pyridin-3-amine

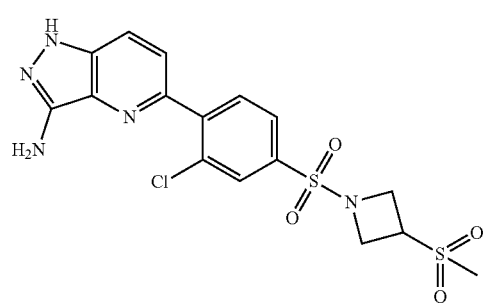 [SMILES: CS(=O)(=O)C1CN(S(=O)(=O)c2ccc(-c3ccc4[nH]nc(N)c4n3)c(Cl)c2)C1]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 6-(2-chloro-4-((3-(methylsulfonyl)azetidin-1-yl)sulfonyl)phenyl)-3-fluoropicolinonitrile (Intermediate 93b). Purification by silica gel column chromatography was repeated to remove impurities from the title compound. ¹H NMR (400 MHz, DMSO-d6) δ ppm 11.87 (s, 1H) 7.99 (s, 1H) 7.95-7.89 (m, 2H) 7.85 (d, 1H) 7.57 (d, 1H) 5.47 (s, 2H) 4.34-4.24 (m, 1H)

4.14 (t, 2H) 4.09-4.02 (m, 2H) 2.96 (s, 3H). (UPLC-MS) $t_R$ 0.68 min; ESI-MS 442.2 [M+H]$^+$; ESI-MS 440.2 [M−H]$^−$.

Example 94: 4-(3-amino-1H-pyrazolo[4,3-b]pyridin-5-yl)-3-chloro-N-((1S,2S)-2-hydroxycyclopentyl)benzenesulfonamide

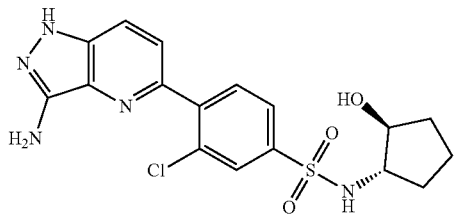 [SMILES: Nc1n[nH]c2ccc(-c3ccc(S(=O)(=O)N[C@H]4CCC[C@@H]4O)cc3Cl)nc12]

The title compound was prepared in an analogous manner to 4-(3-amino-1H-pyrazolo[4,3-b]pyridin-5-yl)-3-chloro-N-((1s,3s)-3-hydroxy-3-(trifluoromethyl)cyclobutyl)benzenesulfonamide (Example 1) using 3-chloro-4-(6-cyano-5-fluoropyridin-2-yl)-N-((1S,2S)-2-hydroxycyclopentyl)benzenesulfonamide (Intermediate 94b). After extractive workup, the crude product was purified by preparative HPLC (Method 1, 5% to 95% ACN in water (+0.1% TFA)). Fractions containing pure product were combined, a sat. aq. NaHCO$_3$ solution was added, and the resulting mixture was extracted three times with EtOAc. The combined organic layers were washed with brine, dried over anhydrous MgSO$_4$, filtered and concentrated under reduced pressure to afford the title compound as a colorless solid. $^1$H NMR (400 MHz, DMSO-d6) δ ppm 11.83 (br s, 1H) 7.96 (d, 1H) 7.89-7.85 (m, 1H) 7.85-7.77 (m, 3H) 7.56 (d, 1H) 5.45 (s, 2H) 4.73 (d, 1H) 3.84-3.78 (m, 1H) 3.28-3.21 (m, 1H) 1.82-1.69 (m, 2H) 1.59-1.50 (m, 2H) 1.43-1.22 (m, 2H). (UPLC-MS) $t_R$ 0.67 min; ESI-MS 408.2 [M+H]$^+$; ESI-MS 406.1 [M−H]$^−$.

Example 95—In Vitro, Ex Vivo and In Vivo Assays

SCX-LUC In Vitro Assay

Scleraxis (Scx) is a tendon cell specific transcription factor. Based on the literature Scx appears to act early in the tendon cell differentiation pathway. A 1.5 kb stretch of genomic sequence upstream of the Scx coding region was cloned into the pGreenFire1 lentiviral reporter construct. This construct was used to make a stable line in TT-D6 immortalized cells that expresses Luciferase upon Scx transcriptional activation.

To determine transcriptional activation of Scleraxis (Scx) gene after treatment with the compounds of the invention, a mouse immortalized TT-D6 Scx-luciferase (ScxL) cell line was first seeded in a white, solid bottom 384 well plate (Greiner, cat #789163-G) in 50 ul media (Alpha MEM, 10% FBS, 1% pen-strep; Gibco, cat #12571048 and 15140122) supplemented with 1 ng/ml TGFβ1 (PeproTech, cat #100-21) at a density of 6,000 cells/well. Cells were then treated with a serial dilution (1:3) of the compounds of the invention or DMSO alone for four days at 37° C. After the incubation period, media was removed and 20 ul Bright-Glo Reagent (Promega, cat #E2620) was added to the wells. Immediately, luciferase luminescence was read on a SprectraMax M5E plate reader with 50 ms integration.

The results are shown in the table below.

Ex Vivo Assays

Tenogenic differentiation was measured ex vivo looking at mRNA levels for both tenogenic and extracellular matrix genes. Both Scleraxis (Sex) and Tenomodulin (Tnmd) genes have been shown to be enriched in tendon cells and associated with tenogenesis while an increase in tendon collagen type I (Col1a2) is secondary to tenogenic differentiation and is necessary for proper healing.

To determine ex vivo gene expression changes after stimulation with compounds of the invention, tendon fascicles were first removed from approximately 2-3 month old male Sprague Dawley rat tails. The tendon fascicles were washed in Hank's Balanced Salt Solution (HBSS, Hyclone, GE cat #SH30268.01) before being cut into 2.5 cm length pieces. Next, two tendon fascicle pieces were placed per well in a 48 well tissue culture plate containing 1 ml of Mesenchymal Stem Cell Growth Media (MSCGM, Lonza, cat #PT-3001) with serial dilutions (1:2) of compounds or DMSO alone. Tendon fascicles were then stimulated at 37° C. for four days in a cell culture incubator. RNA was isolated after the incubation period from the tendon fascicles using the RNeasy 96 Kit (Qiagen, cat #74181). cDNA was then synthesized from the RNA using Quanta's qScript Supermix (VWR, cat #101414-106) and thermocycler protocol: 25° C. for 5 minutes, 42° C. for 45 minutes, 85° C. for 5 minutes, hold at 4° C. Using SYBR green (Roche, cat #04707516001), qPCR reactions were carried out in a Roche Lightcycler 480 II (Software version: 1.5.0 SP3, Roche cat #05015243001) using the following cycling protocol: pre-incubation for 10 minutes at 95° C. followed by 45 amplification cycles of 10 seconds at 95° C., 10 seconds at 60° C. and 20 seconds at 72° C. Finally, gene expression data was calculated by using the delta-delta Ct method using the average of 3 housekeeping genes (Gadph, B-actin and 36b4).

| Gene name | Forward primer | Reverse primer |
|---|---|---|
| Gadph | ATC ACC ATC TTC CAG GAG CGA (SEQ ID NO: 1) | AGC CTT CTC CAT GGT GGT GAA (SEQ ID NO: 7) |
| 36b4 | GAT GCC CAG GGA AGA CAG (SEQ ID NO: 2) | CAC AAT GAA GCA TTT TGG GTA G (SEQ ID NO: 8) |
| Beta-actin | GCT CCT CCT GAG CGC AAG (SEQ ID NO: 3) | CAT CTG CTG GAA GGT GGA CA (SEQ ID NO: 9) |
| Scleraxis | CCC AAA CAG ATC TGC ACC TT (SEQ ID NO: 4) | TCT GTC ACG GTC TTT GCT CA (SEQ ID NO: 10) |

Primer sequences

-continued

| Gene name | Forward primer | Reverse primer |
|---|---|---|
| Tenomodulin | TGG ATC AAT CCC ACT CTA ATA GC (SEQ ID NO: 5) | TCG CTG GTA GGA AAG TGA AGA (SEQ ID NO: 11) |
| Collagen type 1 (col1a2) | CCT GGC TCT CGA GGT GAA C (SEQ ID NO: 6) | CAA TGC CCA GAG GAC CAG (SEQ ID NO: 12) |

The results are shown in the table below and show that compounds of the invention For the Scx-Luc assay, $EC_{50}$ values were obtained using luciferase luminescence read on a SprectraMax M5E plate reader.

For the ex vivo assays, $EC_{50}$ calculations were done using delta-delta Ct values for each gene calculated using the average of 3 housekeeping genes.

| Example | Scx-Luc ($EC_{50}$ μM) | Ex vivo Scx ($EC_{50}$ μM) | Ex vivo Tnmd ($EC_{50}$ μM) | Ex vivo Col1a2 ($EC_{50}$ μM) |
|---|---|---|---|---|
| 1 | 0.183 | 2.108 | 0.804 | 1.586 |
| 2 | 0.376 | n.d. | n.d. | n.d. |
| 3 | 0.801 | >10 | 1.153 | 3.079 |
| 4 | 0.444 | n.d. | n.d. | n.d. |
| 5 | 0.909 | n.d. | n.d. | n.d. |
| 6 | 0.580 | n.d. | n.d. | n.d. |
| 7 | 0.305 | 1.602 | 1.681 | 2.062 |
| 8 | 0.346 | 0.110 | 0.261 | 1.292 |
| 9 | 0.460 | 2.271 | 2.141 | 0.577 |
| 10 | 0.640 | n.d. | n.d. | n.d. |
| 11 | 0.801 | 3.048 | 0.841 | 2.458 |
| 12 | 0.765 | 5.793 | 5.387 | 4.623 |
| 13 | 1.343 | n.d. | n.d. | n.d. |
| 14 | 1.119 | n.d. | n.d. | n.d. |
| 15 | 0.874 | n.d. | n.d. | n.d. |
| 16 | 0.610 | 3.864 | 2.807 | 4.646 |
| 17 | 1.840 | n.d. | n.d. | n.d. |
| 18 | 0.764 | 1.767 | 0.750 | 1.827 |
| 19 | 1.698 | n.d. | n.d. | n.d. |
| 20 | 0.797 | n.d. | n.d. | n.d. |
| 21 | 0.598 | 4.927 | 3.508 | 3.709 |
| 22 | 0.035 | n.d. | n.d. | n.d. |
| 23 | 2.278 | n.d. | n.d. | n.d. |
| 24 | 1.592 | n.d. | n.d. | n.d. |
| 25 | 0.611 | n.d. | n.d. | n.d. |
| 26 | 0.811 | n.d. | n.d. | n.d. |
| 27 | 1.083 | n.d. | n.d. | n.d. |
| 28 | 2.500 | n.d. | n.d. | n.d. |
| 29 | 1.909 | n.d. | n.d. | n.d. |
| 30 | 2.067 | n.d. | n.d. | n.d. |
| 31 | 0.411 | 2.314 | 2.762 | 2.634 |
| 32 | 1.937 | n.d. | n.d. | n.d. |
| 33 | 1.025 | n.d. | n.d. | n.d. |
| 34 | 5.021 | n.d. | n.d. | n.d. |
| 35 | 2.729 | n.d. | n.d. | n.d. |
| 36 | 0.414 | n.d. | n.d. | n.d. |
| 37 | 0.593 | n.d. | n.d. | n.d. |
| 38 | 0.610 | 0.188 | 1.892 | 0.396 |
| 39 | 0.473 | n.d. | n.d. | n.d. |
| 40 | 0.416 | n.d. | n.d. | n.d. |
| 41 | 2.250 | n.d. | n.d. | n.d. |
| 42 | 2.001 | n.d. | n.d. | n.d. |
| 43 | 3.309 | n.d. | n.d. | n.d. |
| 44 | 4.122 | n.d. | n.d. | n.d. |
| 45 | 4.725 | n.d. | n.d. | n.d. |
| 46 | 0.010 | n.d. | n.d. | n.d. |
| 47 | 5.341 | n.d. | n.d. | n.d. |
| 48 | 2.025 | n.d. | n.d. | n.d. |
| 49 | 0.870 | n.d. | n.d. | n.d. |
| 50 | >10 | 2.325 | 6.301 | 6.372 |
| 51 | 2.391 | n.d. | n.d. | n.d. |
| 52 | 1.104 | n.d. | n.d. | n.d. |
| 53 | 2.737 | n.d. | n.d. | n.d. |
| 54 | 1.127 | n.d. | n.d. | n.d. |
| 55 | 6.157 | n.d. | n.d. | n.d. |
| 56 | 1.638 | n.d. | n.d. | n.d. |
| 57 | 0.633 | n.d. | n.d. | n.d. |
| 58 | 1.514 | n.d. | n.d. | n.d. |
| 59 | 4.319 | >10 | 4.614 | 5.706 |
| 60 | 3.040 | n.d. | n.d. | n.d. |
| 61 | 1.540 | n.d. | n.d. | n.d. |
| 62 | 1.300 | n.d. | n.d. | n.d. |
| 63 | 1.239 | 2.125 | 4.602 | 3.344 |
| 64 | 0.162 | n.d. | n.d. | n.d. |
| 65 | 0.122 | n.d. | n.d. | n.d. |
| 66 | 0.794 | 0.890 | 0.719 | 0.921 |
| 67 | 2.317 | n.d. | n.d. | n.d. |
| 68 | 0.354 | n.d. | n.d. | n.d. |
| 69 | 0.912 | n.d. | n.d. | n.d. |
| 70 | 0.762 | n.d. | n.d. | n.d. |
| 71 | 3.532 | n.d. | n.d. | n.d. |
| 72 | 4.091 | 3.937 | 3.421 | 3.283 |
| 73 | 3.533 | n.d. | n.d. | n.d. |
| 74 | 2.033 | n.d. | n.d. | n.d. |
| 75 | 1.523 | n.d. | n.d. | n.d. |
| 76 | 0.003 | n.d. | n.d. | n.d. |
| 77 | 0.777 | n.d. | n.d. | n.d. |
| 78 | 2.435 | n.d. | n.d. | n.d. |
| 79 | 0.061 | n.d. | n.d. | n.d. |
| 80 | 0.225 | n.d. | n.d. | n.d. |
| 81 | 0.203 | n.d. | n.d. | n.d. |
| 82 | 2.609 | >10 | 4.874 | 7.274 |
| 83 | 5.328 | n.d. | n.d. | n.d. |
| 84 | 0.045 | n.d. | n.d. | n.d. |
| 85 | 1.754 | n.d. | n.d. | n.d. |
| 86 | 5.387 | >10 | 4.864 | >10 |
| 87 | 0.830 | n.d. | n.d. | n.d. |
| 88 | 2.430 | n.d. | n.d. | n.d. |
| 89 | 2.186 | 4.444 | 5.007 | 7.273 |
| 90 | 2.542 | n.d. | n.d. | n.d. |
| 91 | 1.815 | n.d. | n.d. | n.d. |
| 92 | 0.968 | 4.889 | 6.281 | 1.352 |
| 93 | 5.740 | 2.951 | 3.524 | 1.759 |
| 94 | 0.026 | n.d. | n.d. | n.d. |

The compounds (S)-(1-((4-(3-amino-1H-pyrazolo[4,3-b]pyridin-5-yl)-3-chlorophenyl)sulfonyl)pyrrolidin-2-yl)methanol and 4-(3-amino-1H-pyrazolo[4,3-b]pyridin-5-yl)-3-chloro-N-((1R,4R)-4-hydroxy-4-(trifluoromethyl)cyclohexyl)benzenesulfonamide exhibit efficacy in the Scx-Luc assay described above with an $EC_{50}$>10 μM.

The data shown in the table above shows that the compounds of the invention have activity as inducers of scleraxis, tenomodulin and collagen type I suggesting that the compounds are useful in the treatment of tendon injuries.

In Vivo Assay

Animals are treated 3 days post-surgery with 1 mg of compound in 10 μl of vehicle delivered by injection under the skin in the peri-tendinous region. Tendons are harvested 25 days post treatment. Strong Alcian blue staining is used to detect endochondral tissue forming which further ossifies with time. A comparison between vehicle treated animals and animals treated with a compound of the invention can be made. Treatment with a compound of the invention is expected to be able to counter some of the improper healing caused by aberrant differentiation towards the chondrogenic and osteogenic lineages. Definiens Tissue Studio software can be used for quantitative image analysis of the Alcian blue positive area. Serial step sections encompassing 2 mm of the lesion are used for quantification.

Example 96: Ex Vivo Fascicle Assay

Sample Preparation

Tail from skeletal mature rat (Sprague Dawley, female, 30-50 weeks old) is removed and kept on ice. Approximately 40 mm long segment is cut from the mid-portion of the tail. Rat tail fascicles (n=12) were carefully extracted from the segment. Fascicles are then randomly selected into three groups, fresh (n=4), vehicle (n=4) and 4-(3-amino-1H-pyrazolo[4,3-b]pyridin-5-yl)-N-((1s,3s)-3-hydroxy-3-(trifluoromethyl)cyclobutyl)-3-methyl benzenesulfonamide (Test Compound A hereinafter) treated (n=4). Biomechanical properties are measure immediately after extraction for the fresh group. Samples of the vehicle and Test Compound A groups are placed into 6 well plates (2 fascicles/well) in 2 ml/well of serum free tissue culture medium consisting of DMEM/F12 (Gibco®, catalogue number: 31331093), N2 supplement (1× concentration, Gibco®, catalogue number: 17502048), ascorbic acid (300 ug/ml, Wako catalogue number: 013-10641) and Pen-strep (1%, Gibco®, catalogue number: 15140122). For the Test Compound group, 1 uM Test Compound A is added to the wells. Equal amount of DMSO is added to the vehicle group. Both groups were incubated at 37° C. for 4 weeks. Media are refreshed once per week.

Mechanical Testing

Samples are clamped for mechanical testing using a standard uniaxial material testing machine (ElectroPuls E3000, 50N load-cell, Instron, US) in a custom environmental testing chamber filled with PBS. Samples are pre-loaded to a position where crimp (macroscopic fascicle waviness) disappears and initial length (L0) based on grip-to-grip distance is recorded. Images of the fascicle are taken from orthogonal perspectives using two telecentric lenses (FABRIMEX T80 1.0L, Fabrimex AG, Switzerland) to characterize the ellipsoidal cross-sectional area of each specimen. Samples are ramped to failure at a constant strain rate of 0.025% L0/s. Sample lengths and corresponding forces are recorded to calculate engineering stress and strain. Young's moduli are calculated from the linear region of the stress-strain curves. Failure stress iss obtained at the point where maximum stress was reached.

In unloaded condition, tendon degeneration can thus be observed in vitro shown by morphological changes in tendon structure and decrease in biomechanical properties (failure stress and young's modulus).

Example 97: Microparticle Formulation for Injection with 4-(3-amino-1H-pyrazolo[4,3-b]pyridin-5-yl)-N-((1s,3s)-3-hydroxy-3-(trifluoromethyl)cyclobutyl)-3-methylbenzenesulfonamide (Test Compound A)

In the current invention, the microparticles formulation contains a copolymer of DL-lactide and glycolide in a 50:50 molar ratio with an ester end group plus Test Compound A is used. The total amount of Test Compound A incorporated into the microparticles ranges from 2% to 10% (w/w). The microparticles are formulated to mean mass range in size from 5 to 25 microns. The population of microparticles is formulated to be delivered through a 22 gauges or higher needles (see Table A below). Organic solvent was used for preparation of microparticles were dichloromethane (DCM) and ethyl acetate (EA) either alone or in combination with methanol (MeOH) and/or dimethyl sulfoxide (DMSO) e.g., ratio of MeOH/DMSO from 5-15% in DCM or EA as primary solvent. Additional excipients may be added such as, but not limited to, carboxymethylcellulose sodium, mannitol and ploxamer to achieve isotonicity and promote syringeability.

Test Compound A incorporated into the microparticles provides an initial release (burst) of about 5-10% of drug over a period of 1 to 2 days, followed by a steady state release of drug over a period of 21 days (FIG. 1). In-vivo the microparticles could extend the release of Test Compound A over 4 weeks in a rat model.

The detailed formulation is presented below (See also Table A):

Materials and Methods:

Formulation A: Using DCM as primary solvent:

1. Dissolve 180 mg of PLGA in 2 mL of methylene chloride (DCM) using a 4 mL vial. Prepare two vials.

2. Add 20 mg of Test Compound A to each vial. Label as vial 1 and vial 2.

3. In vial 1, add 300 uL of MeOH to obtain a clear/yellow solution.

4. In vial 2, add 120 uL of DMSO to obtain a clear/yellow solution.

5. Prepare two 250 mL beakers with 240 mL of 0.1% PVA solution and label as beaker 1 and 2. Add stir bar and allow to stir at room temperature with moderate agitation (~250 rpm).

6. Prepare two 20 mL vials with 8 mL of 2% PVA solution. Label each vial as 1 and 2.

7. Slowly pipette vial 1 to the respective 2% PVA solution vial to form a drug-polymer solution using a homogenizer (speed approx. 5000 rpm).

8. After pipetting, allow homogenizer to continue emulsification of the binary system for approximately 10 seconds.

9. Transfer the binary system to the respective 250 mL beaker (as prepared in Step 5).

10. Repeat steps 7-9 for vial 2.

11. Allow mixtures to stir overnight.

12. Label four 50 mL capillary centrifuge tubes as "1".

13. Transfer the contents of from Beaker 1 into the four (or more) 50 mL tubes and fill to 50 mL. qs with water if needed.

14. Repeat steps 12 and 13 for sample 2.

15. Ensure all tubes are of equal weight. Centrifuge all tubes 4000 rpm for 4 minutes.

16. Decant the supernatant from all vials, leave pellets undisturbed.

17. Consolidate all pellets from sample 1 tubes into one tube. Rinse each empty tube with water and collect. complete final tube to 50 mL. Vortex.

18. Repeat step 17 for sample 2.

19. Repeat steps 15 through 18 to centrifuge, decant, refill with water, and vortex for a total of 3 wash cycles.

20. Transfer the final product solutions into 4 mL glass vials (labeled 1 and 2, respectively)

21. Dip into liquid nitrogen for approximately 45 seconds.

22. Cover the vial tops with KimWipe (folded into a square, four layers thick), tape around vial to secure, and ensure tape is labeled 1 and 2 for the respective sample.

23. Store samples under vacuum for 24 hours

24. Create a calibration curve using Test Compound A in ACN:H2O 1:1, 1 mg/mL working solution, three standards [0.1 mg/mL], [0.01 mg/mL], [0.001 mg/mL]

The dried particles are analyzed for encapsulation efficiency using UPLC as follows:

25. 0.97 mg of (1) PLGA particles are dissolved in 250 uL of acetonitrile. 750 uL of methanol is added to precipitate PLGA (Test Compound A is dissolved in methanol).

26. 1.01 mg of (2) PLGA particles are dissolved in 250 uL of acetonitrile. 750 uL of methanol is added to precipitate PLGA (Test Compound A is dissolved in methanol).

27. The suspension is vortexed and centrifuged at 15000 rpm using a 0.22 um filter eppendorf centrifuge tube 28. The clear solution in analyzed using UPLC for drug loading Formulation B: Using EA as Primary Solvent:

The procedure used is exactly the same as for Formulation A. The only difference is that in step 3, the amount of MeOH added is 120 uL and in step 4 the amount of DMSO added is 50 uL.

TABLE A

Formulation of Test Compound A ("drug") into PLGA microparticles with different drug loading and PLGA composition

| Formulation | PLGA 50:50 | Mw (kDa) ester capped | Drug loading (w/w) % |
|---|---|---|---|
| 1 | Linear | 7-17 | 2.15 |
| 2 | Linear | 7-17 | 2.09 |
| 3 | Linear | 7-17 | 9.12 |
| 4 | Linear | 7-17 | 8.52 |

Test Compound A incorporated into the microparticles provides an initial release (burst) of about 5-10% of drug over a period of 1 to 2 days, followed by a steady state release of drug over a period of 21 days (FIG. 1). In-vivo the microparticles could extend the release of Test Compound A over 4 weeks in a rat model.

Instead of Test Compound A, any other one of the exemplified compounds can be formulated using the same procedure as in the present example. The microparticles can also be produced using Ethyl acetate as a primary solvent to increase the drug loading and achieve a controlled release of the encapsulated material.

The invention claimed is:

1. A method of treating a tendon injury in a subject in need thereof, the method comprising administering to the subject a therapeutically effective amount of a compound of formula (I) or a pharmaceutically acceptable salt thereof, wherein:

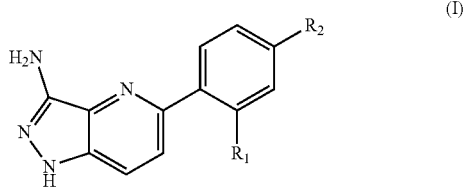

(I)

$R_1$ is selected from C1-C3alkyl and halogen;
$R_2$ is —$SO_2NR_5R_6$;
$R_5$ is selected from H and $C_1$-$C_3$alkyl;
$R_6$ is selected from a $C_3$-$C_6$cycloalkyl optionally substituted with $R_7$; phenyl optionally substituted with halogen; $C_1$-$C_6$alkyl optionally substituted with hydroxyl; 4- to 6-membered heterocyclic non-aromatic ring comprising at least one heteroatom selected from N, O or S optionally substituted with oxo; and benzyl; and
$R_7$ is independently selected from hydroxyl, halo$C_1$-$C_3$alkyl, halogen, $C_1$-$C_3$alkyl, C(O)OH, and hydroxy$C_1$-$C_3$alkyl;
or
$R_5$ and $R_6$ together with the N atom to which they are attached form a 4-, 5- or 6-membered heterocyclic non-aromatic ring optionally comprising one additional heteroatom selected from N, O, or S, wherein the ring is optionally substituted with $R_8$; or a 6- to 8-membered saturated bicyclic ring system; and
$R_8$ is independently selected from halogen, hydroxy$C_1$-$C_3$alkyl, C(O)$NH_2$, hydroxyl, halo$C_1$-$C_3$alkyl optionally substituted with hydroxyl, phenoxy, and $SO_2C_1$-$C_3$alkyl.

2. The method of claim 1, wherein:
$R_1$ is chloro or methyl; and
$R_2$ is $SO_2NR_5R_6$.

3. The method of claim 1, wherein:
$R_5$ is H or methyl;
$R_6$ is $C_4$-$C_6$cycloalkyl optionally substituted once or more than once with $R_7$; and
$R_7$ is independently selected from hydroxyl, halo$C_1$-$C_3$alkyl, halogen, $C_1$-$C_3$alkyl, and hydroxy$C_1$-$C_3$alkyl.

4. The method of claim 1, wherein the compound is 4-(3-amino-1H-pyrazolo[4,3-b]pyridin-5-yl)-3-chloro-N-((1s,3s)-3-hydroxy-3-(trifluoromethyl)cyclobutyl)benzenesulfonamide or a pharmaceutically acceptable salt thereof.

5. The method of claim 1, wherein the compound is 4-(3-amino-1H-pyrazolo[4,3-b]pyridin-5-yl)-N-(3,3-difluorocyclobutyl)-3-methylbenzenesulfonamide or a pharmaceutically acceptable salt thereof.

6. The method of claim 1, wherein the compound is 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide or a pharmaceutically acceptable salt thereof.

7. The method of claim 1, wherein the compound is 4-(3-amino-1H-pyrazolo[4,3-b]pyridin-5-yl)-3-chloro-N-(1,1-dioxidothietan-3-yl)benzenesulfonamide or a pharmaceutically acceptable salt thereof.

8. The method of claim 1, wherein the compound is 4-(3-amino-1H-pyrazolo[4,3-b]pyridin-5-yl)-3-chloro-N-phenylbenzenesulfonamide or a pharmaceutically acceptable salt thereof.

9. The method of claim 1, wherein the compound is 1-((4-(3-amino-1H-pyrazolo[4,3-b]pyridin-5-yl)-3-methylphenyl)sulfonyl)-3-(trifluoromethyl)azetidin-3-ol or a pharmaceutically acceptable salt thereof.

10. The method of claim 1, wherein the tendon injury is selected from a tendon partial rupture, a tendon full rupture, and tendon degeneration.

11. The method of claim 1, wherein the tendon is the Achilles tendon or a rotator cuff tendon.

12. A method of treating a ligament injury in a subject in need thereof, the method comprising administering to the subject a therapeutically effective amount of a compound of formula (I) or a pharmaceutically acceptable salt thereof, wherein:

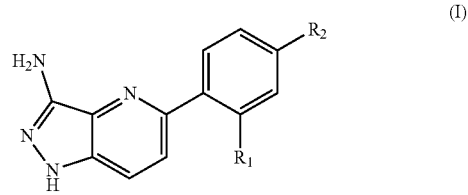

(I)

$R_1$ is selected from $C_1$-$C_3$alkyl and halogen;
$R_2$ is —$SO_2NR_5R_6$;
$R_5$ is selected from H and $C_1$-$C_3$alkyl;
$R_6$ is selected from a $C_3$-$C_6$cycloalkyl optionally substituted with $R_7$; phenyl optionally substituted with halogen; $C_1$-$C_6$alkyl optionally substituted with hydroxyl; 4- to 6-membered heterocyclic non-aromatic ring comprising at least one heteroatom selected from N, O or S optionally substituted with oxo; and benzyl; and
$R_7$ is independently selected from hydroxyl, halo$C_1$-$C_3$alkyl, halogen, $C_1$-$C_3$alkyl, C(O)OH, and hydroxy$C_1$-$C_3$alkyl;
or
$R_5$ and $R_6$ together with the N atom to which they are attached form a 4-, 5- or 6-membered heterocyclic non-aromatic ring optionally comprising one additional heteroatom selected from N, O, or S, wherein the ring is optionally substituted with $R_8$; or a 6- to 8-membered saturated bicyclic ring system; and
$R_8$ is independently selected from halogen, hydroxy$C_1$-$C_3$alkyl, C(O)$NH_2$, hydroxyl, halo$C_1$-$C_3$alkyl optionally substituted with hydroxyl, phenoxy, and $SO_2C_1$-$C_3$alkyl.

13. The method of claim 12, wherein:
$R_1$ is chloro or methyl; and
$R_2$ is $SO_2NR_5R_6$.

14. The method of claim 12, wherein:
$R_5$ is H or methyl;
$R_6$ is $C_4$-$C_6$cycloalkyl optionally substituted once or more than once with $R_7$; and
$R_7$ is independently selected from hydroxyl, halo$C_1$-$C_3$alkyl, halogen, $C_1$-$C_3$alkyl, and hydroxy$C_1$-$C_3$alkyl.

15. The method of claim 12, wherein the compound is 4-(3-amino-1H-pyrazolo[4,3-b]pyridin-5-yl)-3-chloro-N-((1s,3s)-3-hydroxy-3-(trifluoromethyl)cyclobutyl)benzenesulfonamide or a pharmaceutically acceptable salt thereof.

16. The method of claim 12, wherein the compound is 4-(3-amino-1H-pyrazolo[4,3-b]pyridin-5-yl)-N-(3,3-difluorocyclobutyl)-3-methylbenzenesulfonamide or a pharmaceutically acceptable salt thereof.

17. The method of claim 12, wherein the compound is 4-(3-amino-1H-pyrazolo[4,3-b]pyridin-5-yl)-N-((1s,3s)-3-hydroxy-3-(trifluoromethyl)cyclobutyl)-N,3-dimethylbenzenesulfonamide or a pharmaceutically acceptable salt thereof.

18. The method of claim 12, wherein the compound is 4-(3-amino-1H-pyrazolo[4,3-b]pyridin-5-yl)-3-chloro-N-(1,1-dioxidothietan-3-yl)benzenesulfonamide or a pharmaceutically acceptable salt thereof.

19. The method of claim 12, wherein the compound is 4-(3-amino-1H-pyrazolo[4,3-b]pyridin-5-yl)-3-chloro-N-phenylbenzenesulfonamide or a pharmaceutically acceptable salt thereof.

20. The method of claim 12, wherein the compound is 1-((4-(3-amino-1H-pyrazolo[4,3-b]pyridin-5-yl)-3-methylphenyl)sulfonyl)-3-(trifluoromethyl)azetidin-3-ol or a pharmaceutically acceptable salt thereof.

21. The method of claim 12, wherein the ligament injury is selected from a ligament partial rupture, a ligament full rupture, and ligament degeneration.

\* \* \* \* \*

SEQUENCE LISTING

```
<160> NUMBER OF SEQ ID NOS: 12

<210> SEQ ID NO 1
<211> LENGTH: 21
<212> TYPE: DNA
<213> ORGANISM: Rattus norvegicus

<400> SEQUENCE: 1
atcaccatct tccaggagcg a                                            21

<210> SEQ ID NO 2
<211> LENGTH: 18
<212> TYPE: DNA
<213> ORGANISM: Rattus norvegicus

<400> SEQUENCE: 2
gatgcccagg gaagacag                                                18

<210> SEQ ID NO 3
<211> LENGTH: 18
<212> TYPE: DNA
<213> ORGANISM: Rattus norvegicus

<400> SEQUENCE: 3
gctcctcctg agcgcaag                                                18

<210> SEQ ID NO 4
<211> LENGTH: 20
<212> TYPE: DNA
<213> ORGANISM: Rattus norvegicus

<400> SEQUENCE: 4
cccaaacaga tctgcacctt                                              20

<210> SEQ ID NO 5
<211> LENGTH: 21
<212> TYPE: DNA
<213> ORGANISM: Rattus norvegicus
```

```
<400> SEQUENCE: 5
tggatcaatc ccactctaat a                                              21

<210> SEQ ID NO 6
<211> LENGTH: 19
<212> TYPE: DNA
<213> ORGANISM: Rattus norvegicus

<400> SEQUENCE: 6
cctggctctc gaggtgaac                                                 19

<210> SEQ ID NO 7
<211> LENGTH: 21
<212> TYPE: DNA
<213> ORGANISM: Rattus norvegicus

<400> SEQUENCE: 7
agccttctcc atggtggtga a                                              21

<210> SEQ ID NO 8
<211> LENGTH: 22
<212> TYPE: DNA
<213> ORGANISM: Rattus norvegicus

<400> SEQUENCE: 8
cacaatgaag cattttgggt ag                                             22

<210> SEQ ID NO 9
<211> LENGTH: 20
<212> TYPE: DNA
<213> ORGANISM: Rattus norvegicus

<400> SEQUENCE: 9
catctgctgg aaggtggaca                                                20

<210> SEQ ID NO 10
<211> LENGTH: 20
<212> TYPE: DNA
<213> ORGANISM: Rattus norvegicus

<400> SEQUENCE: 10
tctgtcacgg tctttgctca                                                20

<210> SEQ ID NO 11
<211> LENGTH: 21
<212> TYPE: DNA
<213> ORGANISM: Rattus norvegicus

<400> SEQUENCE: 11
tcgctggtag gaaagtgaag a                                              21

<210> SEQ ID NO 12
<211> LENGTH: 18
<212> TYPE: DNA
<213> ORGANISM: Rattus norvegicus

<400> SEQUENCE: 12
caatgcccag aggaccag                                                  18
```